(12) United States Patent
Hatakeyama et al.

(10) Patent No.: US 11,181,823 B2
(45) Date of Patent: *Nov. 23, 2021

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP); Takayuki Fujiwara, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 169 days.

This patent is subject to a terminal disclaimer.

(21) Appl. No.: 16/565,804

(22) Filed: Sep. 10, 2019

(65) Prior Publication Data

US 2020/0089112 A1 Mar. 19, 2020

(30) Foreign Application Priority Data

Sep. 18, 2018 (JP) .............................. JP2018-173598

(51) Int. Cl.

| | |
|---|---|
| *G03F 7/004* | (2006.01) |
| *G03F 7/038* | (2006.01) |
| *C07C 381/12* | (2006.01) |
| *C07C 63/08* | (2006.01) |
| *C07C 59/115* | (2006.01) |
| *C07C 63/70* | (2006.01) |
| *C07D 275/06* | (2006.01) |
| *C07C 59/135* | (2006.01) |
| *C07C 65/05* | (2006.01) |
| *C07C 65/21* | (2006.01) |
| *C07C 309/58* | (2006.01) |
| *C08F 220/16* | (2006.01) |
| *C08F 212/14* | (2006.01) |
| *G03F 7/039* | (2006.01) |
| *G03F 7/16* | (2006.01) |
| *C07C 61/135* | (2006.01) |
| *C07C 205/58* | (2006.01) |
| *C07C 311/09* | (2006.01) |
| *C07C 309/19* | (2006.01) |
| *C07C 309/12* | (2006.01) |
| *G03F 7/20* | (2006.01) |
| *G03F 7/38* | (2006.01) |
| *G03F 7/32* | (2006.01) |

(52) U.S. Cl.
CPC .......... *G03F 7/0045* (2013.01); *C07C 59/115* (2013.01); *C07C 59/135* (2013.01); *C07C 61/135* (2013.01); *C07C 63/08* (2013.01); *C07C 63/70* (2013.01); *C07C 65/05* (2013.01); *C07C 65/21* (2013.01); *C07C 205/58* (2013.01); *C07C 309/12* (2013.01); *C07C 309/19* (2013.01); *C07C 309/58* (2013.01); *C07C 311/09* (2013.01); *C07C 381/12* (2013.01); *C07D 275/06* (2013.01); *C08F 212/14* (2013.01); *C08F 220/16* (2013.01); *G03F 7/0382* (2013.01); *G03F 7/0392* (2013.01); *C07C 2603/74* (2017.05); *G03F 7/162* (2013.01); *G03F 7/168* (2013.01); *G03F 7/2004* (2013.01); *G03F 7/2006* (2013.01); *G03F 7/2037* (2013.01); *G03F 7/322* (2013.01); *G03F 7/38* (2013.01)

(58) Field of Classification Search
CPC ...... G03F 7/0045; G03F 7/0046; G03F 7/038; G03F 7/0382; G03F 7/039; G03F 7/0392; G03F 7/0395; G03F 7/0397
See application file for complete search history.

(56) References Cited

U.S. PATENT DOCUMENTS

| | | | | |
|---|---|---|---|---|
| 2017/0205709 | A1* | 7/2017 | Hatakeyama | ........... G03F 7/322 |
| 2018/0095364 | A1* | 4/2018 | LaBeaume | ............ G03F 7/0045 |

FOREIGN PATENT DOCUMENTS

| | | | |
|---|---|---|---|
| JP | 2001-194776 | A | 7/2001 |
| JP | 2002-226470 | A | 8/2002 |
| JP | 2002-363148 | A | 12/2002 |
| JP | 2018118962 | A * | 8/2018 |
| WO | 2008/066011 | A1 | 6/2008 |

OTHER PUBLICATIONS

English Machine Translation of Matsuyama (JP2018118962A) (Year: 2018).*

* cited by examiner

*Primary Examiner* — John A McPherson
*Assistant Examiner* — Nicholas E Brown
(74) *Attorney, Agent, or Firm* — Westerman, Hattori, Daniels & Adrian, LLP

(57) ABSTRACT

A resist composition comprising a base polymer and a quencher containing a sulfonium salt having an iodized benzene ring offers a high sensitivity, minimal LWR and improved CDU independent of whether it is of positive or negative tone.

15 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2018-173598 filed in Japan on Sep. 18, 2018, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

As the pattern feature size is reduced, approaching to the diffraction limit of light, light contrast lowers. In the case of positive resist film, a lowering of light contrast leads to reductions of resolution and focus margin of hole and trench patterns.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein polarity switch or crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 to 3.

With respect to the acid labile group used in (meth)acrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 4 discloses a resist composition comprising a sulfoniun or iodonium salt capable of generating carboxylic acid as a quencher.

Sulfonium and iodonium salt type quenchers are photo-decomposable like photoacid generators. That is, the amount of quencher in the exposed region is reduced. Since acid is generated in the exposed region, the reduced amount of quencher leads to a relatively high concentration of acid and hence, an improved contrast. However, the acid diffusion in the exposed region is not suppressed, indicating the difficulty of acid diffusion control.

CITATION LIST

Patent Document 1: JP-A 2001-194776
Patent Document 2: JP-A 2002-226470
Patent Document 3: JP-A 2002-363148
Patent Document 4: WO 2008/066011

DISCLOSURE OF INVENTION

For the acid-catalyzed chemically amplified resist, it is desired to develop a quencher capable of reducing the LWR of line patterns or improving the CDU of hole patterns and giving a high sensitivity.

An object of the invention is to provide a resist composition which exhibits a high sensitivity and a reduced LWR or improved CDU, independent of whether it is of positive tone or negative tone; and a pattern forming process using the same.

The inventors have found that using a sulfonium salt having an iodized benzene ring as the quencher, a resist material having a high sensitivity, reduced LWR, improved CDU, high contrast, improved resolution, and wide process margin is obtainable.

In one aspect, the invention provides a resist composition comprising a quencher containing a sulfonium salt having the formula (1).

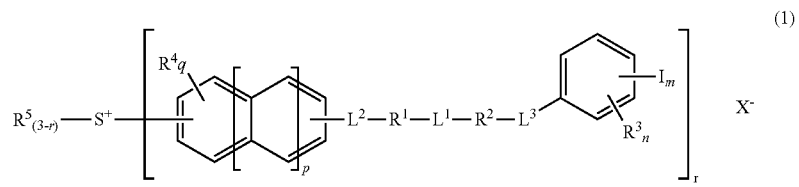

Herein $R^1$ and $R^2$ are each independently a single bond or a $C_1$-$C_{20}$ divalent aliphatic hydrocarbon group which may contain an ether bond, ester bond or hydroxyl; $L^1$ is an ester bond, ether bond or amide bond; $L^2$ and $L^3$ are each independently a single bond, ester bond, ether bond or amide bond; $R^3$ is hydroxyl, carboxyl, nitro, cyano, fluorine, chlorine, bromine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, hydroxyl or amino, or —$NR^{3A}$—C(=O)—$R^{3B}$ or —$NR^{3A}$—C(=O)—O—$R^{3B}$, wherein $R^{3A}$ is hydrogen or a $C_1$-$C_6$ alkyl group which may contain halogen, hydroxyl, $C_1$-$C_{10}$ alkoxy, $C_2$-$C_{10}$ acyl or $C_2$-$C_{10}$ acyloxy, $R^{3B}$ is a $C_1$-$C_{16}$ alkyl, $C_2$-$C_{16}$ alkenyl or $C_6$-$C_{12}$ aryl group, which may contain halogen, hydroxyl, $C_1$-$C_{10}$ alkoxy, $C_2$-$C_{10}$ acyl or $C_2$-$C_{10}$ acyloxy; $R^4$ is hydroxyl, carboxyl, nitro, cyano, fluorine, chlorine, bromine, iodine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, iodine, hydroxyl, amino or ether bond; $R^5$ is a $C_1$-$C_{20}$ monovalent hydrocarbon group which may contain a heteroatom, in case of r=1, two $R^5$ may be the same or different and may bond together to form a ring with the sulfur atom to which they are attached; $X^-$ is a carboxylic acid anion, amic acid anion, fluorine-free sulfonic acid anion or halide ion; m is an integer of 1 to 5, n is an integer of 0 to 3, the sum of m+n is 1 to 5, p is 0 or 1, q is an integer of 0 to 4, and r is an integer of 1 to 3. Preferably, m is an integer of 2 to 5.

The resist composition may further comprise an organic solvent and/or an acid generator capable of generating a fluorosulfonic acid, fluoroimidic acid or fluoromethide acid.

The resist composition may further comprise a base polymer. Preferably, the base polymer comprises recurring units having the formula (a1) or recurring units having the formula (a2).

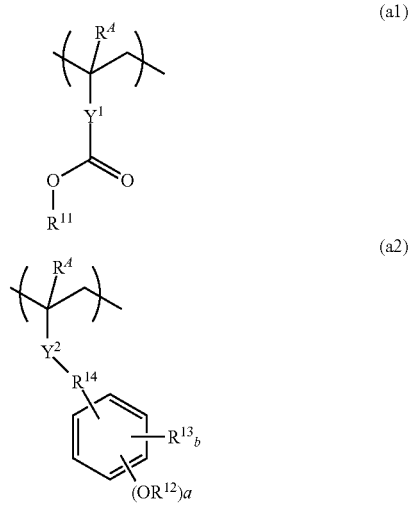

Herein $R^A$ is each independently hydrogen or methyl, $Y^1$ is a single bond, phenylene group, naphthylene group, or $C_1$-$C_{12}$ linking group containing an ester bond or lactone ring, $Y^2$ is a single bond or ester bond, $R^{11}$ and $R^{12}$ each are an acid labile group, $R^{13}$ is fluorine, trifluoromethyl, cyano, $C_1$-$C_6$ alkyl, $C_1$-$C_6$ alkoxy, $C_2$-$C_7$ acyl, $C_2$-$C_7$ acyloxy, or $C_2$-$C_7$ alkoxycarbonyl group, $R^{14}$ is a single bond or a $C_1$-$C_6$ straight or branched alkanediyl group in which some carbon may be replaced by an ether bond or ester bond, a is 1 or 2, b is an integer of 0 to 4, the sum of a+b is 1 to 5.

In one embodiment, the resist composition is a chemically amplified positive resist composition.

In another embodiment, the base polymer is free of an acid labile group, and the resist composition is a chemically amplified negative resist composition.

In a preferred embodiment, the base polymer further comprises recurring units of at least one type selected from the formulae (f1) to (f3).

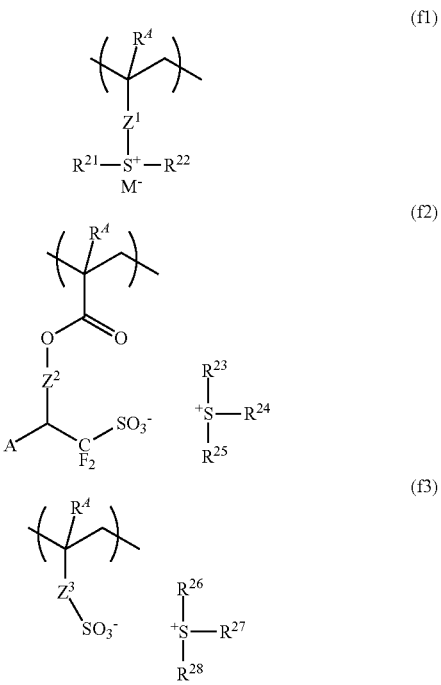

Herein $R^A$ is each independently hydrogen or methyl; $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain carbonyl, ester bond, ether bond or hydroxyl; $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain carbonyl, ester bond or ether bond; $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain carbonyl, ester bond, ether bond or hydroxyl; $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached; A is hydrogen or trifluoromethyl; and $M^-$ is a non-nucleophilic counter ion.

The resist composition may further comprise a surfactant.

In another aspect, the invention provides a process for forming a pattern comprising the steps of applying the resist composition defined above onto a substrate, baking to form a resist film, exposing the resist film to high-energy radiation, and developing the exposed resist film in a developer.

Preferably, the high-energy radiation is ArF excimer laser radiation of wavelength 193 nm, KrF excimer laser radiation of wavelength 248 nm, EB, or EUV of wavelength 3 to 15 nm.

Advantageous Effects of Invention

The quencher in the form of a sulfonium salt having an iodized benzene ring provides a resist composition with a high sensitivity because iodine is fully absorptive to EUV of wavelength 13.5 nm and generates secondary electrons during EUV exposure to promote decomposition. Because of the large atomic weight of iodine, the quencher is quite effective for suppressing acid diffusion, leading to reduced image blur and hence, reduced LWR and improved CDU. By virtue of these advantages, a resist composition having a high sensitivity, low LWR and improved CDU is designed.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. The term "iodized" or "fluorinated" compound means that a compound contains iodine or fluorine.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Resist Composition One embodiment of the invention is a resist composition comprising a sulfonium salt having an iodized benzene ring and optionally, a base polymer. The sulfonium salt is an acid generator in that an acid is generated from the anion moiety as a result of the cation moiety being decomposed upon light exposure. However, the anion moiety is a weak acid which is insufficient to induce polarity switch or crosslinking reaction. When an acid generator capable of generating a strong acid is separately added, ion exchange takes place between the sulfonium salt and the strong acid generated therefrom. Thus the sulfonium salt functions as a quencher for neutralizing the strong acid.

The sulfonium salt type quencher used herein traps an acid to control acid diffusion by the same mechanism as in Patent Document 4. The contrast is enhanced by the photodecomposition of the quencher.

The sulfonium salt type quencher used herein is different from Patent Document 4 in that it has a high absorptivity to EUV radiation and a high decomposition efficiency because an iodized benzene ring is contained in its cation moiety. Since the sulfonium salt 1 to relies on the decomposition of the cation moiety, increasing the absorption of the cation moiety is effective for gaining a high decomposition efficiency.

In the case of an acid generator, increasing the decomposition efficiency directly leads to a higher sensitivity. At the same time, CDU and LWR may be reduced by using a bulky anion moiety to control the diffusion of the generated acid. In the case of a quencher, however, increasing the decomposition efficiency leads to a lowering of quencher concentration for controlling acid diffusion. Then a higher sensitivity is obtained, but CDU and LWR are substantially degraded.

The sulfonium salt having an iodized benzene ring is effective for suppressing acid diffusion even at a low quencher concentration because the cation moiety contains iodine of large atomic weight. In addition, the sulfonium salt is fully compatible with a polymer and well dispersible therein. These properties lead to improvements in LWR and CDU.

The quencher in the form of a sulfonium salt having an iodized benzene ring exerts a LWR or CDU improving effect, which may stand good either in positive and negative tone pattern formation by aqueous alkaline development or in negative tone pattern formation by organic solvent development.

The sulfonium salt having an iodized benzene ring may be used as a positive resist material in the following sense. When a resist film is formed by dissolving the sulfonium salt alone or in admixture with a base polymer in a solvent and coating the solution, the resist film is alkali soluble in the exposed region.

Sulfonium Salt Having Iodized Benzene Ring

The sulfonium salt in the resist composition has the formula (1).

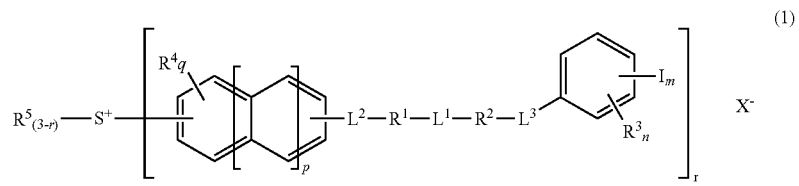

(1)

In formula (1), $R^1$ and $R^2$ are each independently a single bond or a $C_1$-$C_{20}$ divalent aliphatic hydrocarbon group which may contain an ether bond, ester bond or hydroxyl moiety.

The $C_1$-$C_{20}$ divalent aliphatic hydrocarbon group may be straight, branched or cyclic, and examples thereof include straight alkanediyl groups such as methylene, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl; branched alkanediyl groups such as ethane-1,1-diyl, propane-1,1-diyl, propane-1,2-diyl, propane-2,2-diyl, butane-1,3-diyl, butane-2,2-diyl, pentane-1,3-diyl, pentane-3,3-diyl, 2-methylpropane-1,1-diyl; cyclic alkanediyl groups such as cyclopropanediyl, cyclobutanediyl, cyclopentanediyl, cyclohexanediyl; and divalent unsaturated aliphatic hydrocarbon groups such as methylidene and propene-3,3-diyl. Of these, straight or branched alkanediyl groups are preferred.

In formula (1), $L^1$ is an ester bond, ether bond or amide bond. $L^2$ and $L^3$ are each independently a single bond, ester bond, ether bond or amide bond.

In formula (1), $R^3$ is hydroxyl, carboxyl, nitro, cyano, fluorine, chlorine, bromine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, hydroxyl moiety or amino moiety, or —NR$^{3A}$—C(=O)—R$^{3B}$ or —NR$^{3A}$—C(=O)—O—R$^{3B}$, wherein R$^{3A}$ is hydrogen or a C$_1$-C$_6$ alkyl group which may contain halogen, hydroxyl, C$_1$-C$_{10}$ alkoxy, C$_2$-C$_{10}$ acyl or C$_2$-C$_{10}$ acyloxy moiety, R$^{3B}$ is a C$_1$-C$_{16}$ alkyl, C$_2$-C$_{16}$ alkenyl or C$_6$-C$_{12}$ aryl group, which may contain halogen, hydroxyl, C$_1$-C$_{10}$ alkoxy, C$_2$-C$_{10}$ acyl or C$_2$-C$_{10}$ acyloxy moiety.

In formula (1), R$^4$ is hydroxyl, carboxyl, nitro, cyano, fluorine, chlorine, bromine, iodine, amino, or a C$_1$-C$_{20}$ alkyl, C$_1$-C$_{20}$ alkoxy, C$_2$-C$_{20}$ acyloxy, C$_2$-C$_{20}$ alkoxycarbonyl or C$_1$-C$_4$ alkylsulfonyloxy group, which may contain fluorine, chlorine, bromine, iodine, hydroxyl, amino or ether bond.

The alkyl group may be straight, branched or cyclic, and examples thereof include methyl, ethyl, n-propyl, isopropyl, n-butyl, isobutyl, sec-butyl, tert-butyl, n-pentyl, neopentyl, cyclopentyl, n-hexyl, cyclohexyl, n-heptyl, n-octyl, 2-ethylhexyl, n-nonyl, n-decyl, n-undecyl, n-dodecyl, n-tridecyl, n-pentadecyl and n-hexadecyl.

The alkoxy group may be straight, branched or cyclic, and examples thereof include methoxy, ethoxy, n-propyloxy, isopropyloxy, n-butyloxy, isobutyloxy, sec-butyloxy, tert-butyloxy, n-pentyloxy, neopentyloxy, cyclopentyloxy, n-hexyloxy, cyclohexyloxy, n-heptyloxy, n-octyloxy, 2-ethylhexyloxy, n-nonyloxy, n-decyloxy, n-undecyloxy, n-dodecyloxy, n-tridecyloxy, n-pentadecyloxy, and n-hexadecyloxy.

Suitable acyl groups include acetyl, propionyl, butyryl, and isobutyryl.

Suitable acyloxy groups include acetyloxy, propionyloxy, butyryloxy, and isobutyryloxy.

Suitable alkoxycarbonyl groups include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, neopentyloxycarbonyl, cyclopentyloxycarbonyl, n-hexyloxycarbonyl, cyclohexyloxycarbonyl, n-heptyloxycarbonyl, n-octyloxycarbonyl, 2-ethylhexyloxycarbonyl, n-nonyloxycarbonyl, n-decyloxycarbonyl, n-undecyloxycarbonyl, n-dodecyloxycarbonyl, n-tridecyloxycarbonyl, and n-pentadecyloxycarbonyl.

The alkenyl group may be straight, branched or cyclic, and examples thereof include vinyl, 1-propenyl, 2-propenyl, butenyl, hexenyl, and cyclohexenyl.

Suitable aryl groups include phenyl, tolyl, xylyl, 1-naphthyl, and 2-naphthyl.

In formula (1), R$^5$ is a C$_1$-C$_{20}$ monovalent hydrocarbon group which may contain a heteroatom. The monovalent hydrocarbon group may be straight, branched or cyclic, and examples thereof include C$_1$-C$_{20}$ alkyl groups, C$_2$-C$_{20}$ alkenyl groups, C$_2$-C$_{24}$ alkynyl groups, C$_6$-C$_{20}$ aryl groups, C$_7$-C$_{20}$ aralkyl groups, and combinations thereof. In these groups, some or all hydrogen may be substituted by hydroxyl moiety, carboxyl moiety, halogen, cyano moiety, amino moiety, nitro moiety, sultone ring-containing moiety, sulfone moiety or sulfonium salt-containing moiety, or an ether bond, ester bond, carbonyl moiety, sulfide bond, sulfonyl moiety or amide moiety may intervene in a carbon-carbon bond.

In case of r=1, two R$^5$ may be the same or different and may bond together to form a ring with the sulfur atom to which they are attached. Examples of the ring include the following structures.

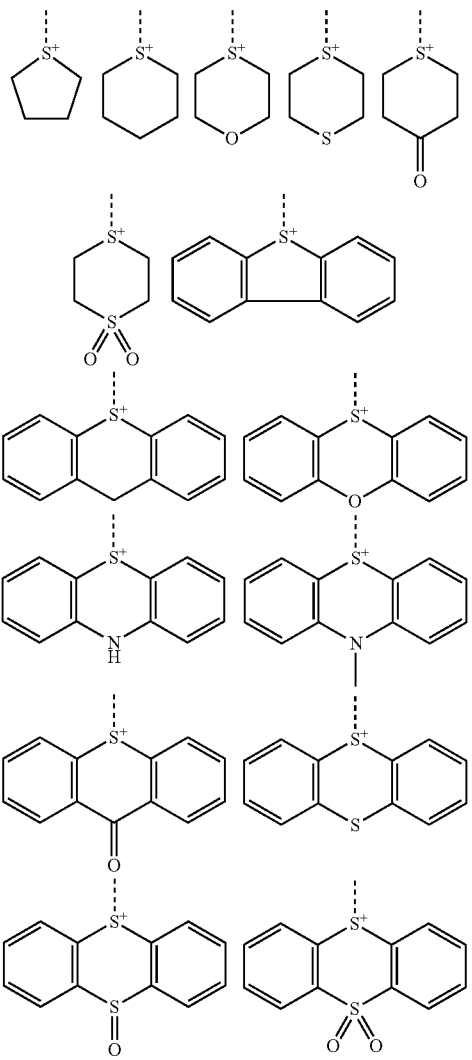

In these formulae, the broken line designates a valence bond to the aromatic ring to which the sulfur atom in formula (1) bonds.

In formula (1), X$^-$ is a carboxylic acid anion, amic acid anion, fluorine-free sulfonic acid anion or halide ion. Examples include halide ions such as chloride, bromide and iodide ions; carboxylic acid anions as described in JP 3991462 and JP 4226803; fluorocarboxylic acid anions as described in JP-A 2013-092657, JP-A 2015-054833 and JP-A 2015-132679; iodized benzoic acid anions as described in JP-A 2017-219836; amic acid anions as described in JP-A 2013-145256; nitrogen-containing carboxylic acid or sulfonic acid anions as described in JP-A 2016-088898, JP-A 2016-044135, JP-A 2017-078741, JP-A 2017-076049, JP-A 2017-058454, and JP-A 2017-129695; fluorine-free sulfonic acid anions as described in JP-A 2003-246774 and JP-A 2010-155824; and saccharin as described in 2001-330947. These anions do not induce deprotection reaction of acid labile groups in positive resist compositions or crosslinking reaction or polarity switch reaction in negative resist compositions. Thus when an acid generator capable of generating a strong acid is co-present with the sulfonium salt, the sulfonium salt functions as a quencher for controlling the diffusion of strong acid.

In formula (1), m is an integer of 1 to 5, n is an integer of 0 to 3, the sum of m+n is 1 to 5, p is 0 or 1, q is an integer of 0 to 4, and r is an integer of 1 to 3.
Examples of the cation in the sulfonium salt having formula (1) are given below, but not limited thereto.
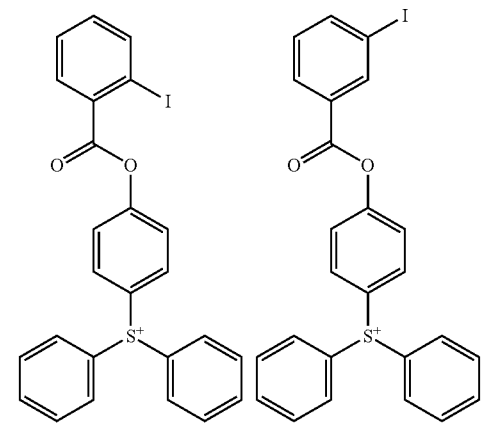
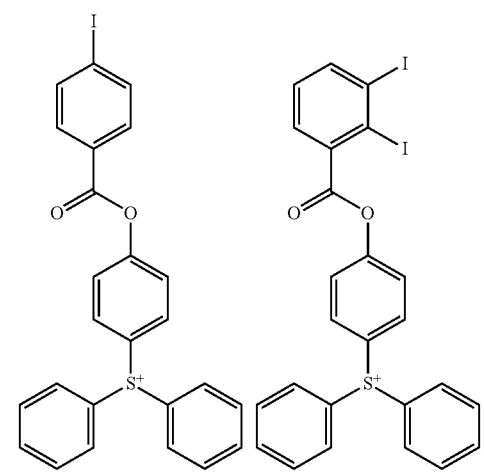
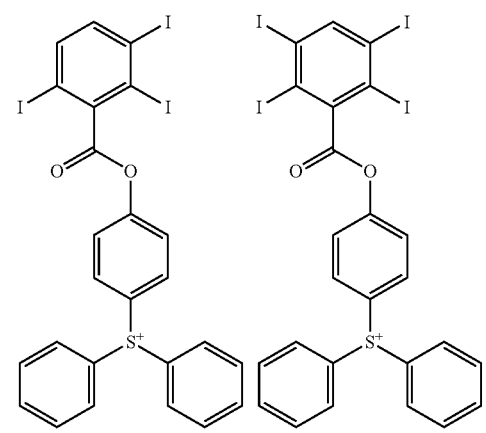
-continued
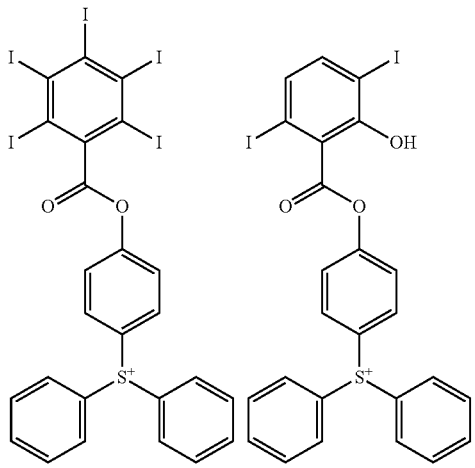
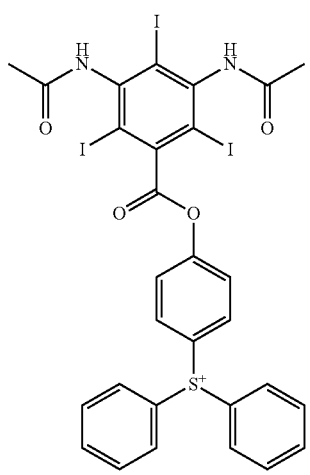
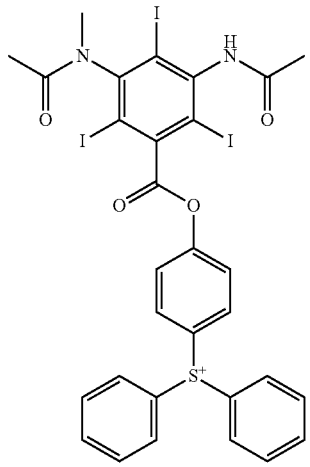

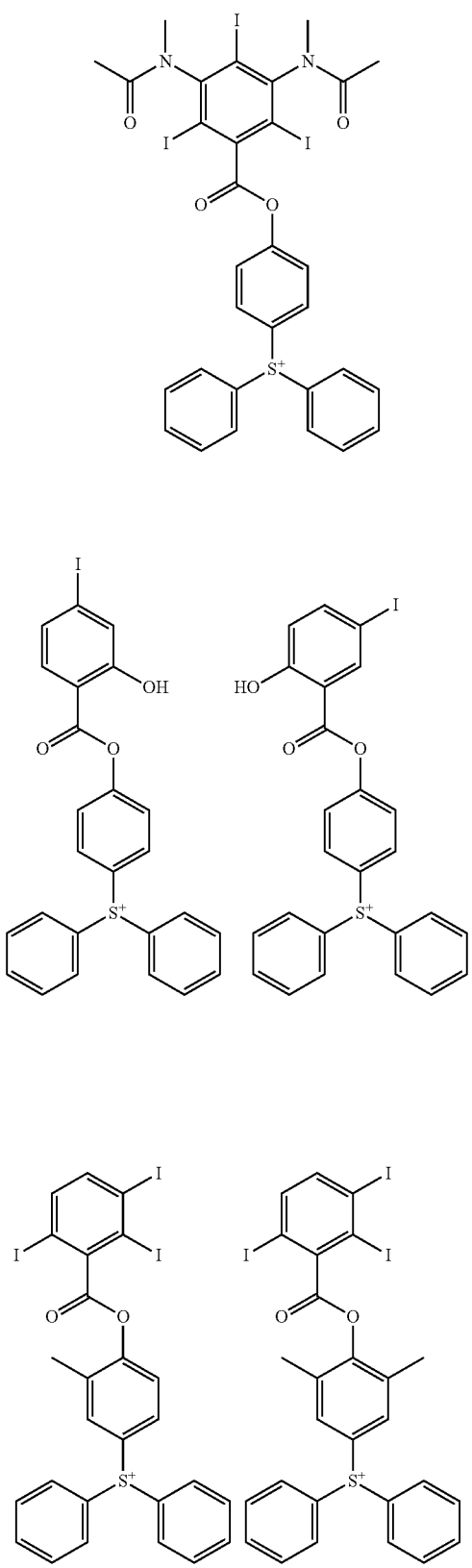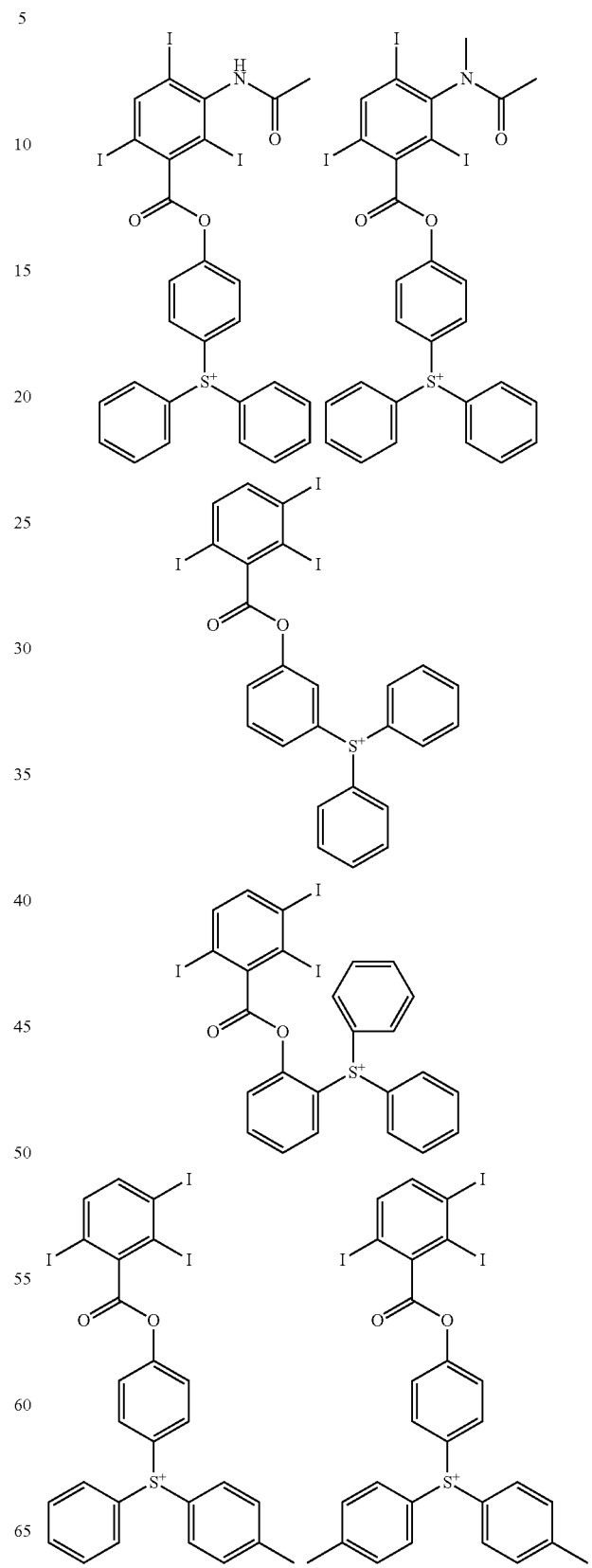

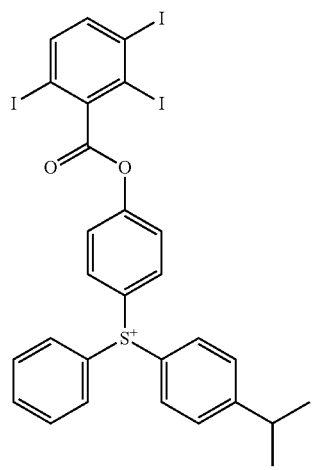
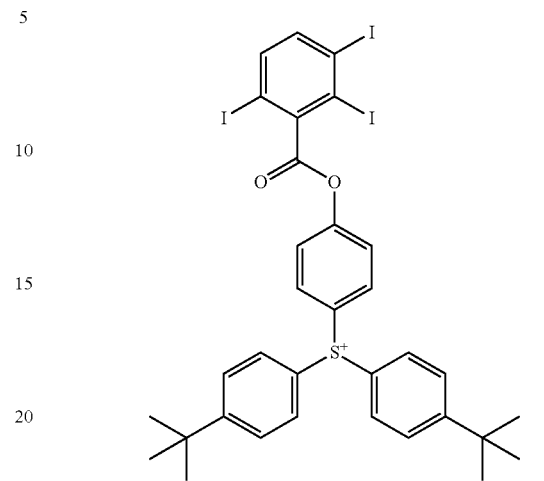
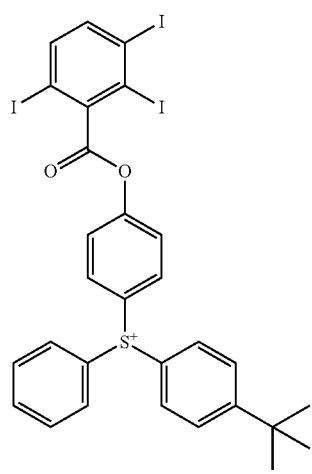
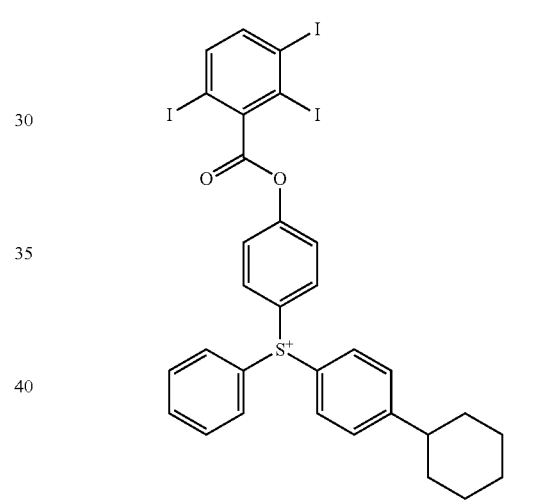
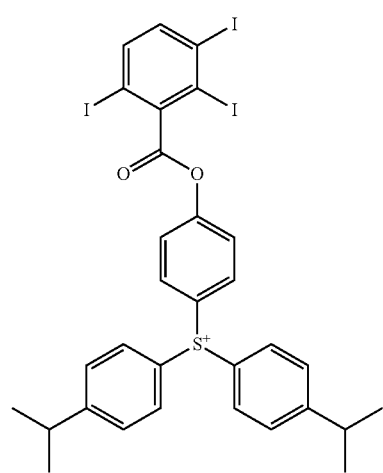
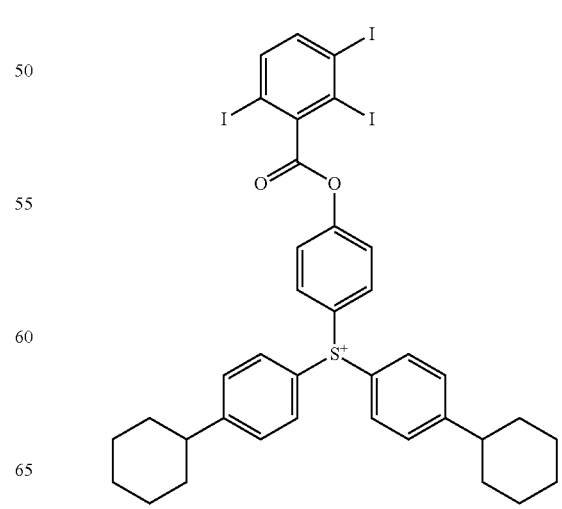

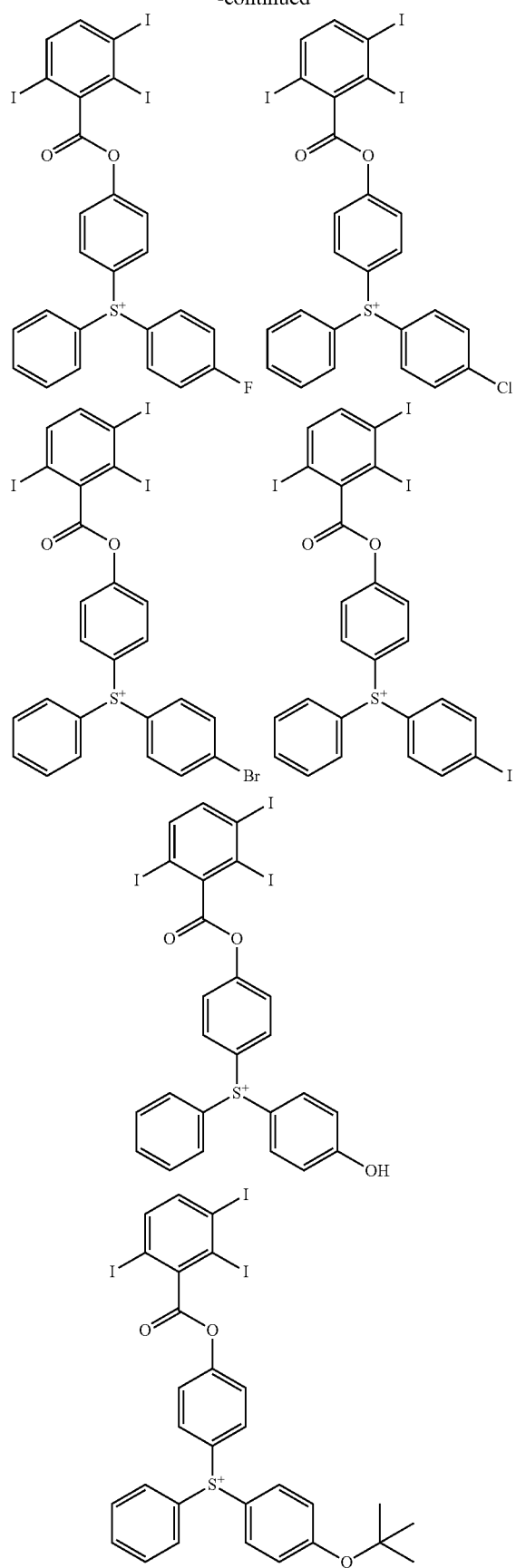
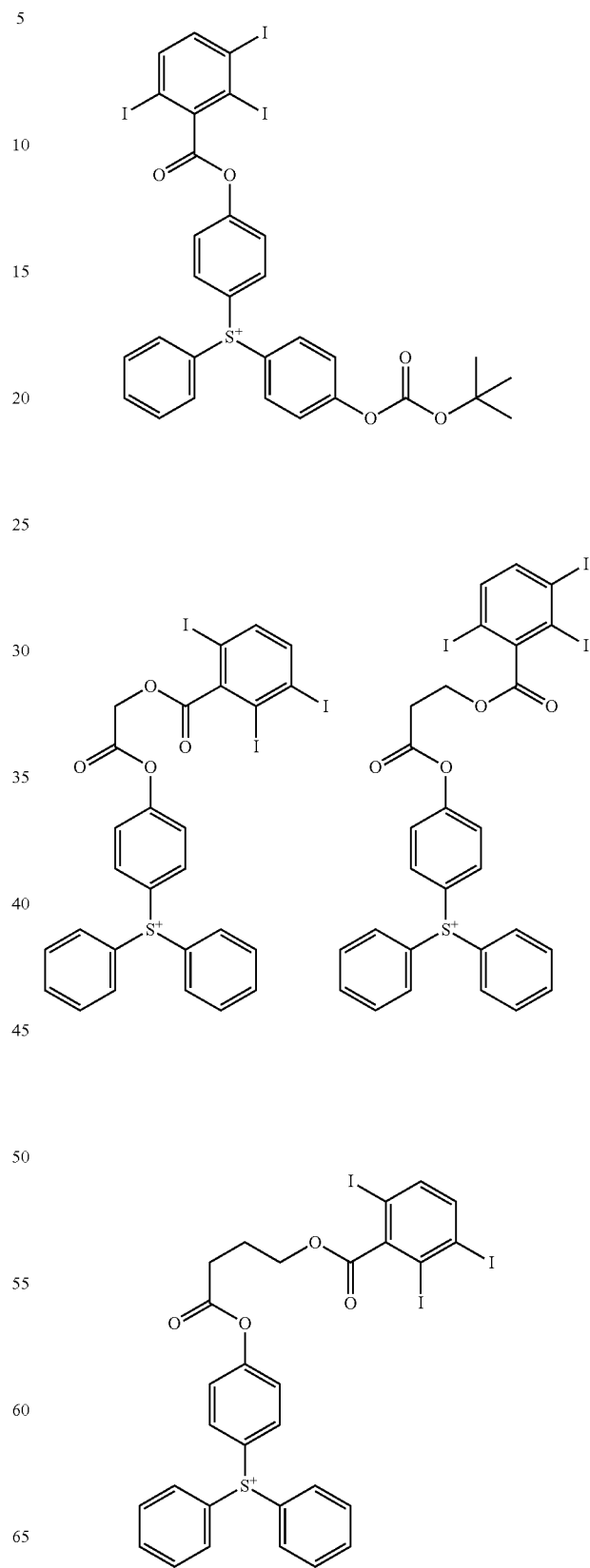

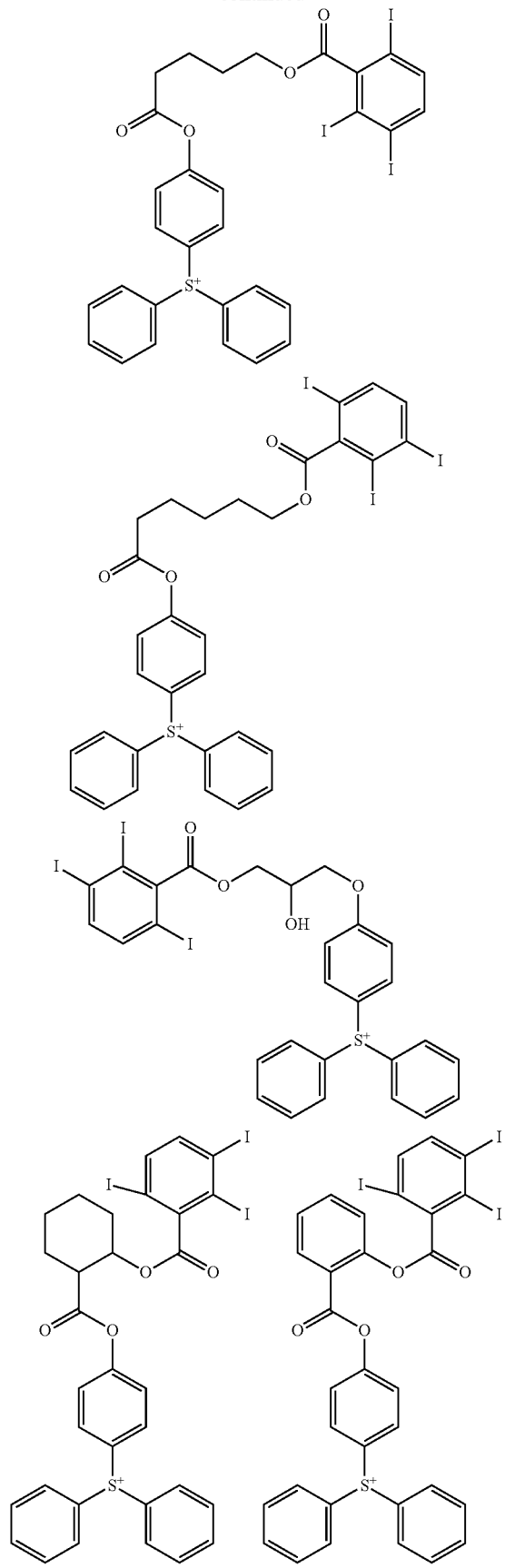

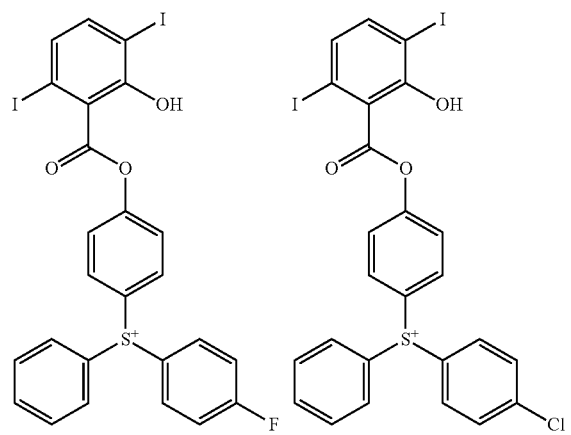
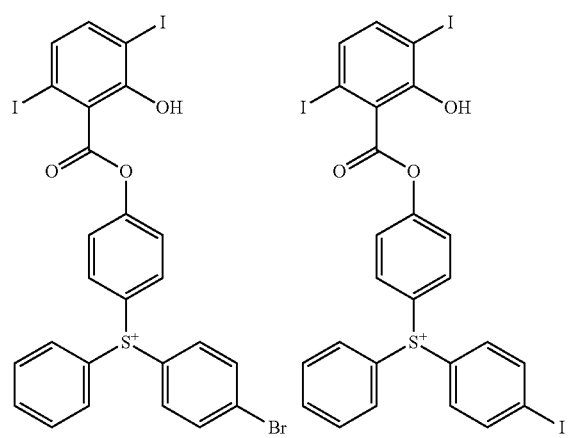
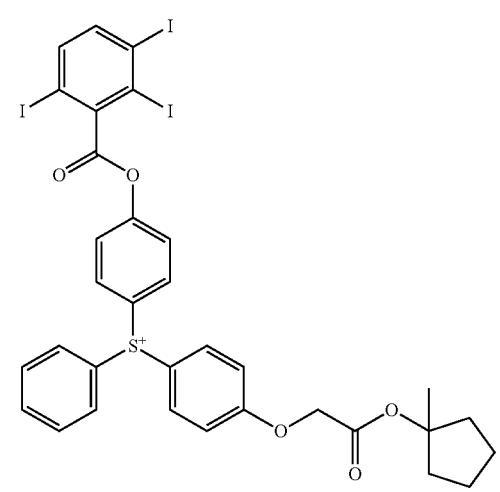
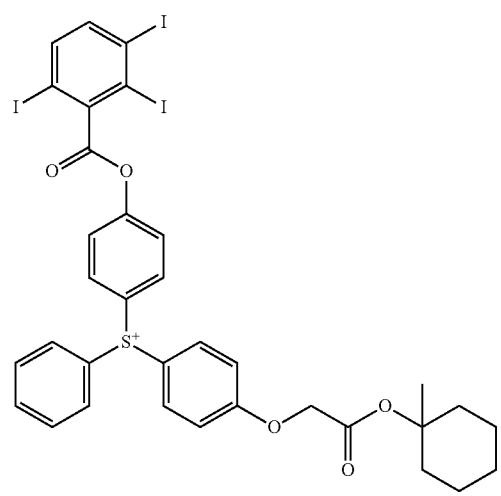
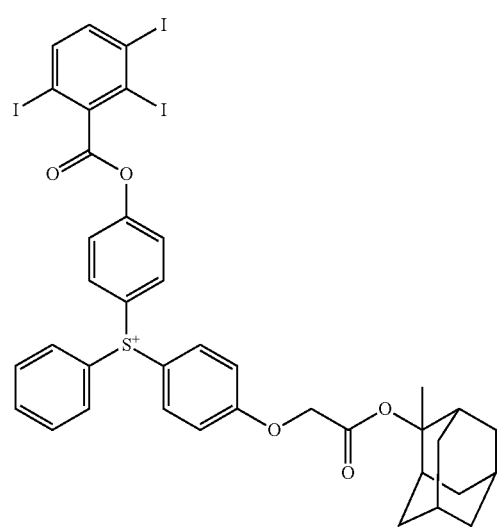
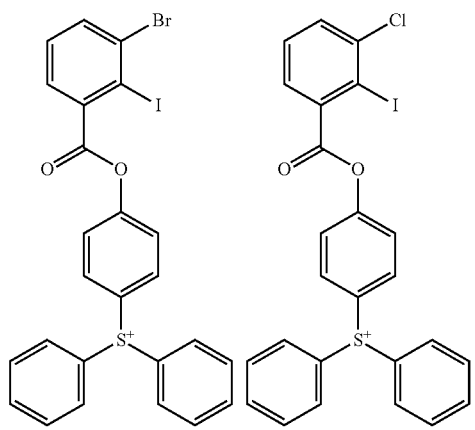

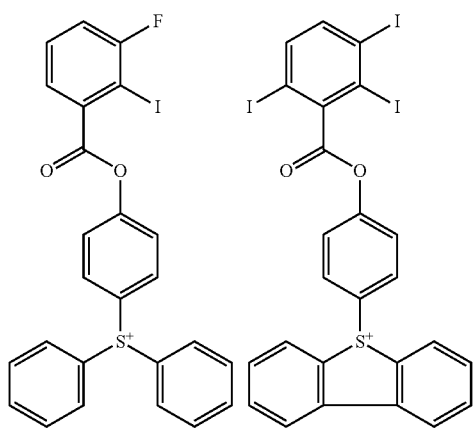
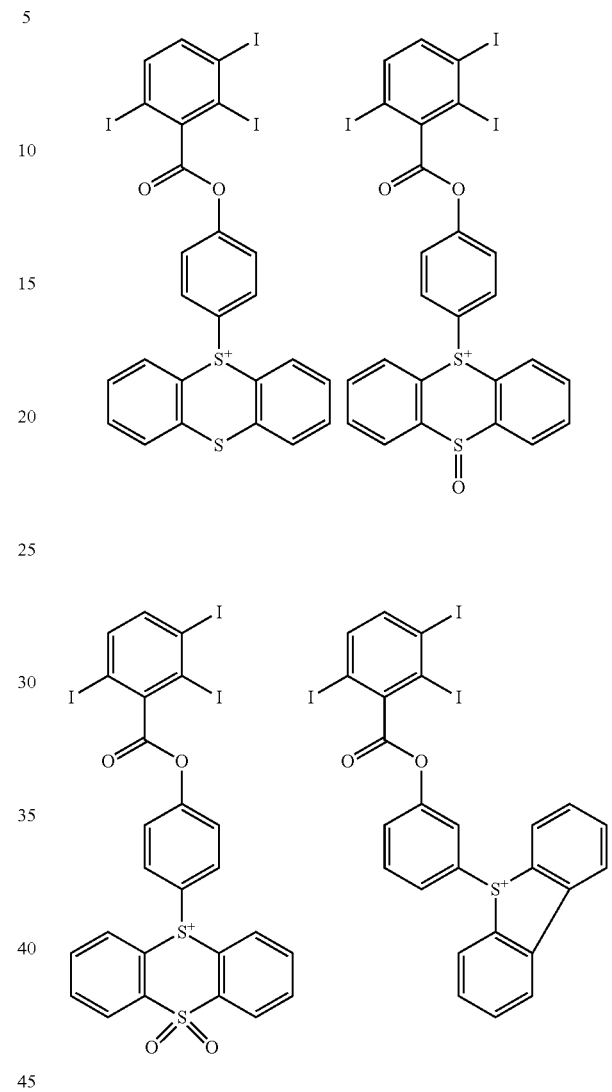
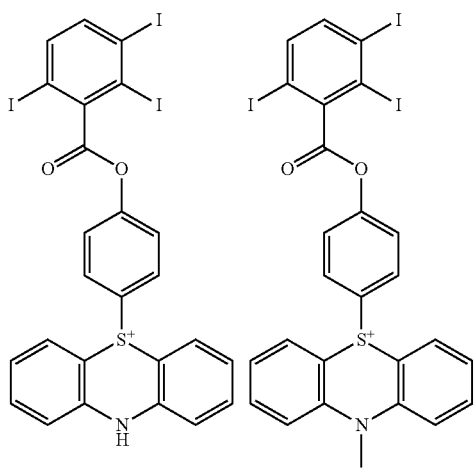

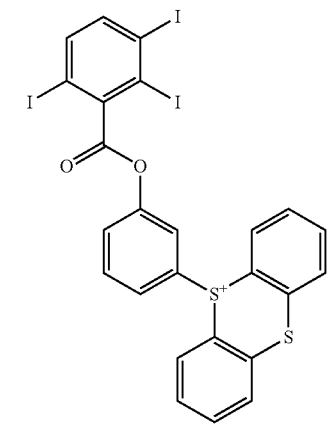
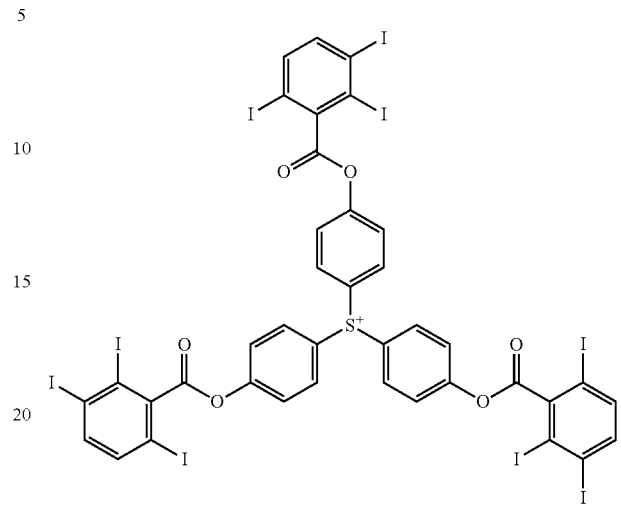
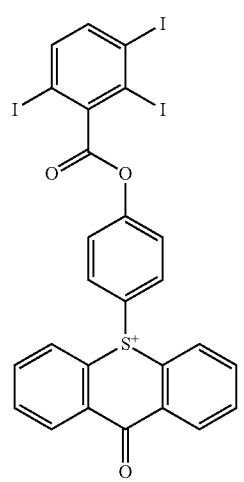
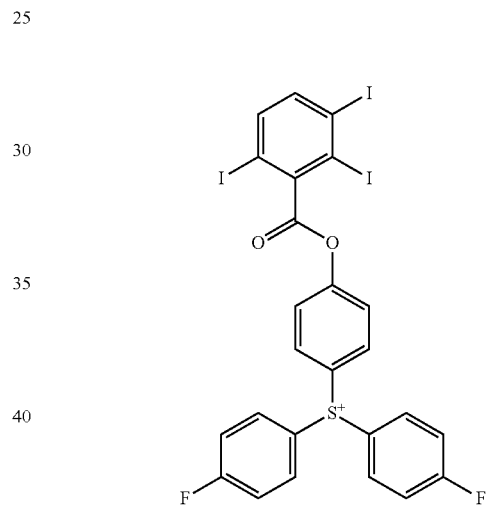
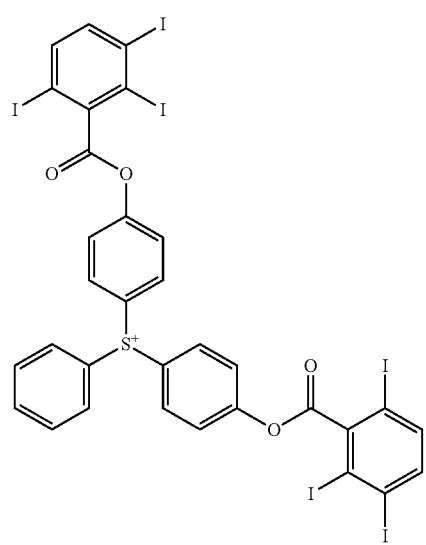
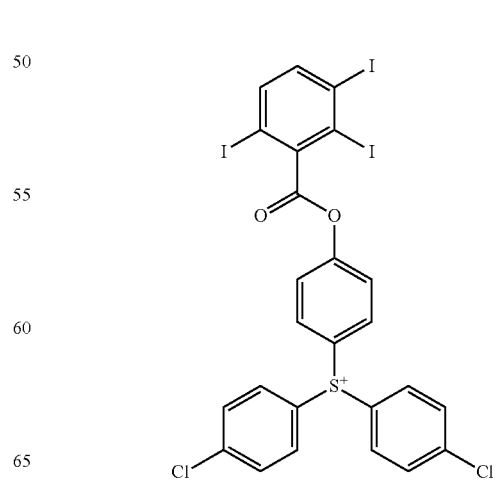

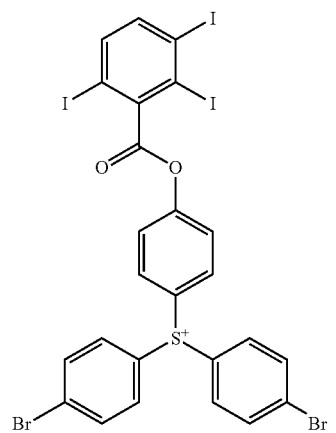
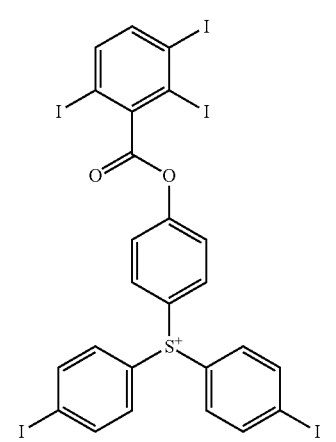
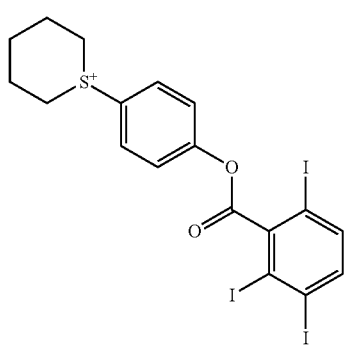
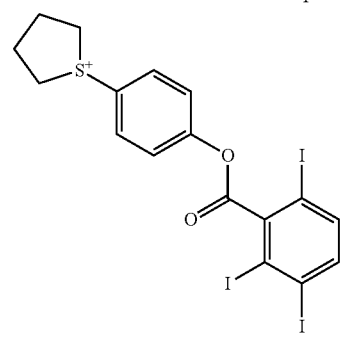
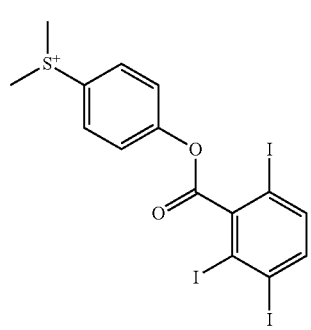
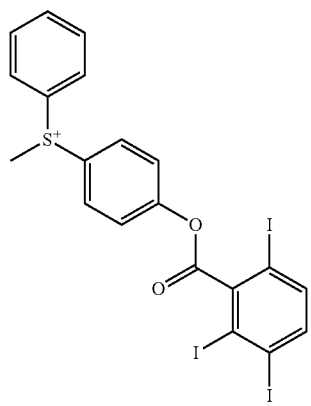
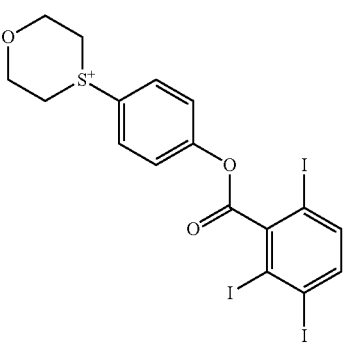
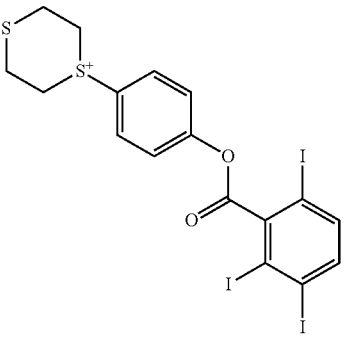

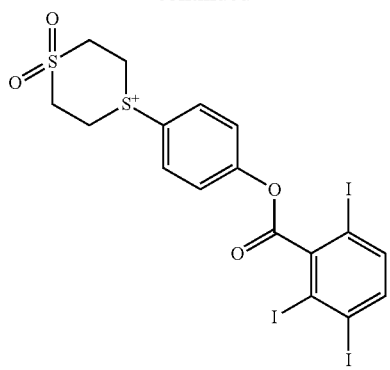
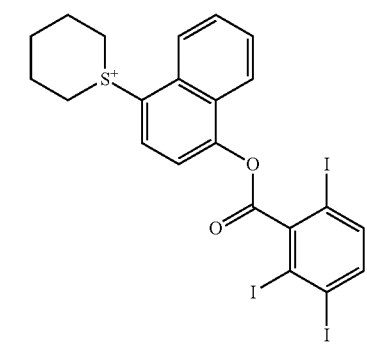
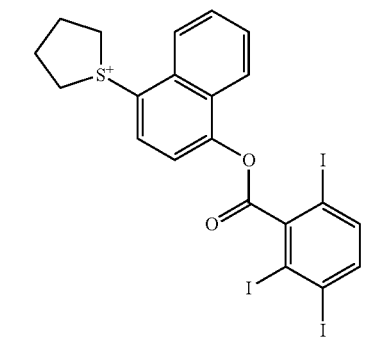
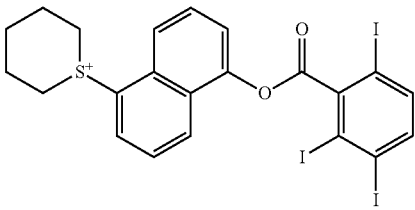
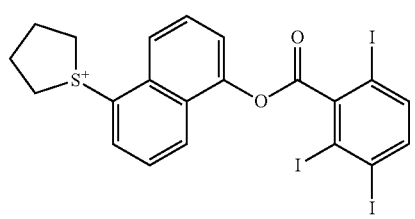
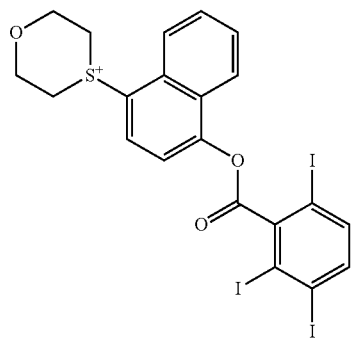
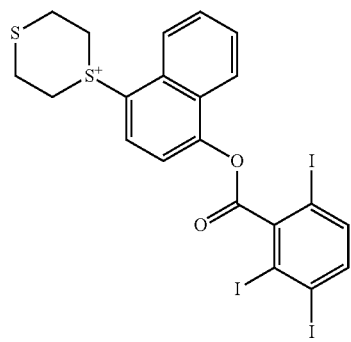
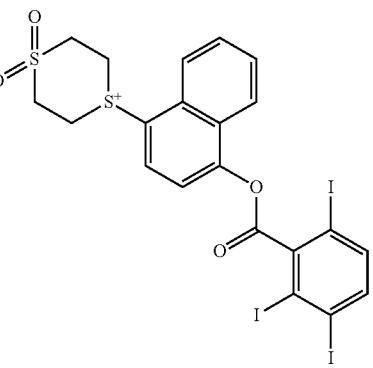
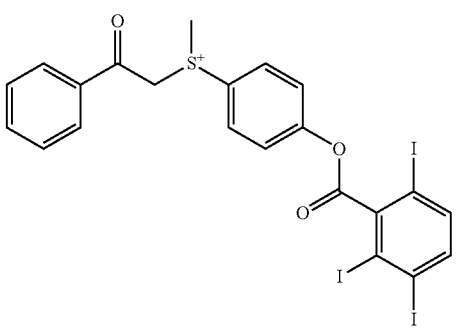

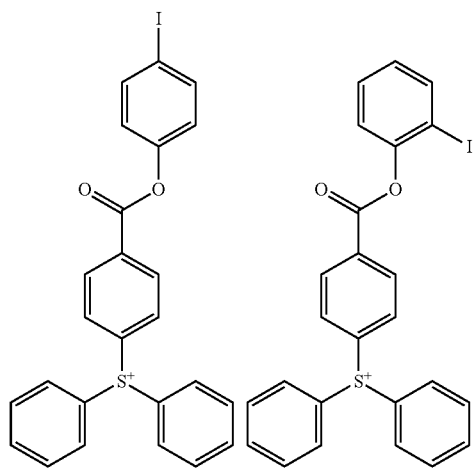
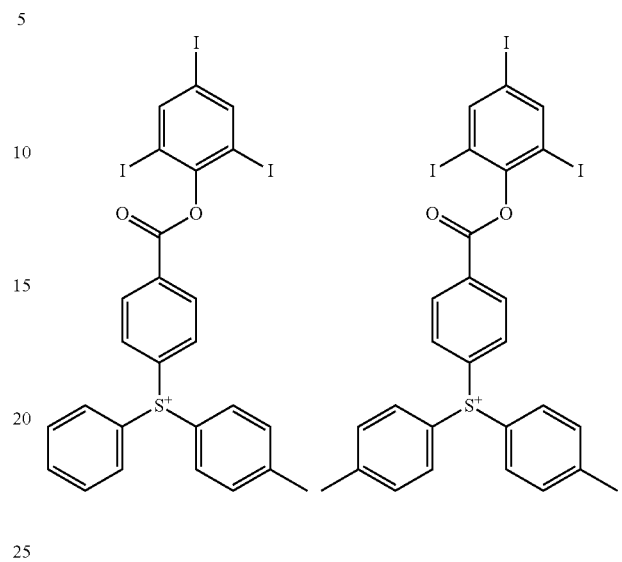
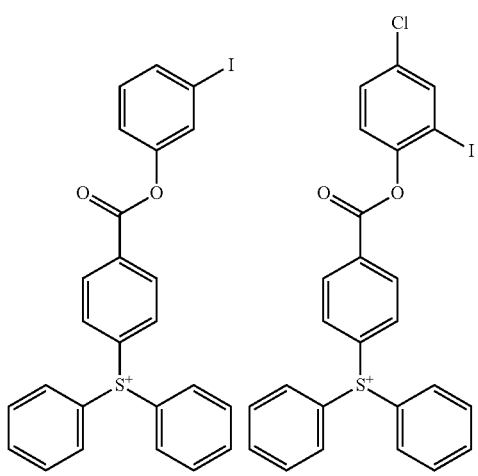
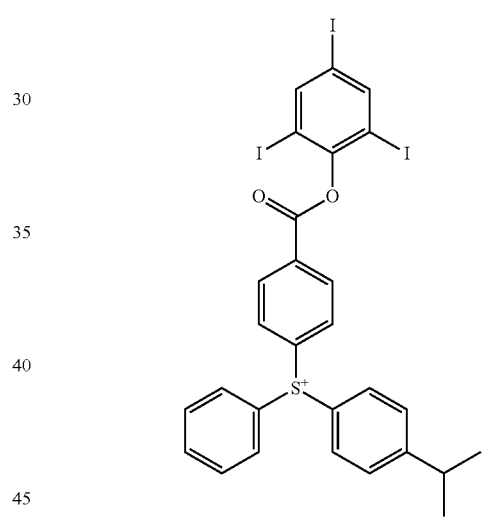
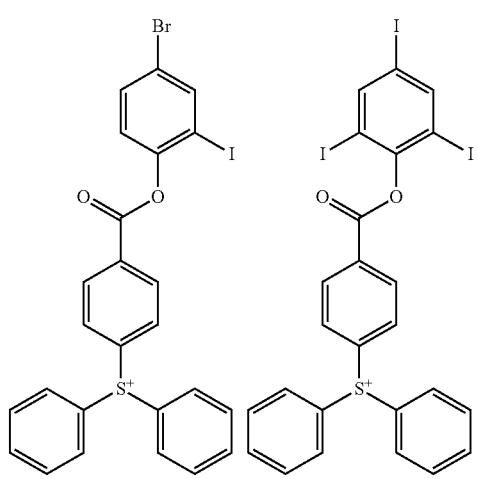
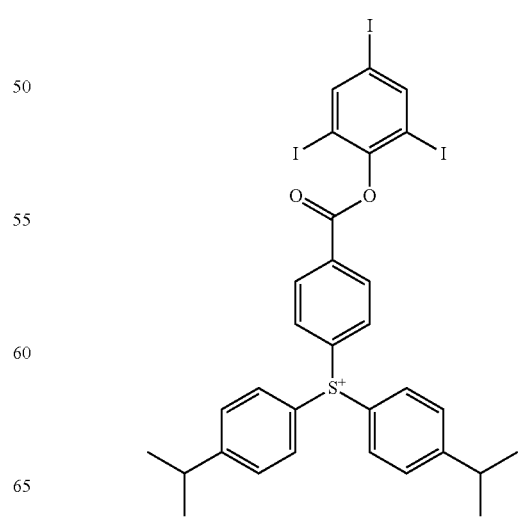

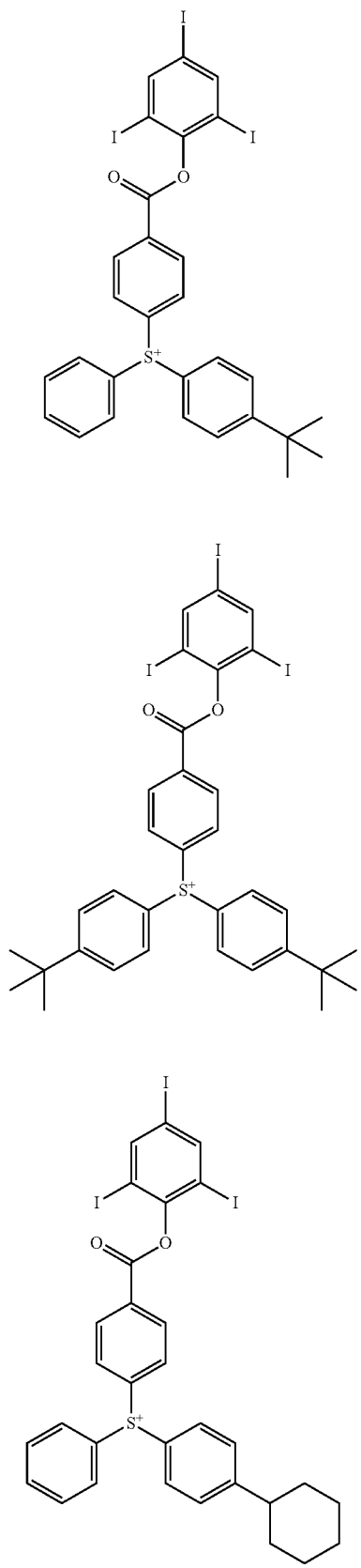
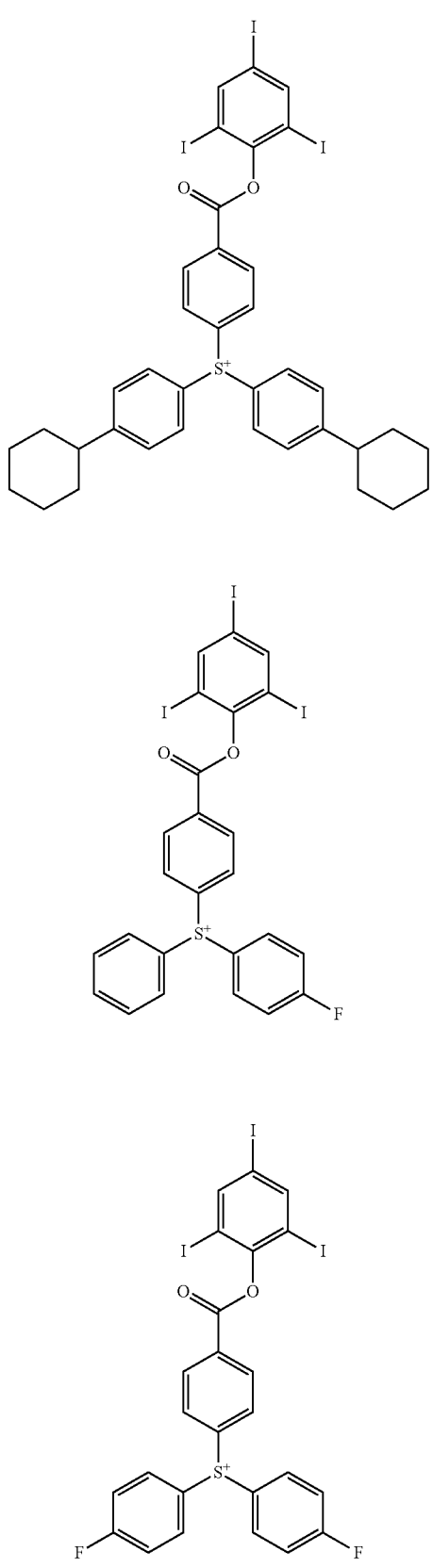 [SMILES: O=C(Oc1c(I)cc(I)cc1I)c1ccc([S+](c2ccc(C3CCCCC3)cc2)c2ccc(C3CCCCC3)cc2)cc1 ; O=C(Oc1c(I)cc(I)cc1I)c1ccc([S+](c2ccccc2)c2ccc(F)cc2)cc1 ; O=C(Oc1c(I)cc(I)cc1I)c1ccc([S+](c2ccc(F)cc2)c2ccc(F)cc2)cc1]

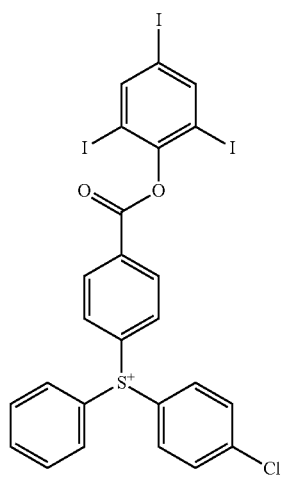
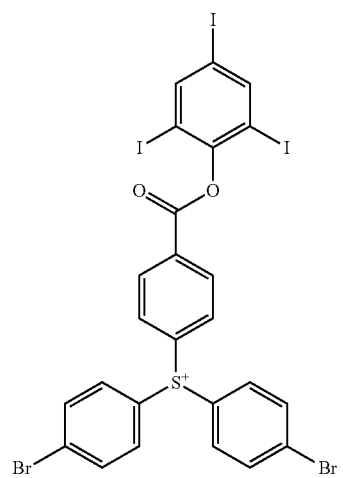
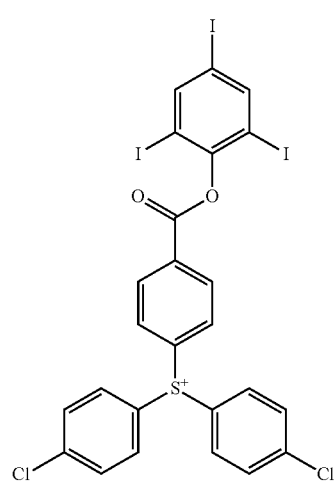
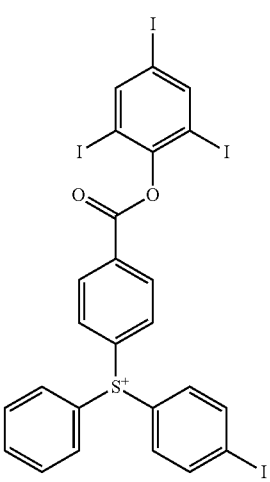
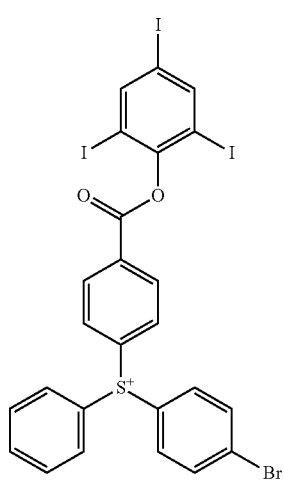
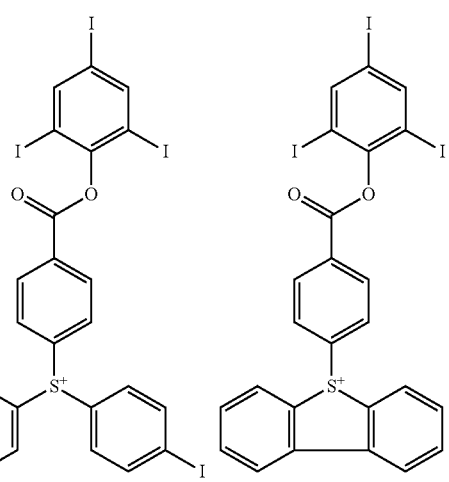

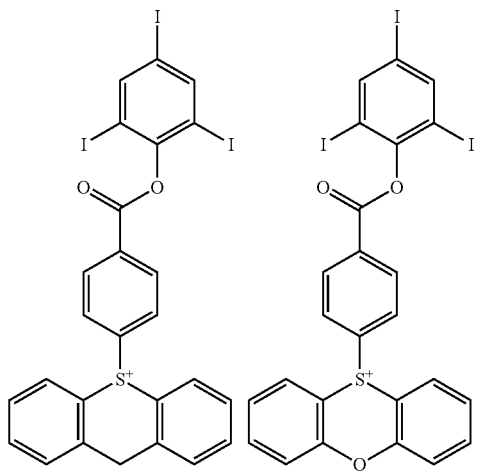
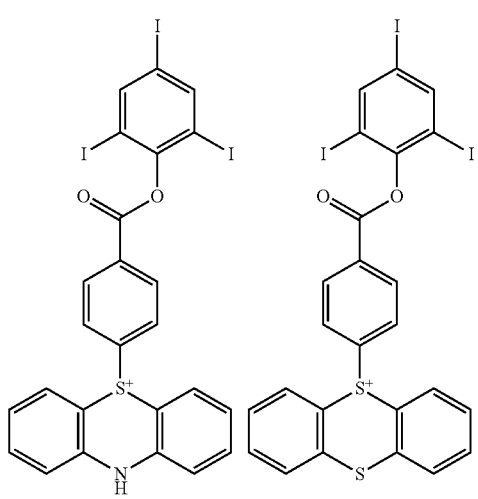
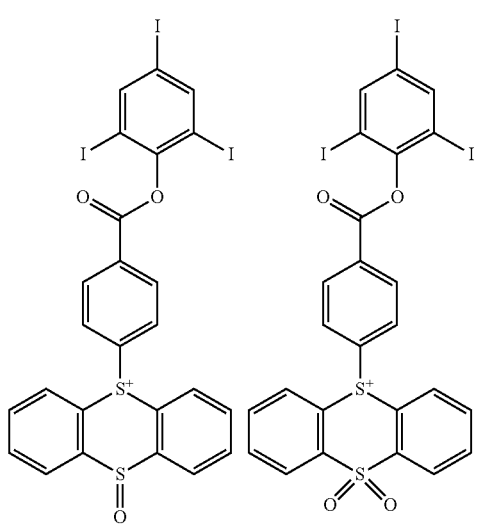
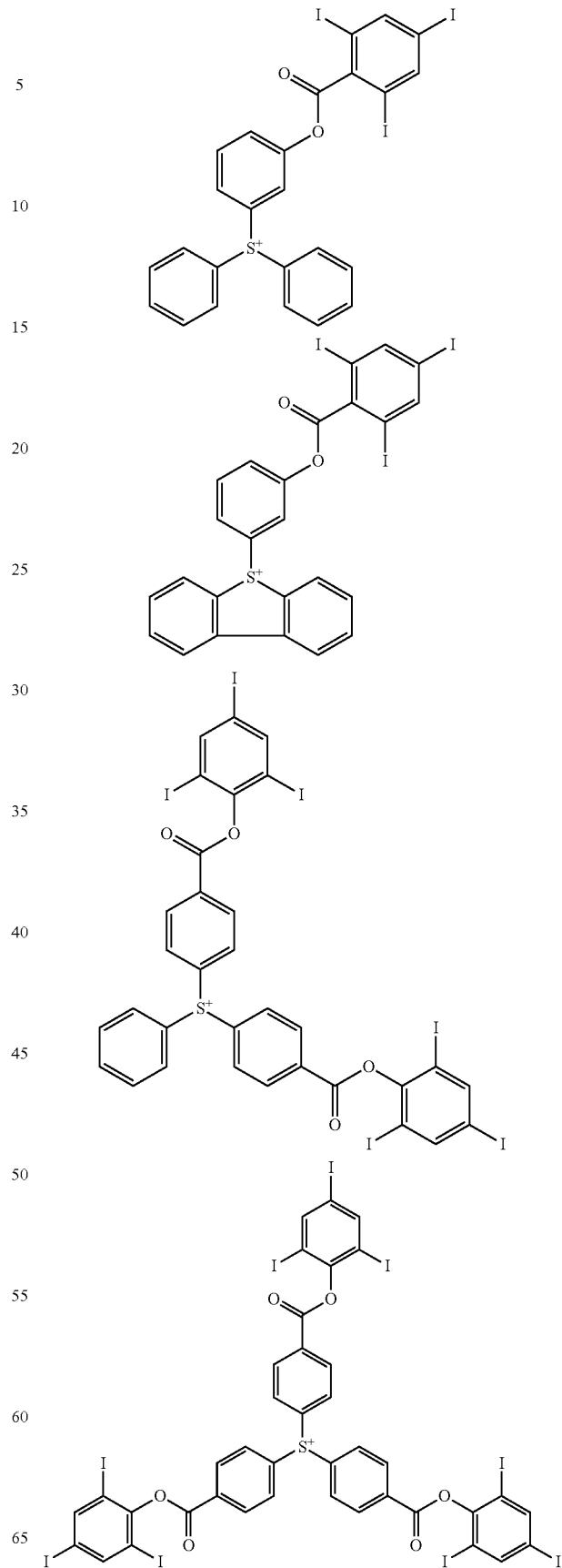

-continued
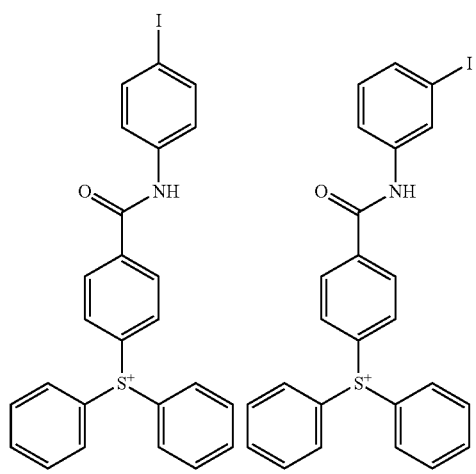
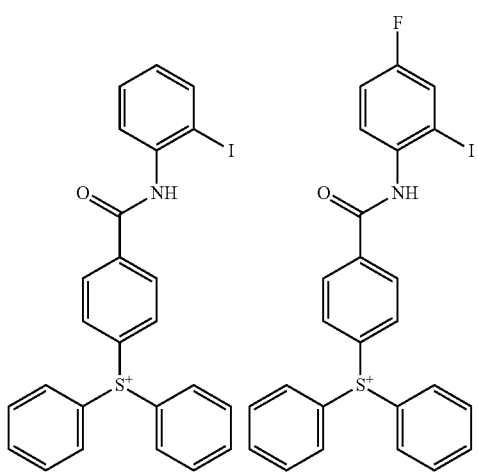
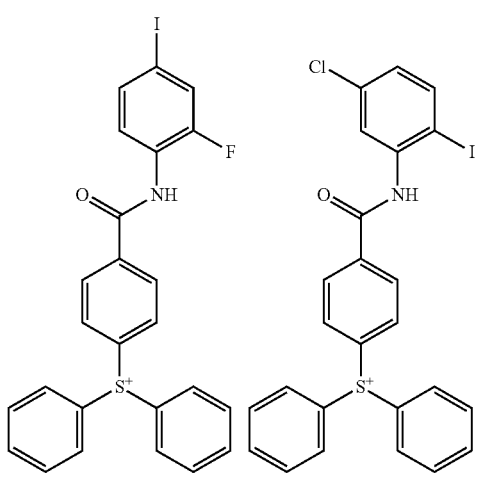
-continued
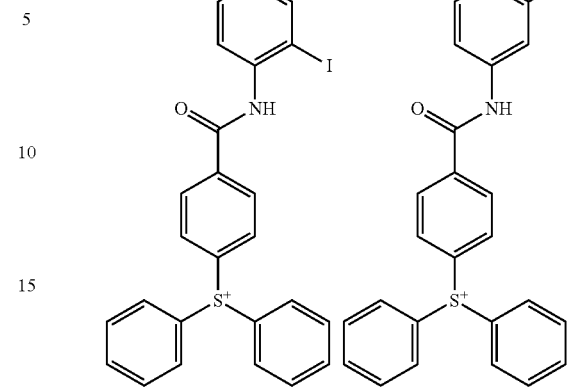
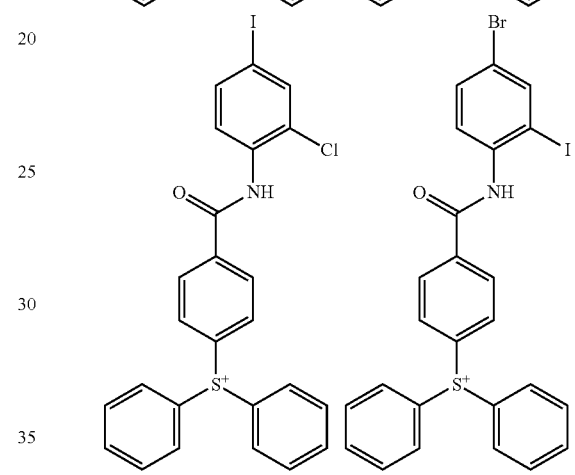
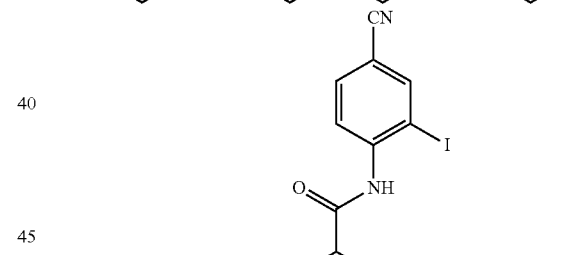
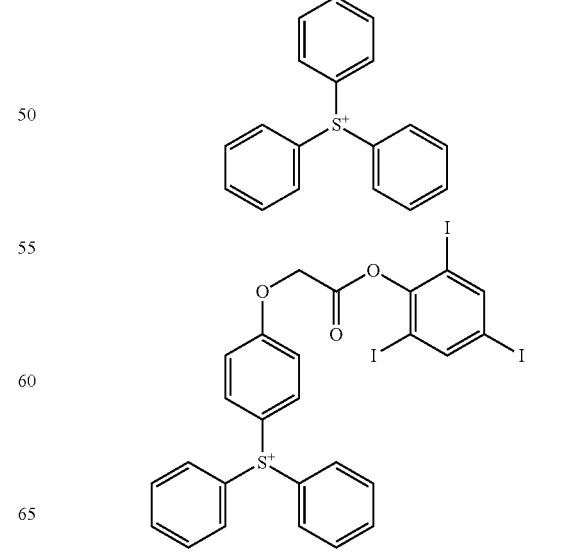

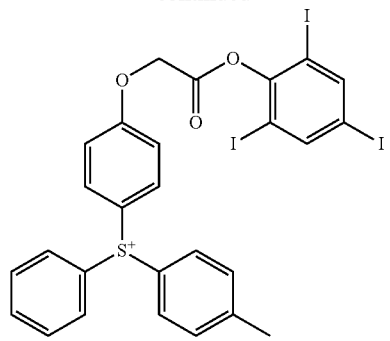
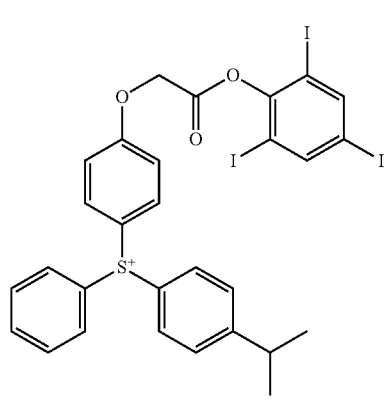
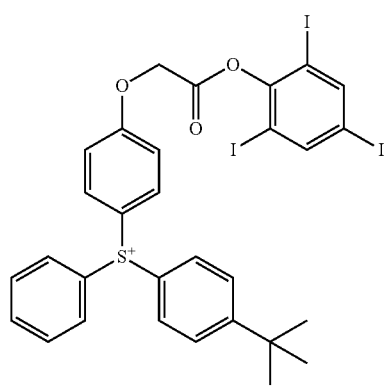
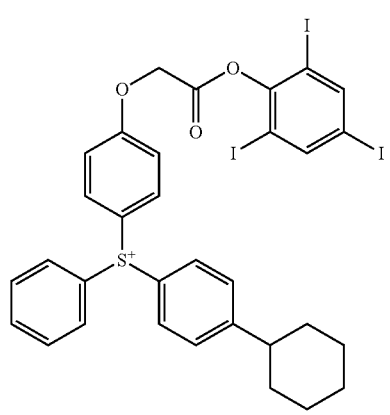
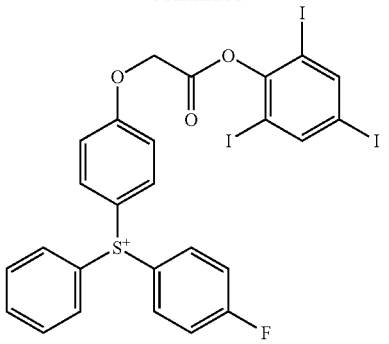
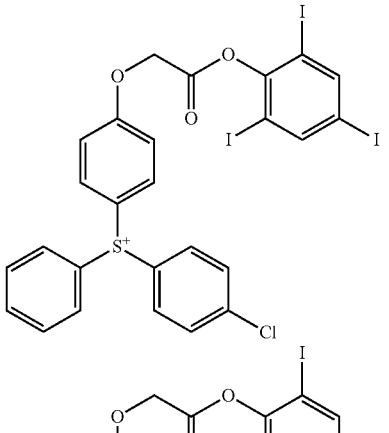
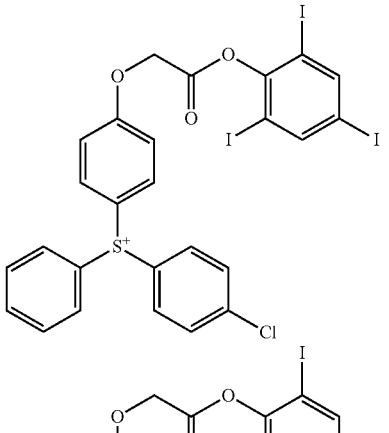
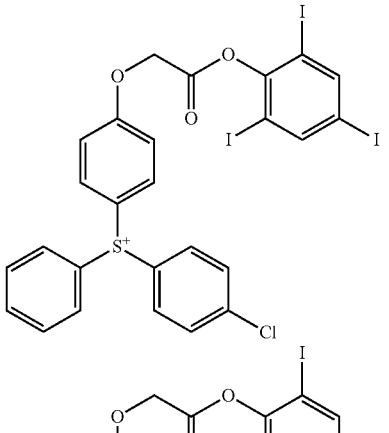
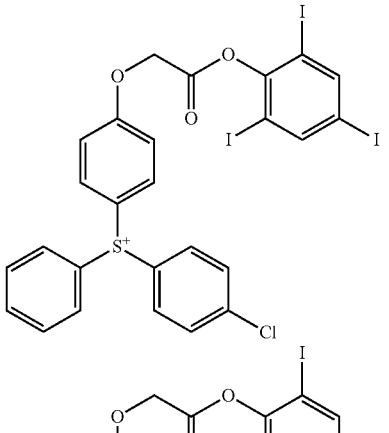
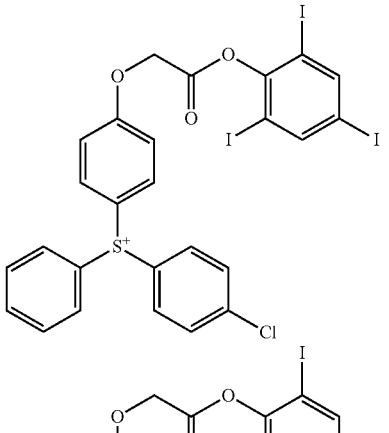

41
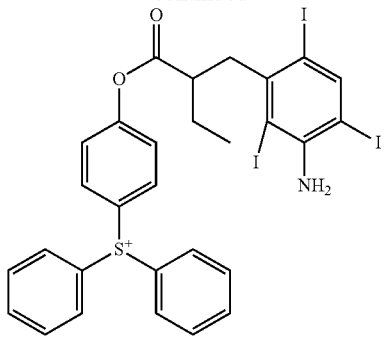
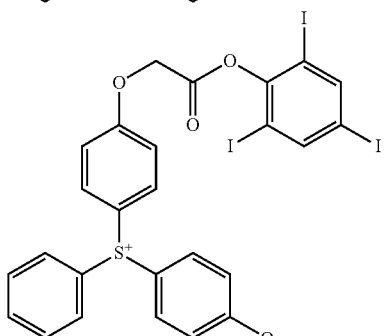
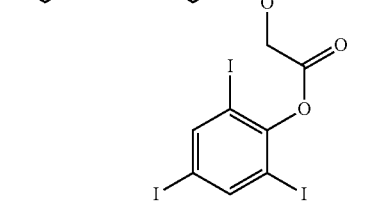
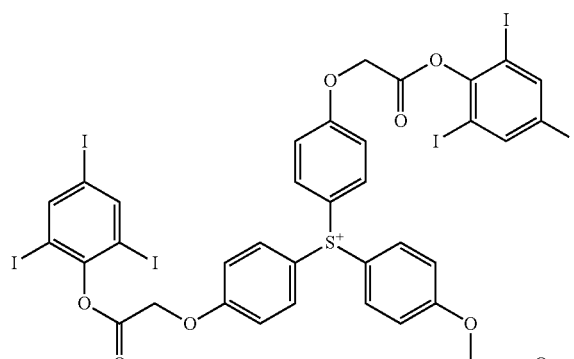
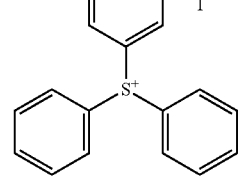
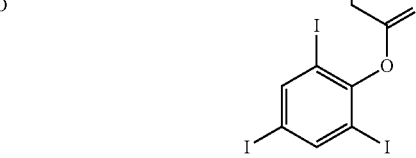
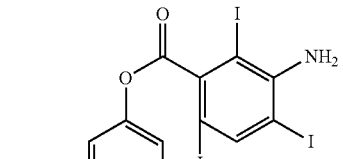
42
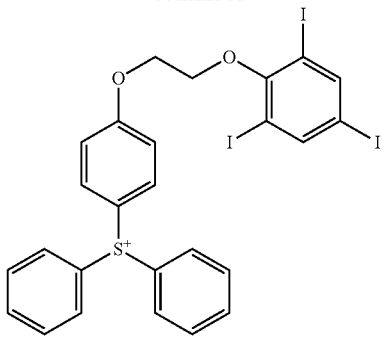
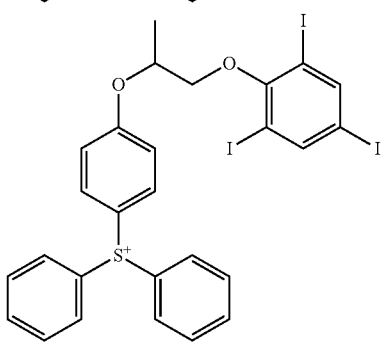
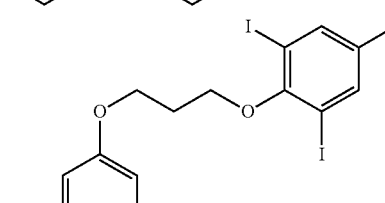
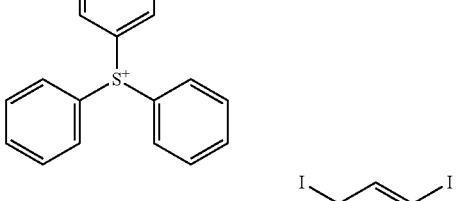
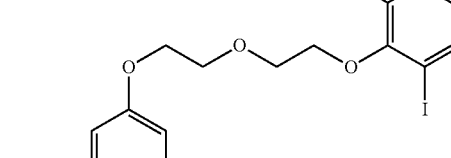
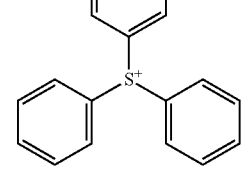
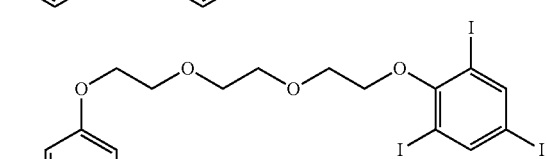
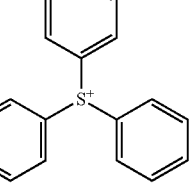

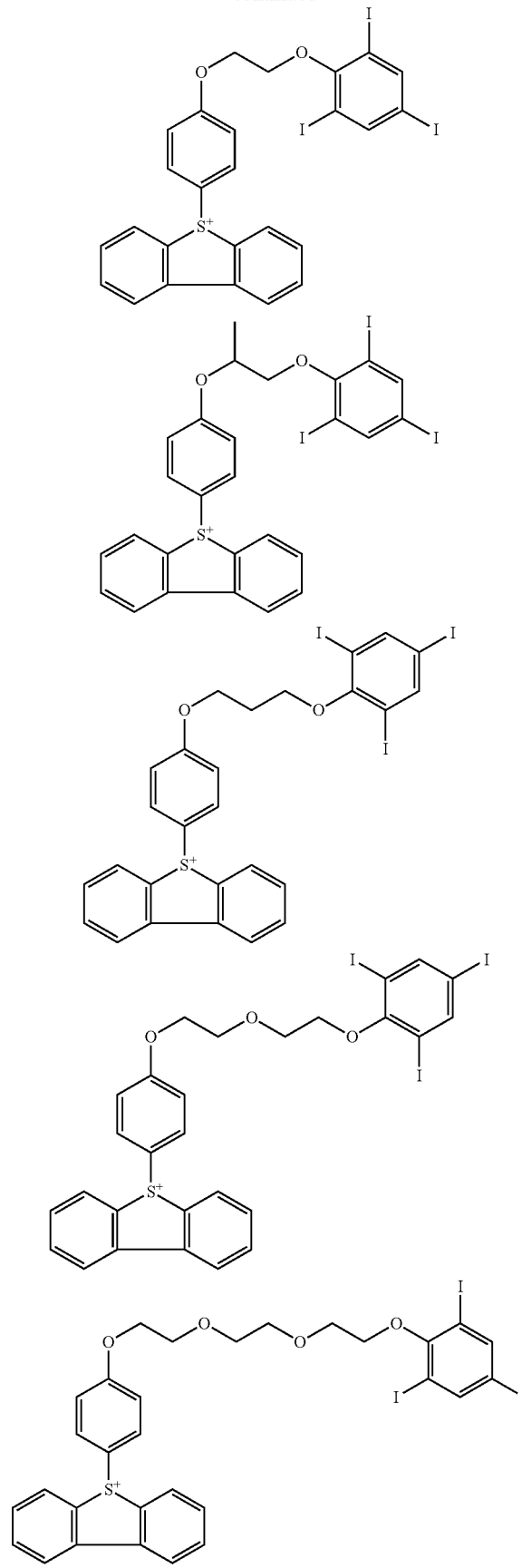
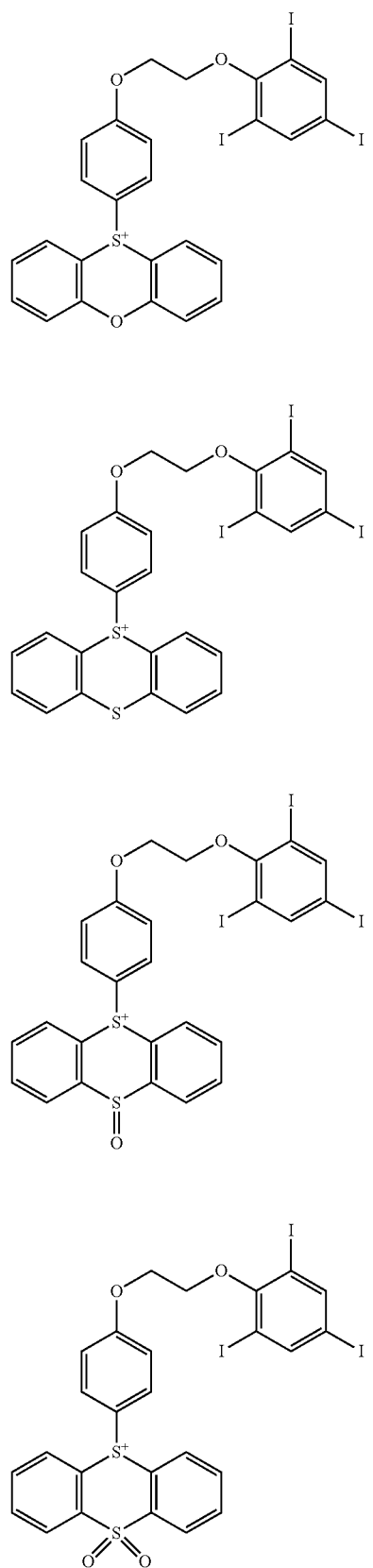

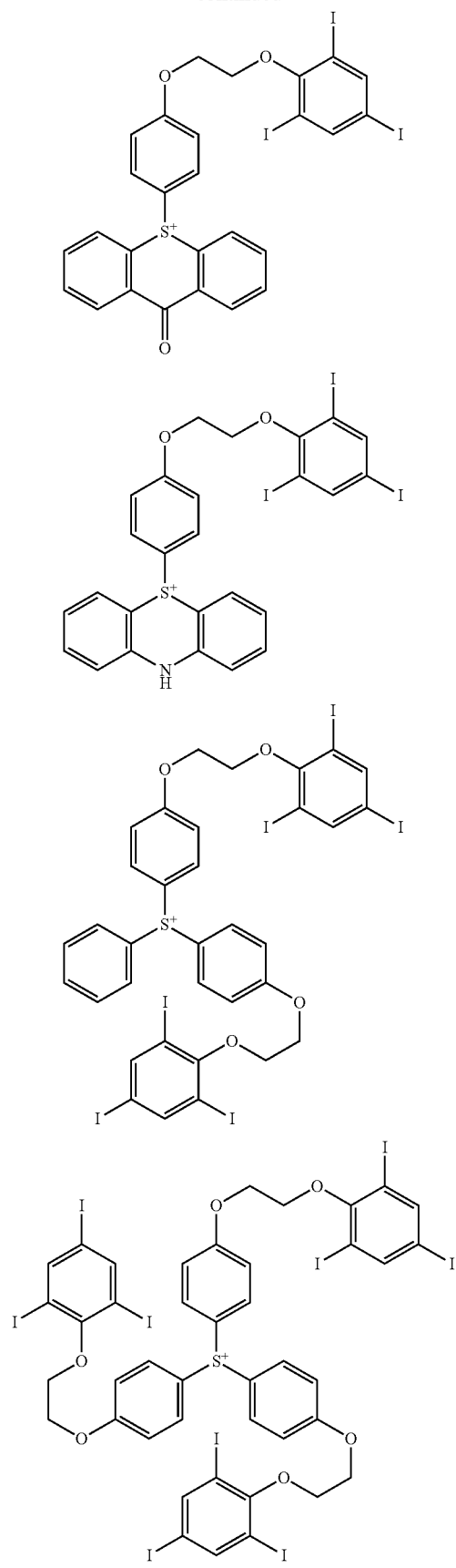

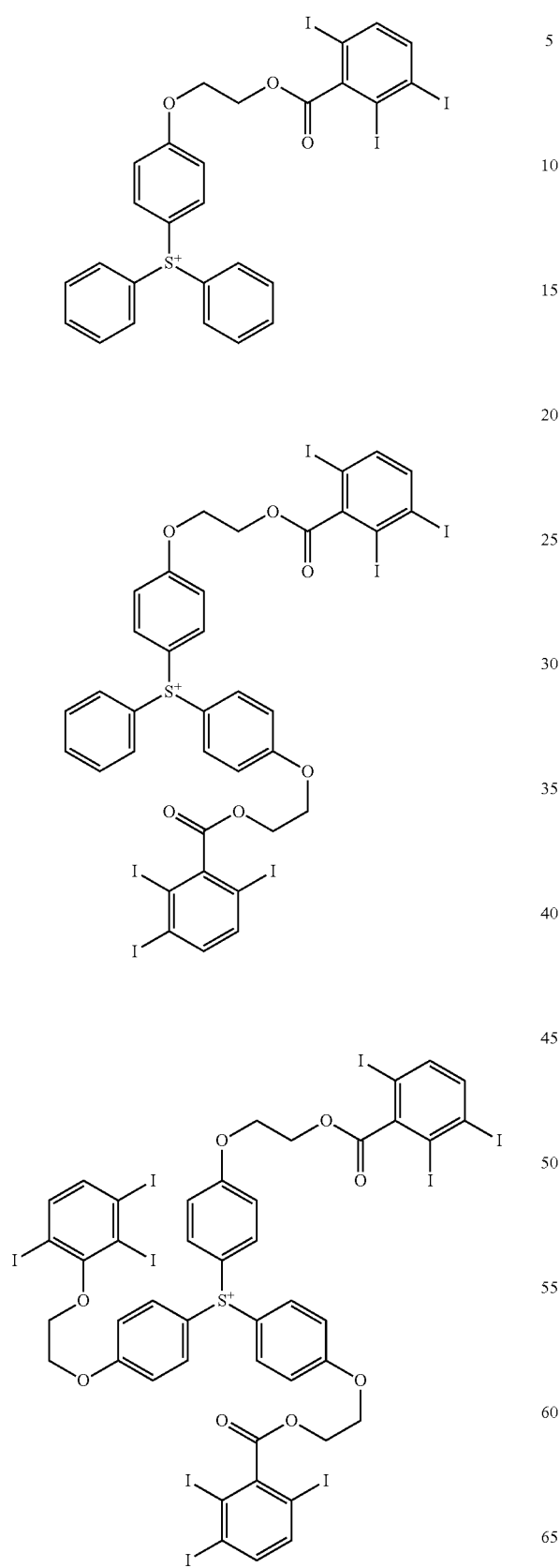
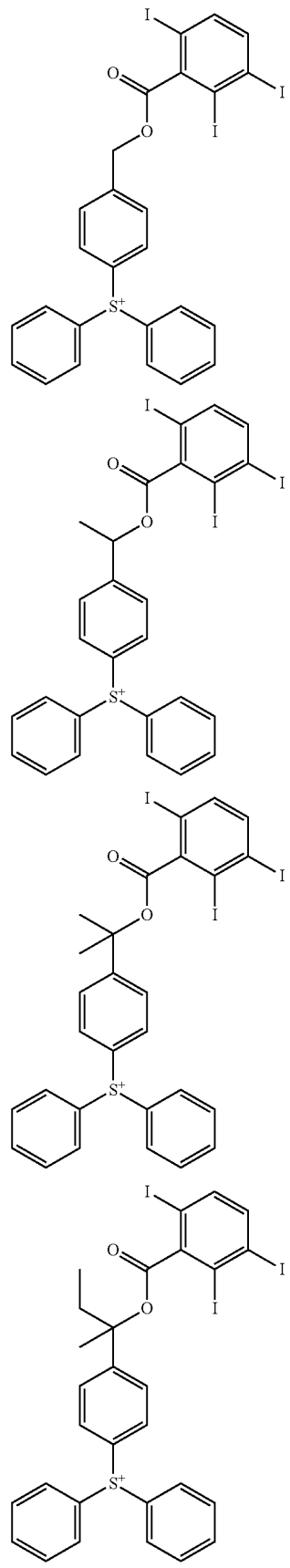

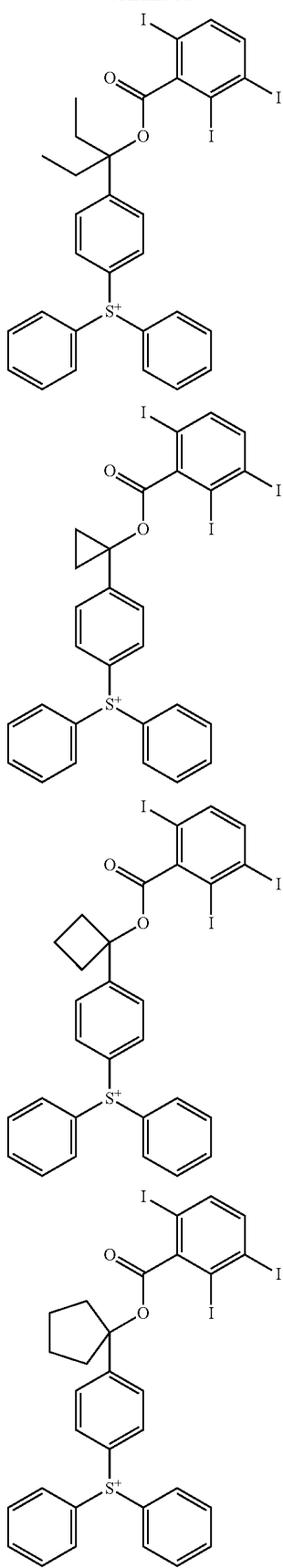

51
-continued
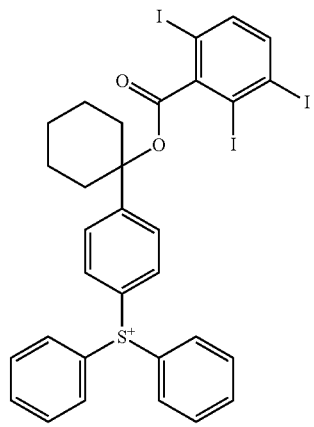
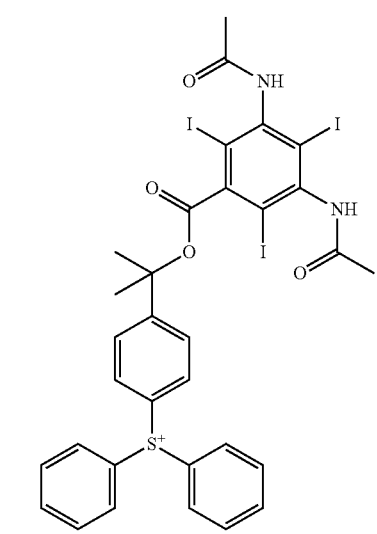
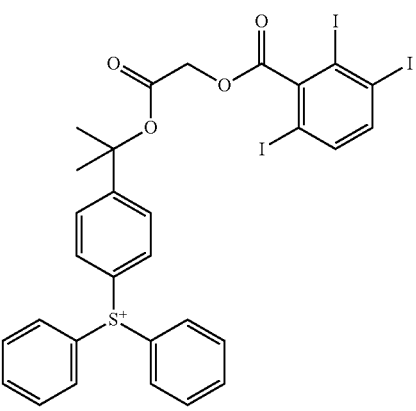
52
-continued
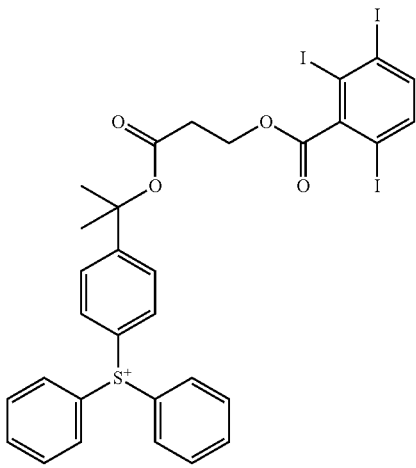
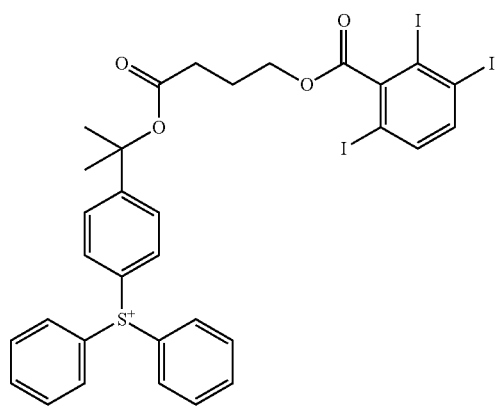
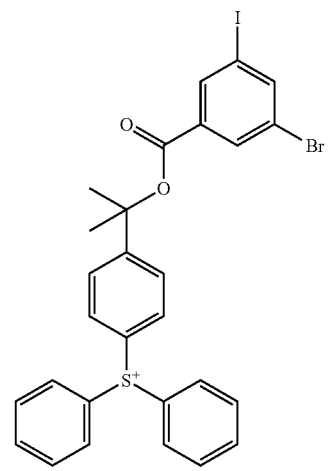

-continued
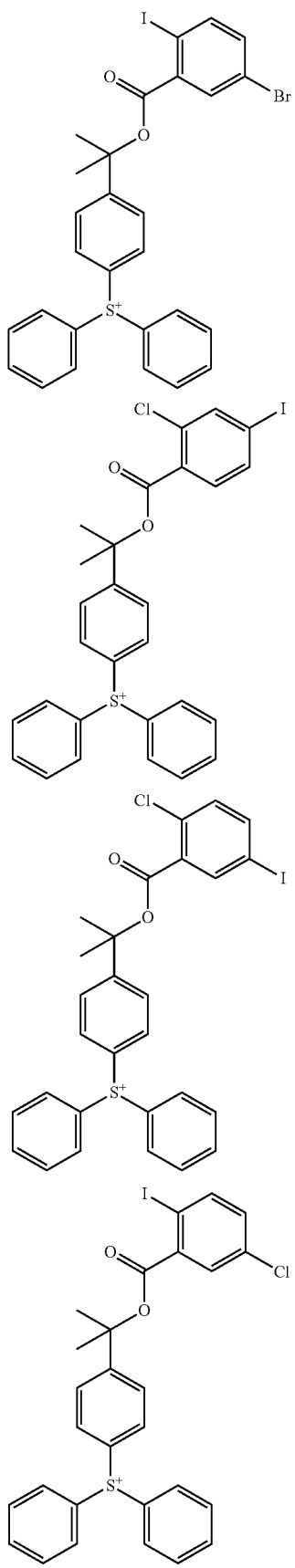
-continued
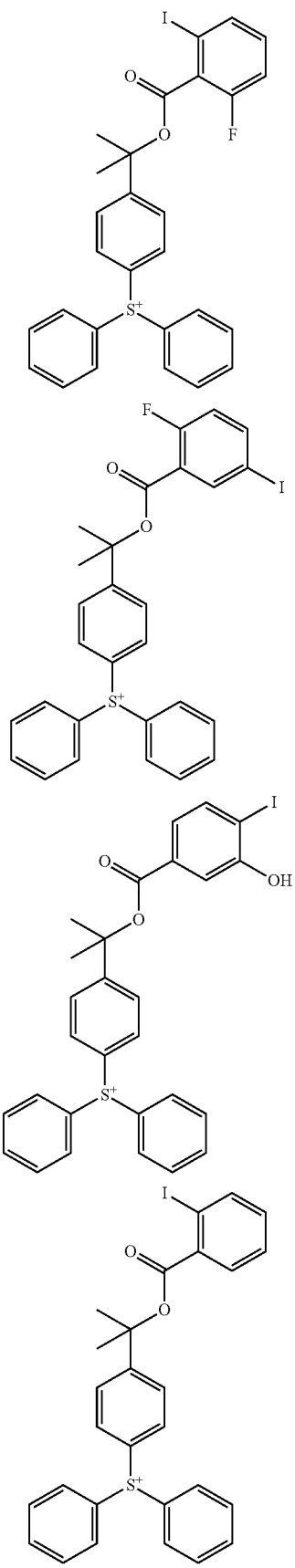

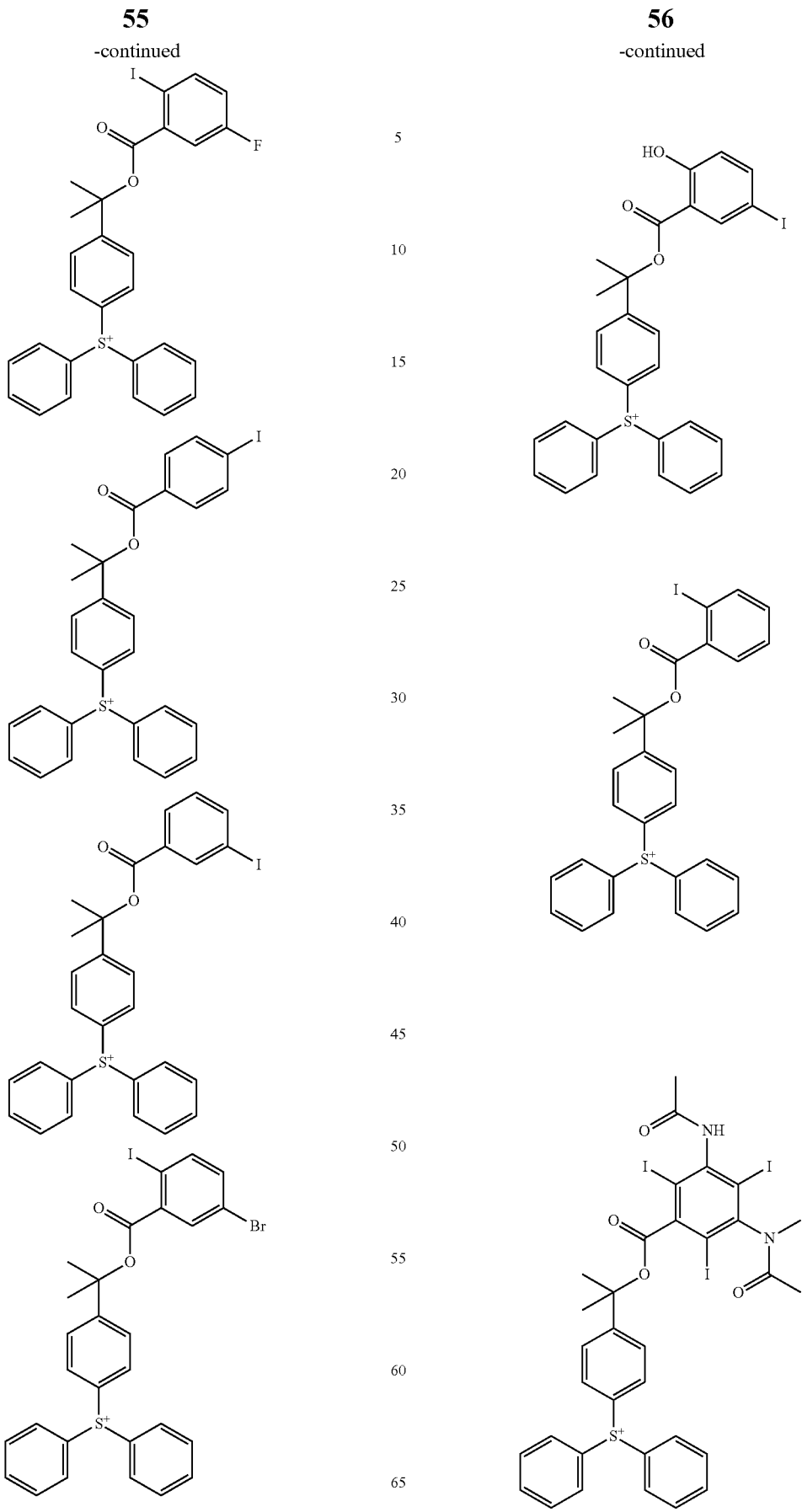

-continued
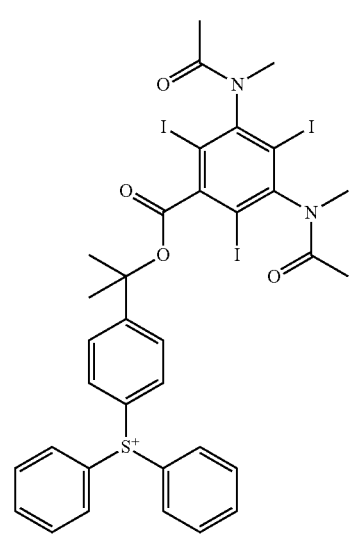
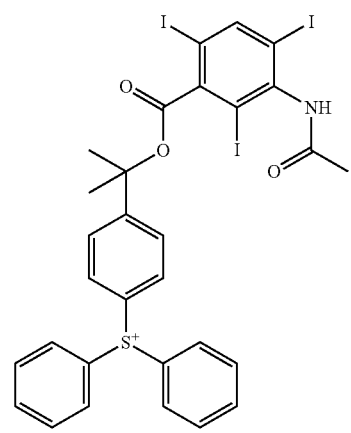
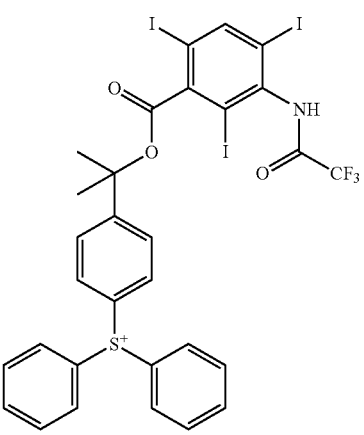
-continued
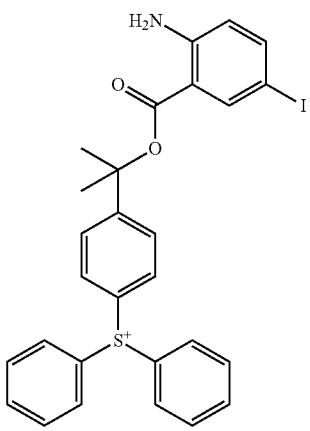
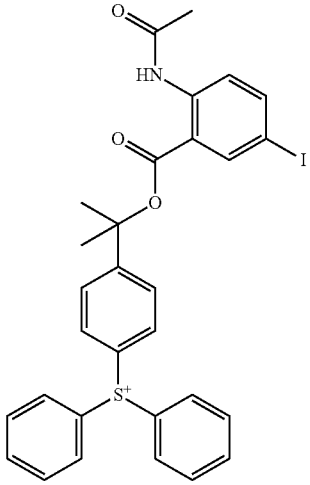
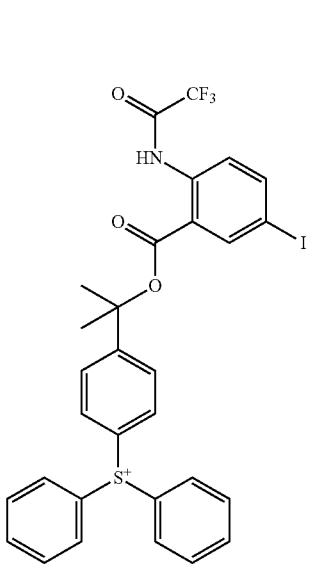

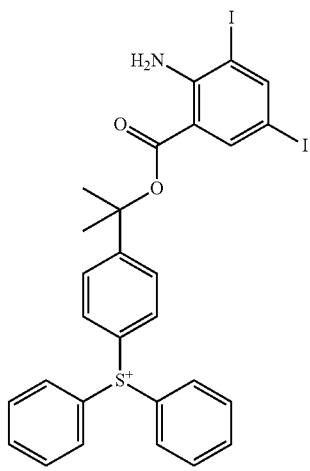
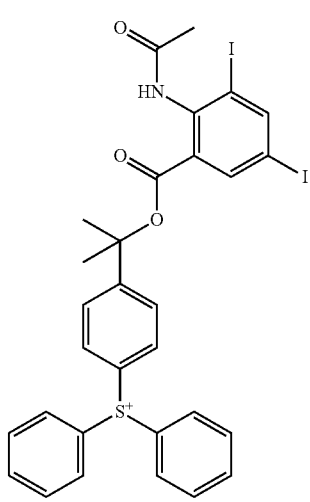
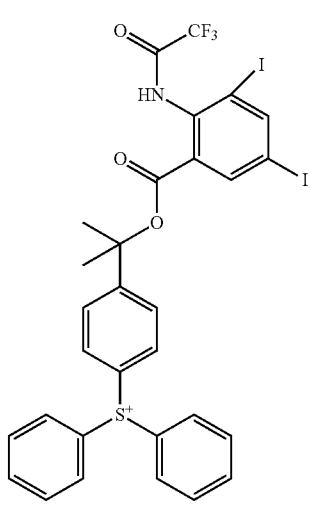
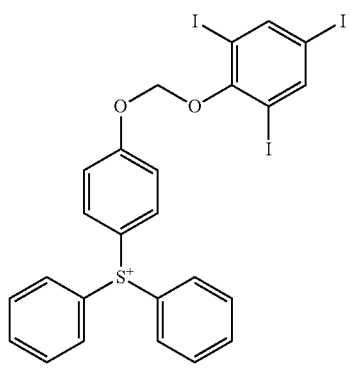
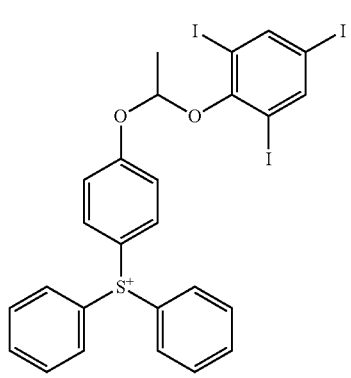
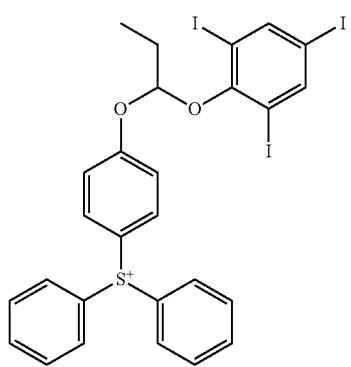

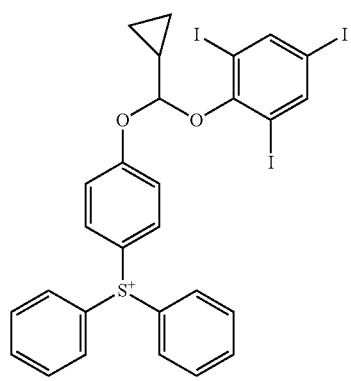
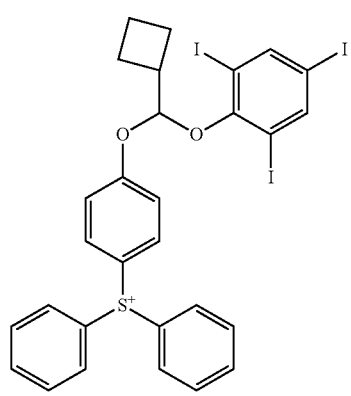
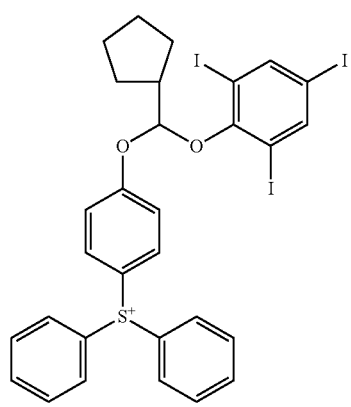
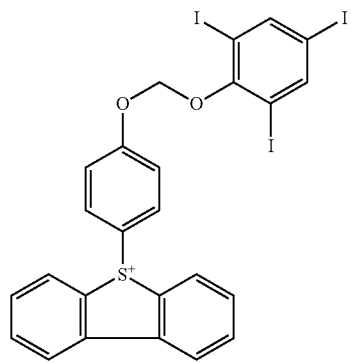
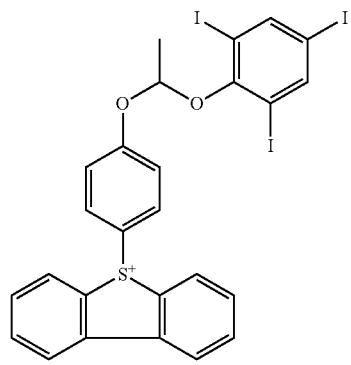
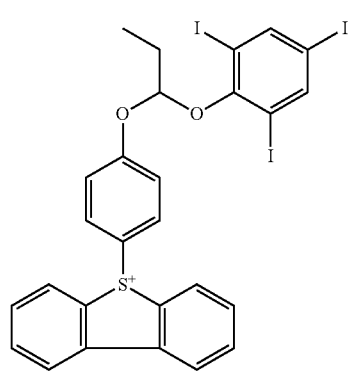
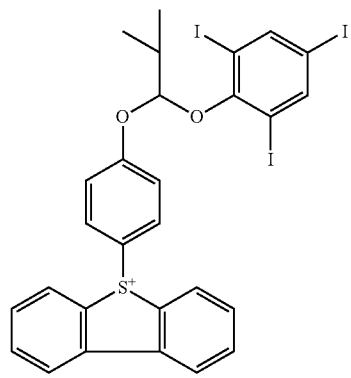
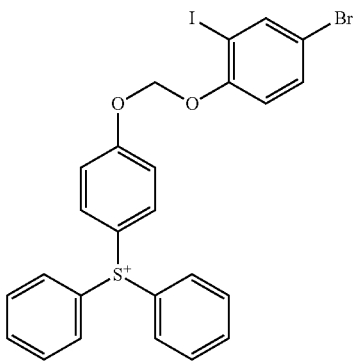

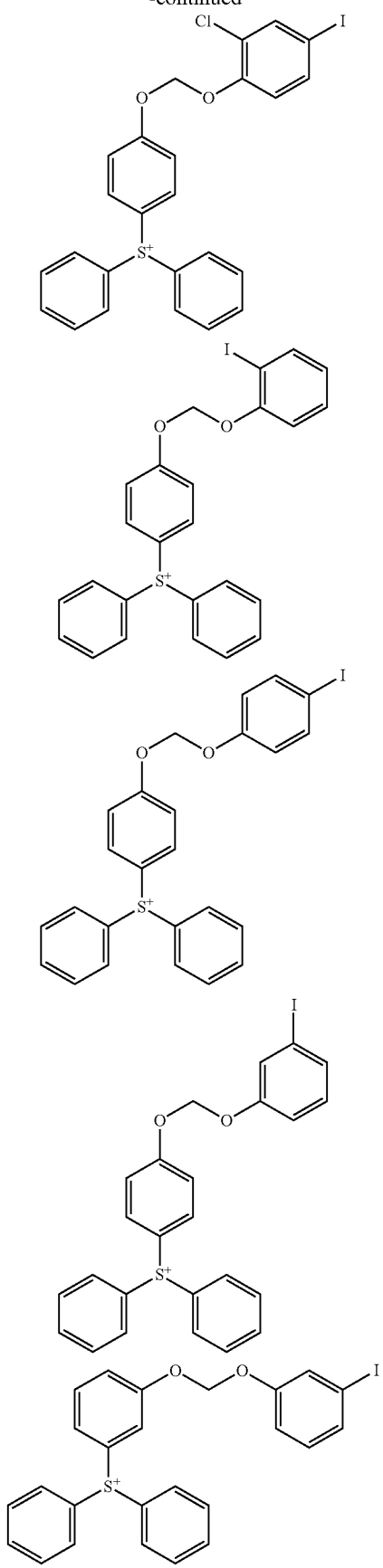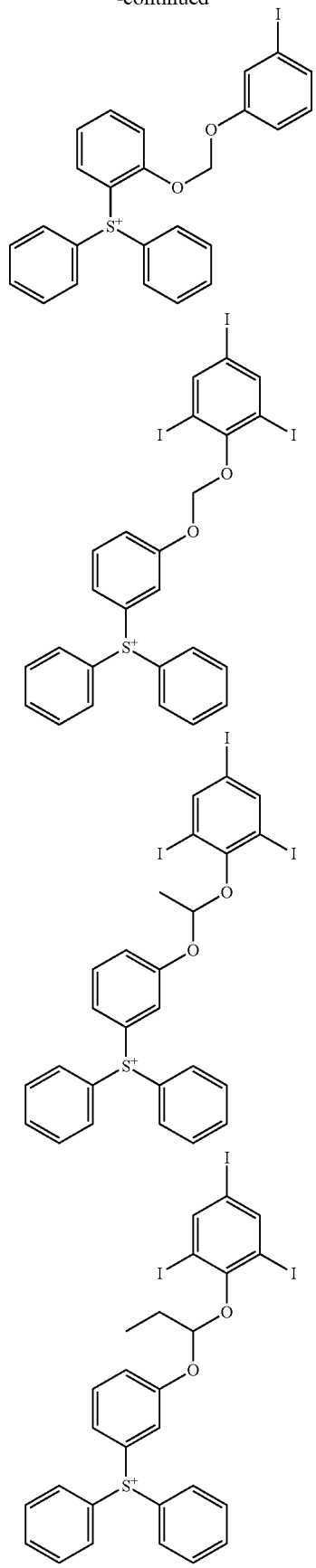

-continued

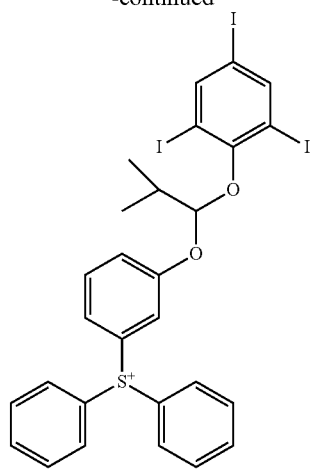

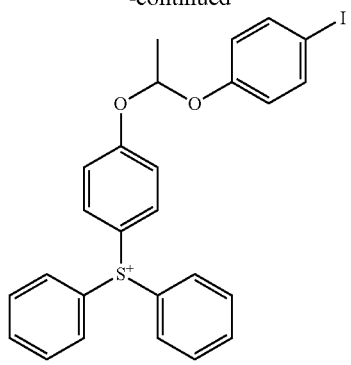

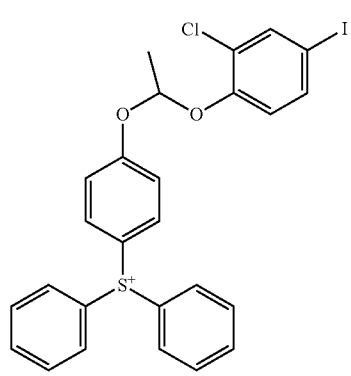

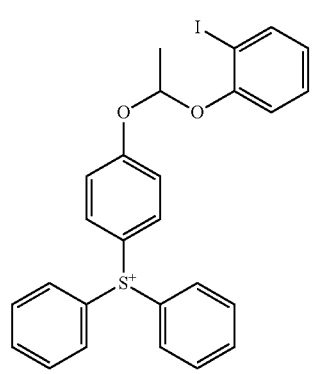

The sulfonium salt having formula (1) may be synthesized, for example, by subjecting a benzene ring-bearing sulfonium salt to esterification, etherification, amidation or acetal reaction on its benzene ring using an iodized benzoic acid, phenol, aniline or vinyl ether compound.

A resist composition comprising the sulfonium salt having formula (1) according to the invention may be processed to form a pattern even when it does not contain a base polymer. The sulfonium salt may be blended with a base polymer. In this embodiment, it is preferred from the aspects of sensitivity and acid diffusion suppressing effect that the amount of the sulfonium salt having formula (1) be 0.01 to 1,000 parts by weight, more preferably 0.05 to 500 parts by weight per 100 parts by weight of the base polymer.

Base Polymer

Where the resist composition is of positive tone, the resist composition comprises a base polymer comprising recurring units containing an acid labile group, preferably recurring units having the formula (a1) or recurring units having the formula (a2). These units are simply referred to as recurring units (a1) and (a2), hereinafter.

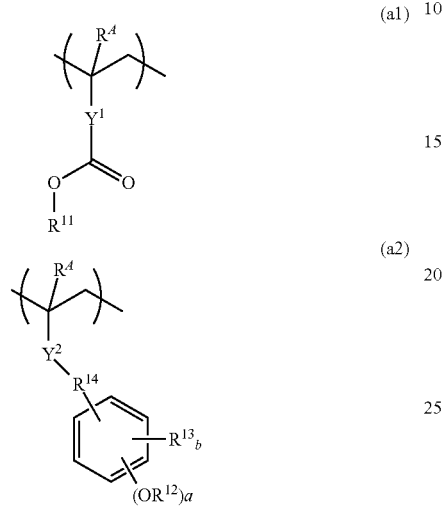

In formulae (a1) and (a2), $R^A$ is each independently hydrogen or methyl. $Y^1$ is a single bond, phenylene group, naphthylene group, or a $C_1$-$C_{12}$ linking group containing an ester bond or lactone ring. $Y^2$ is a single bond or ester bond. $R^{11}$ and $R^{12}$ each are an acid labile group. $R^{13}$ is fluorine, trifluoromethyl, cyano, a $C_1$-$C_6$ alkyl group, $C_1$-$C_6$ alkoxy group, $C_2$-$C_7$ acyl group, $C_2$-$C_7$ acyloxy group, or $C_2$-$C_7$ alkoxycarbonyl group. $R^{14}$ is a single bond or a $C_1$-$C_6$ straight or branched alkanediyl group in which some carbon may be replaced by an ether bond or ester bond, a is 1 or 2, b is an integer of 0 to 4, the sum of a+b is 1 to 5.

Examples of the monomer from which recurring units (a1) are derived are shown below, but not limited thereto. Herein $R^A$ and $R^{11}$ are as defined above.

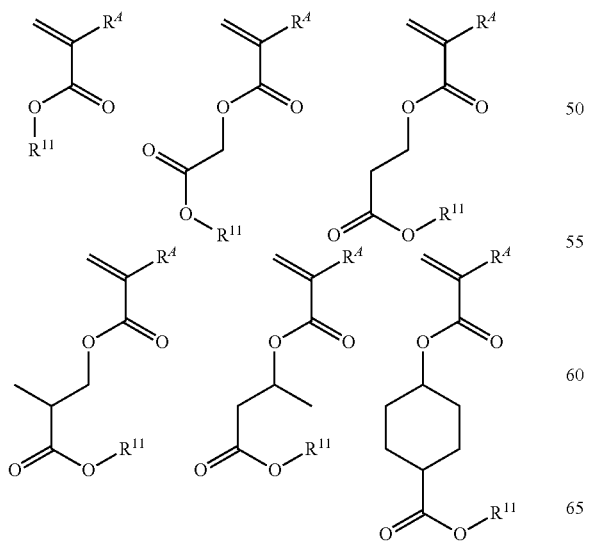

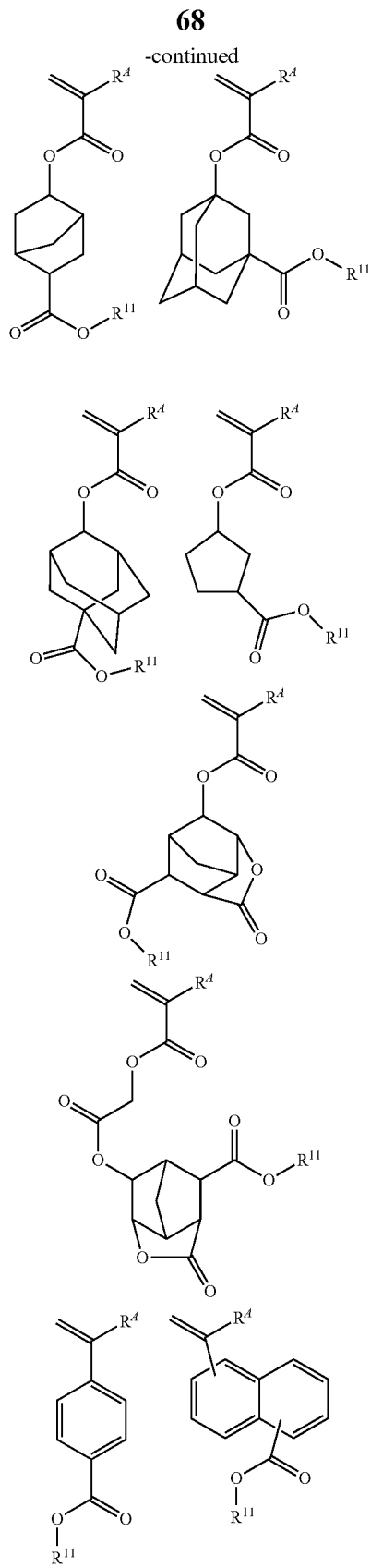

Examples of the monomer from which recurring units (a2) are derived are shown below, but not limited thereto. Herein $R^A$ and $R^{12}$ are as defined above.

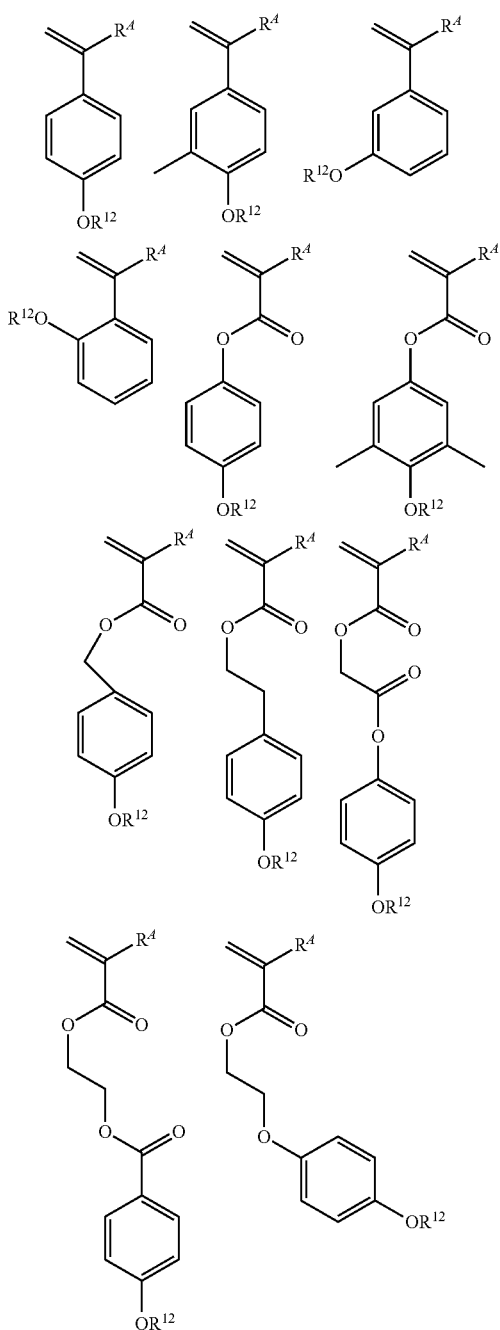

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

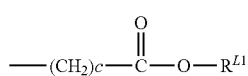
(AL-1)

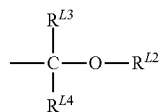
(AL-2)

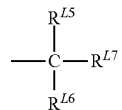
(AL-3)

In formulae (AL-1) and (AL-2), $R^{L1}$ and $R^{L2}$ are each independently a $C_1$-$C_{40}$ monovalent hydrocarbon group which may contain a heteroatom such as oxygen, sulfur, nitrogen or fluorine. The monovalent hydrocarbon groups may be straight, branched or cyclic, with alkyl groups of 1 to 40 carbon atoms, especially 1 to 20 carbon atoms being preferred. In formula (AL-1), c is an integer of 0 to 10, especially 1 to 5.

In formula (AL-2), $R^{L3}$ and $R^{L4}$ are each independently hydrogen or a $C_1$-$C_{20}$ monovalent hydrocarbon group which may contain a heteroatom such as oxygen, sulfur, nitrogen or fluorine. The monovalent hydrocarbon groups may be straight, branched or cyclic, with $C_1$-$C_{20}$ alkyl groups being preferred. Any two of $R^{L2}$, $R^{L3}$ and $R^{L4}$ may bond together to form a ring with the carbon atom or carbon and oxygen atoms to which they are attached. The ring contains 3 to 20 carbon atoms, preferably 4 to 16 carbon atoms, and is typically alicyclic.

In formula (AL-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon groups may be straight, branched or cyclic, with $C_1$-$C_{20}$ alkyl groups being preferred. Any two of $R^{L5}$, $R^{L6}$ and $R^{L7}$ may bond together to form a ring with the carbon atom to which they are attached. The ring contains 3 to 20 carbon atoms, preferably 4 to 16 carbon atoms and is typically alicyclic.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

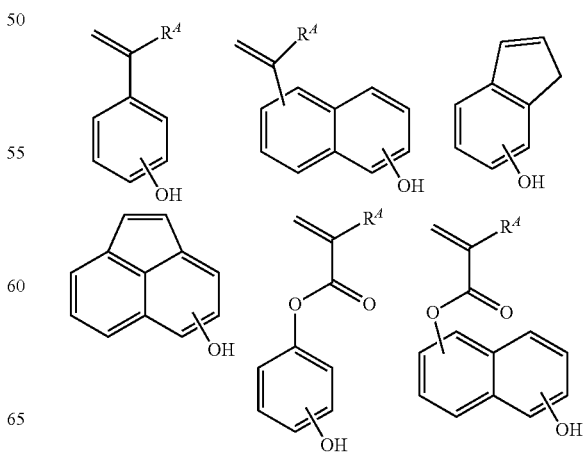

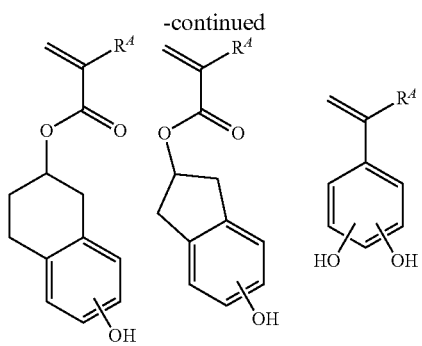
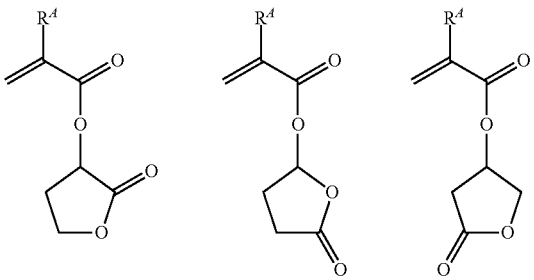
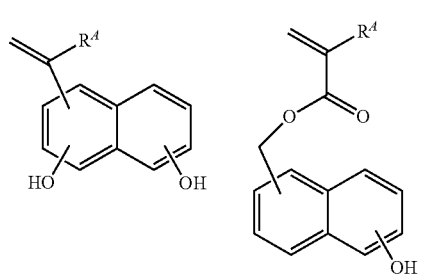
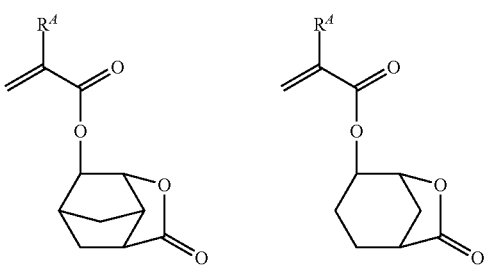
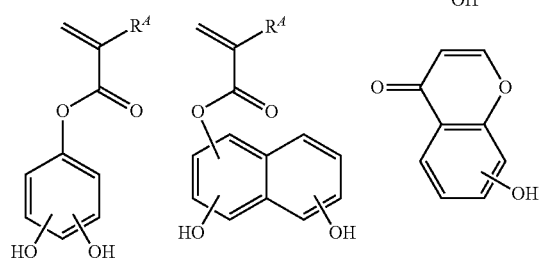
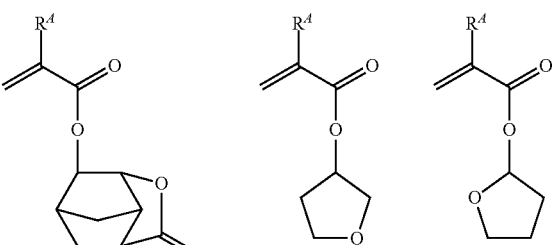
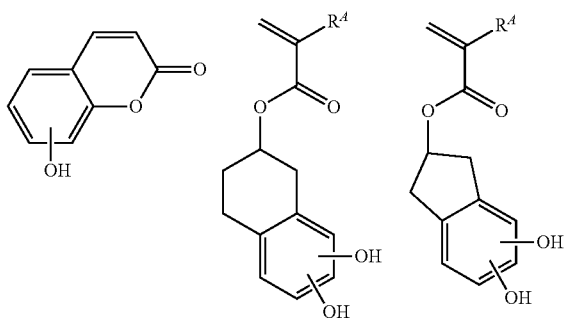

Further, recurring units (c) having another adhesive group selected from hydroxyl (other than the foregoing phenolic hydroxyl), lactone ring, ether, ester, carbonyl, cyano and carboxyl groups may also be incorporated in the base polymer. Examples of suitable monomers from which recurring units (c) are derived are given below, but not limited thereto. Herein $R^A$ is as defined above.

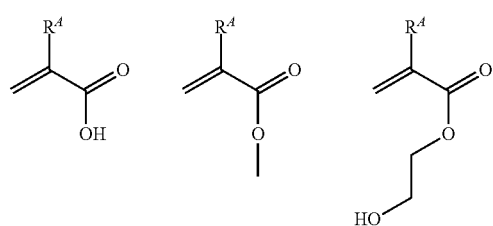
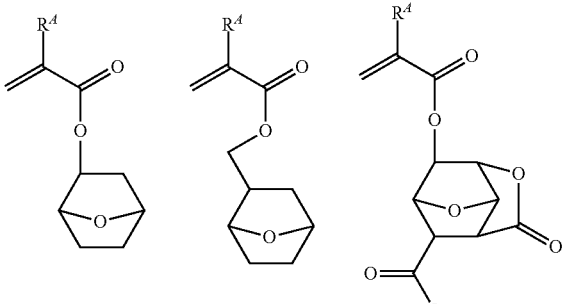
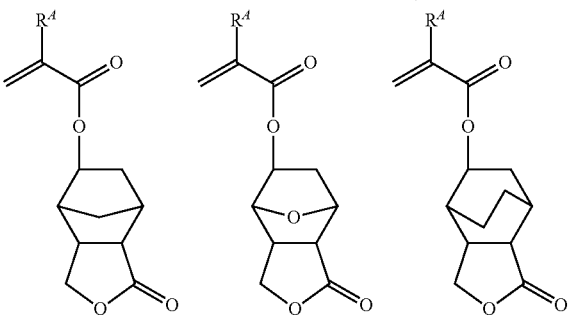

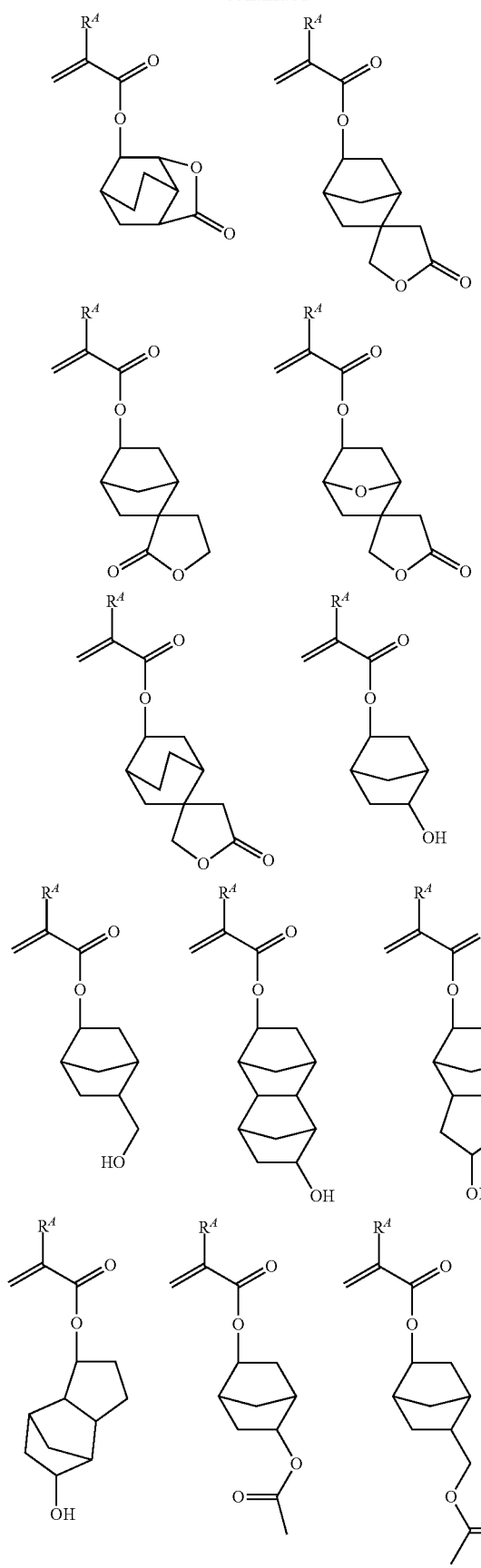
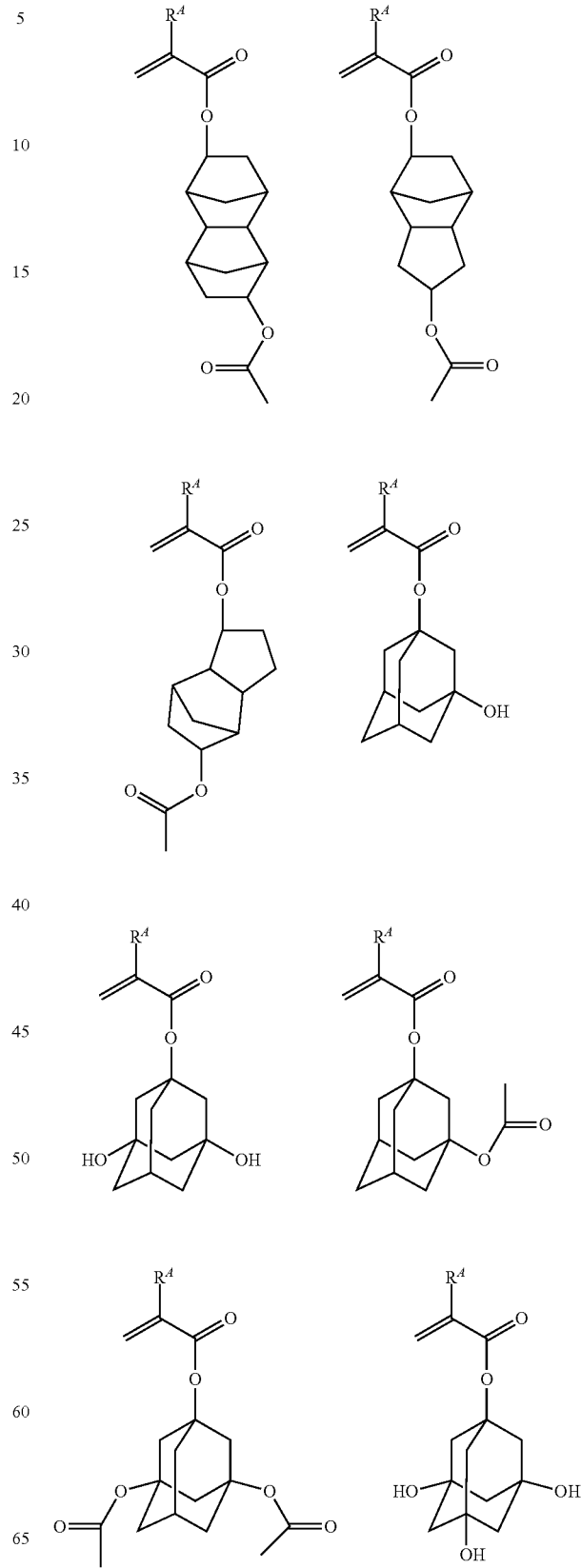

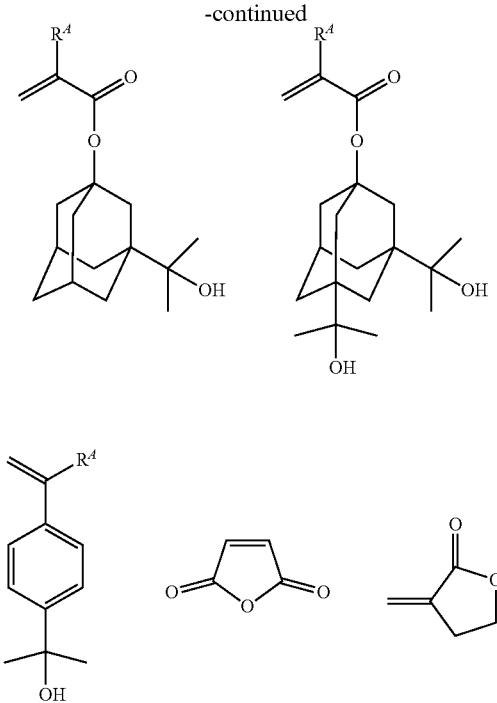
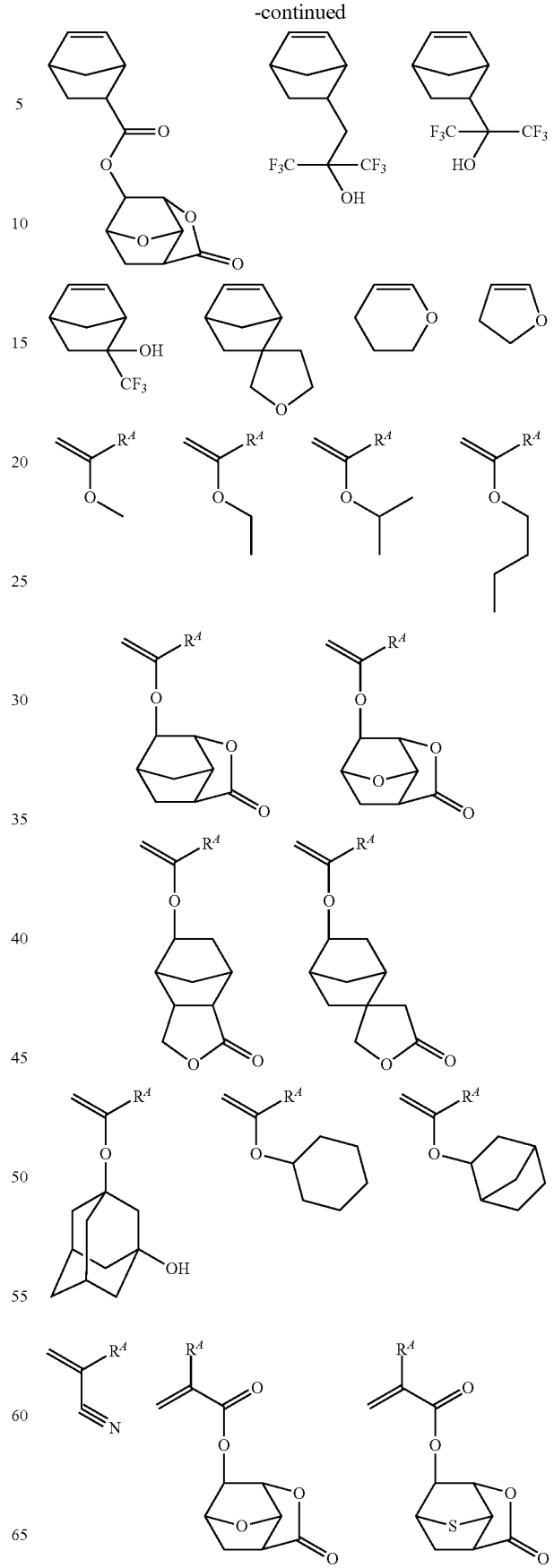

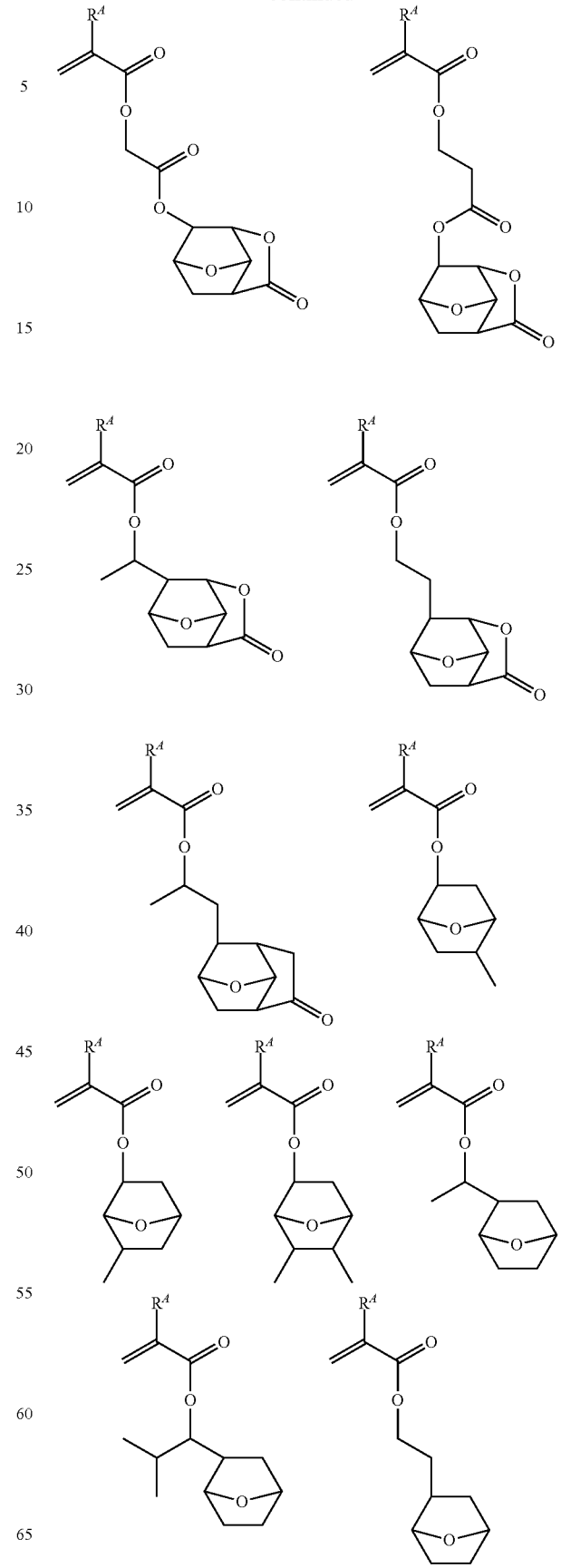

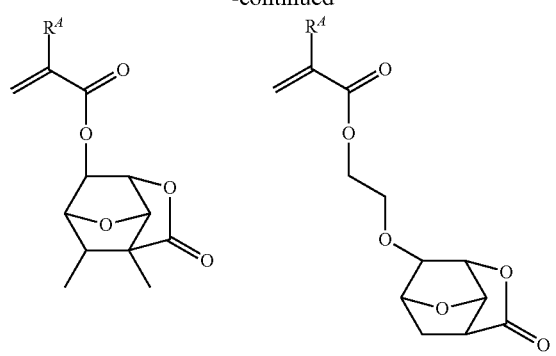
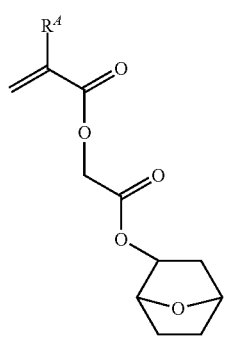
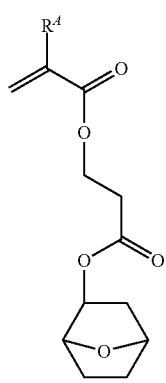
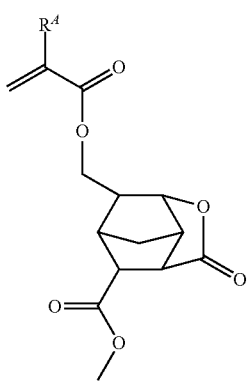
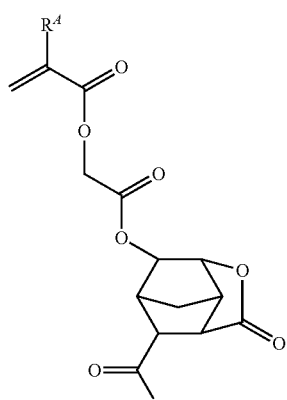
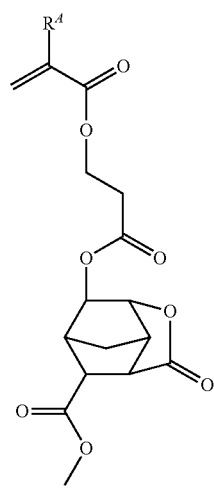
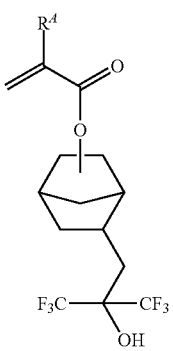
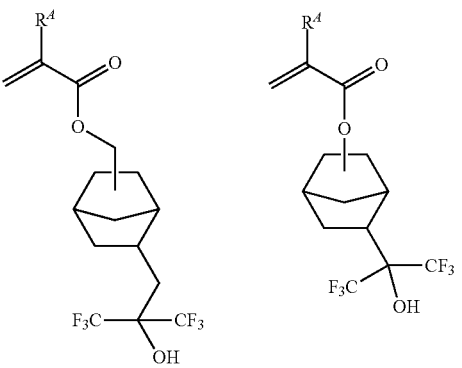
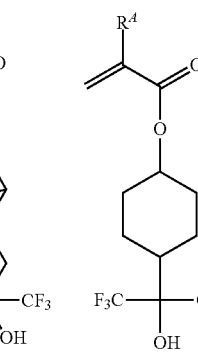
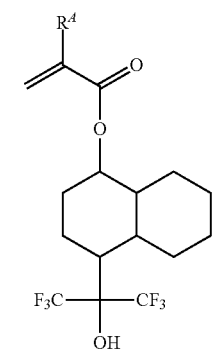
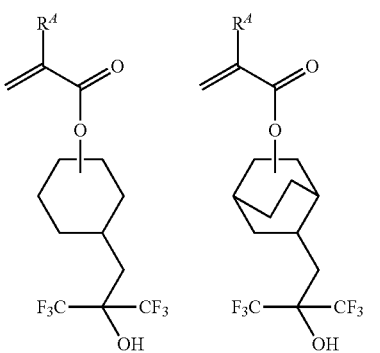
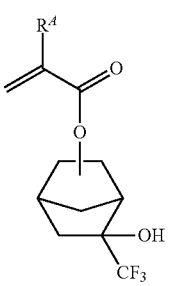
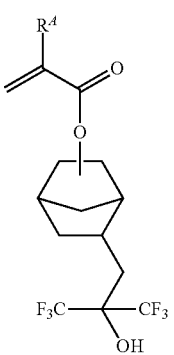

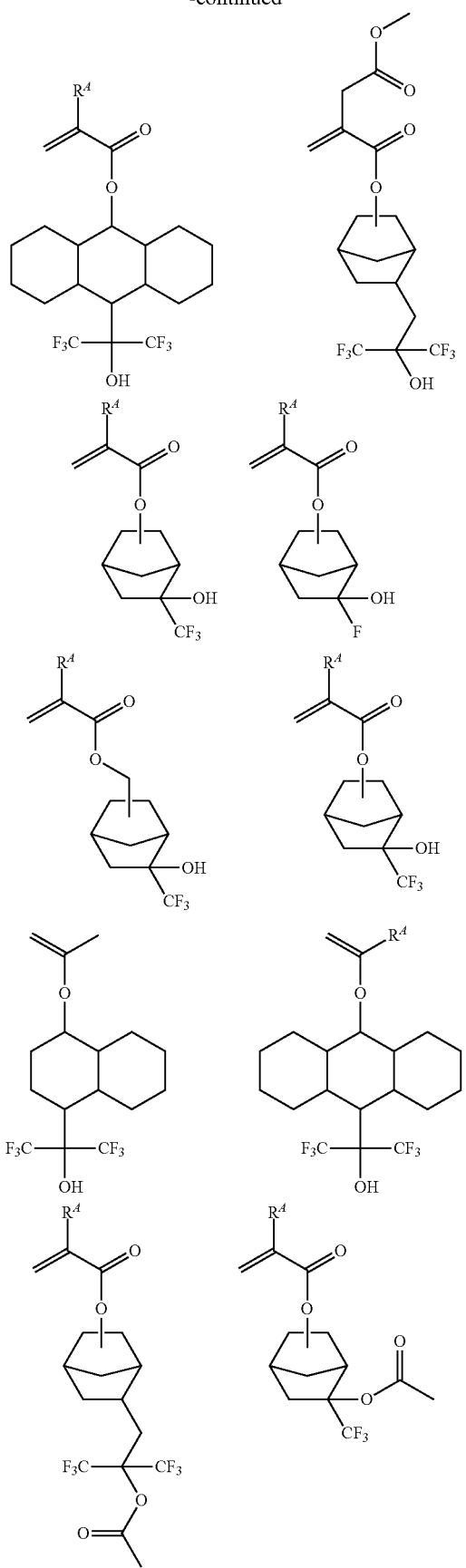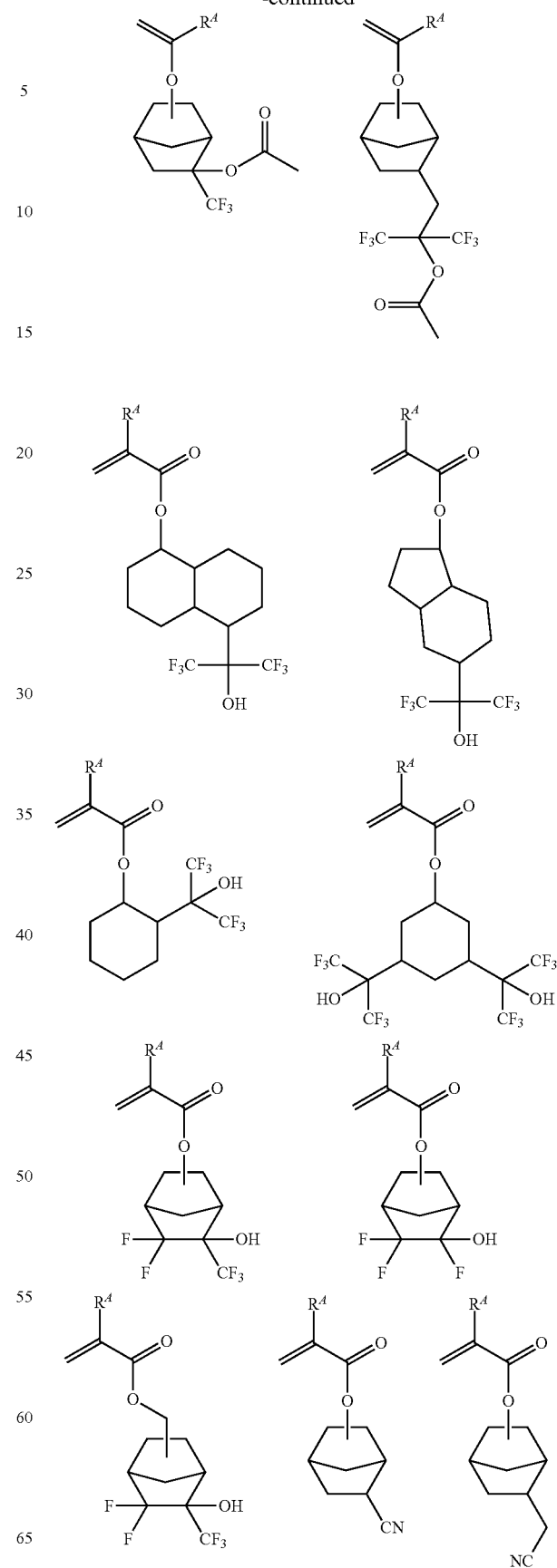

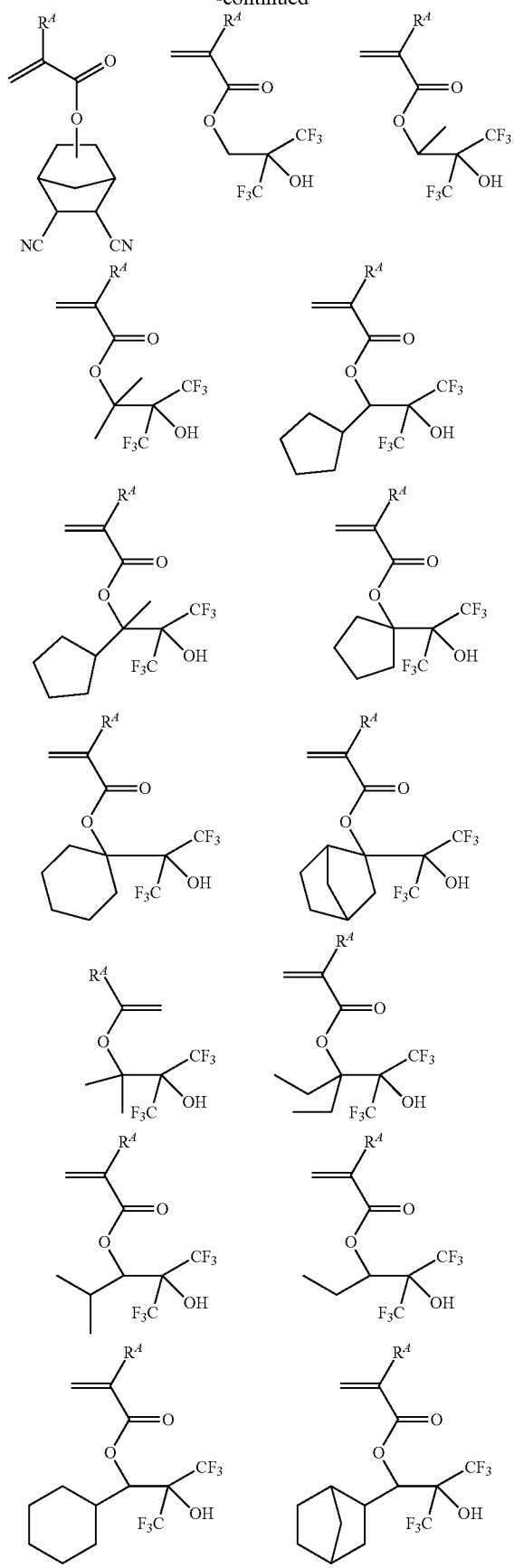
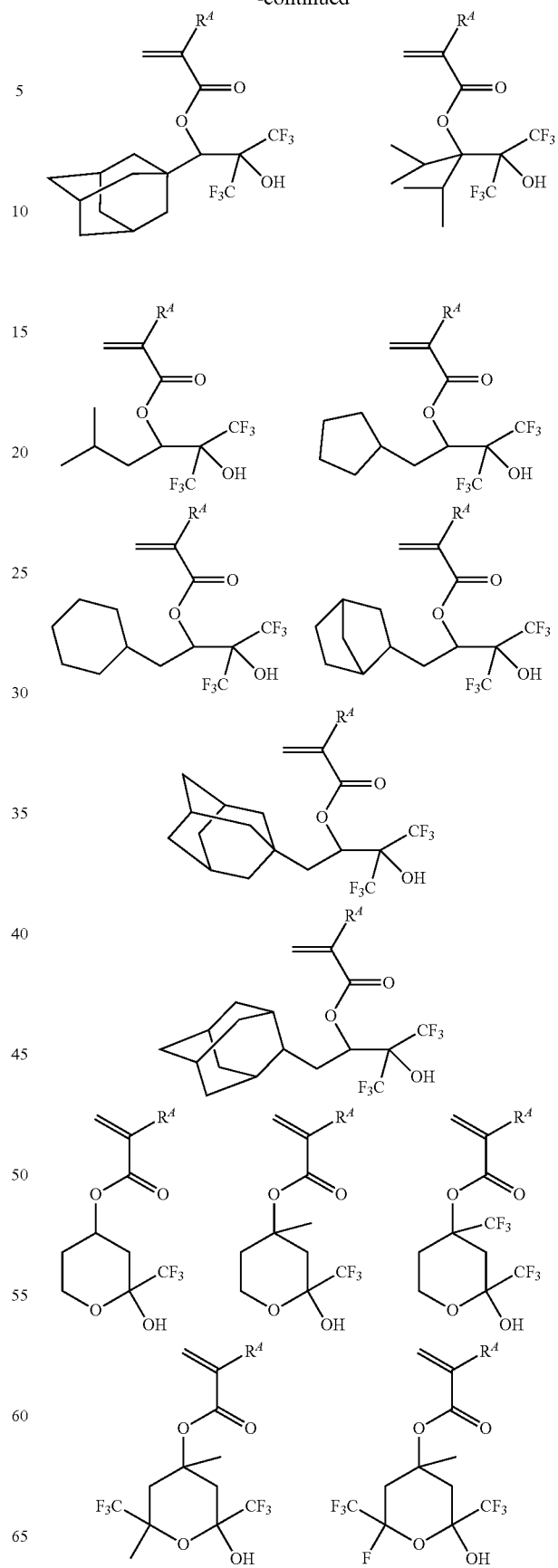

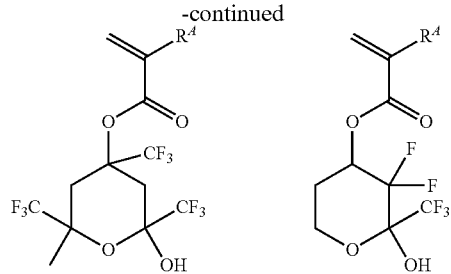
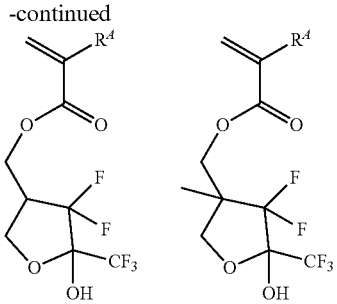
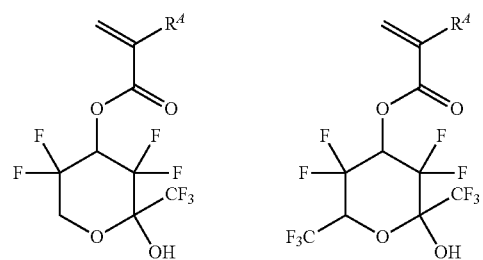
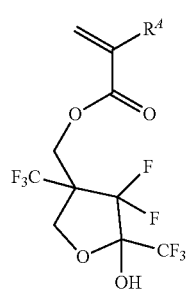
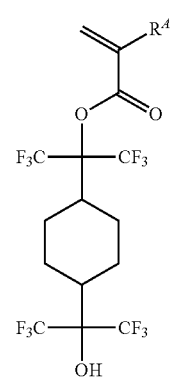
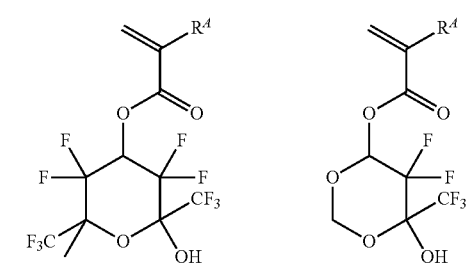
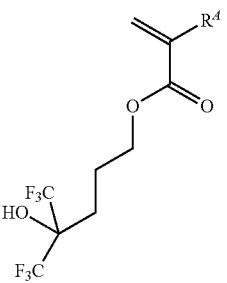
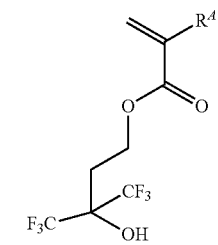
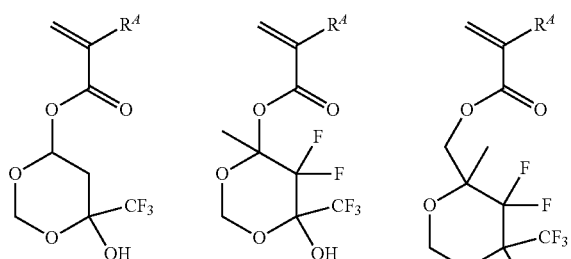
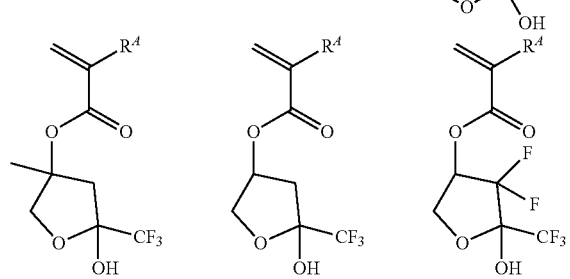
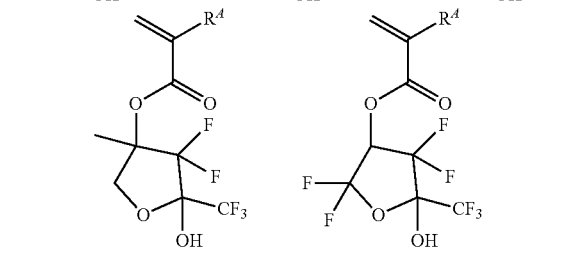
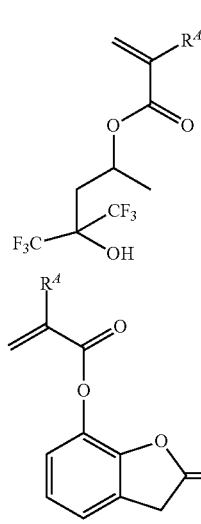
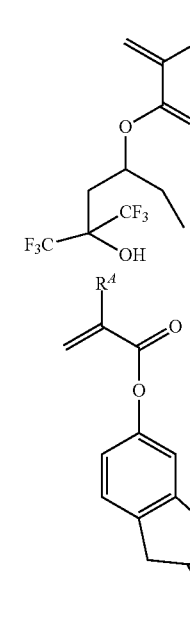

87
-continued
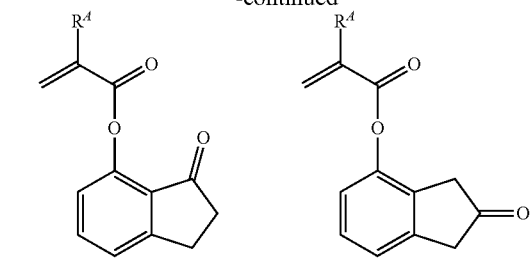
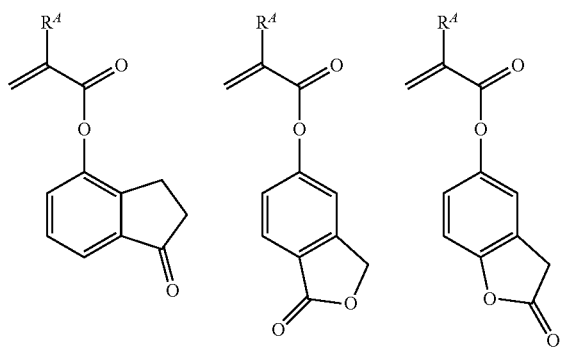
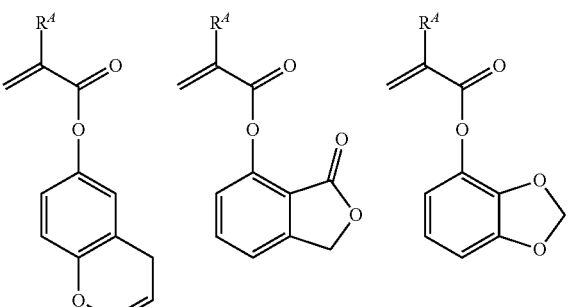
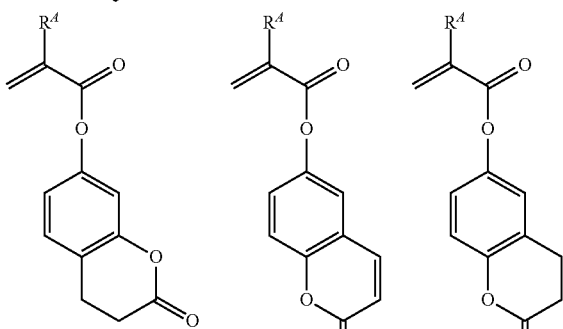
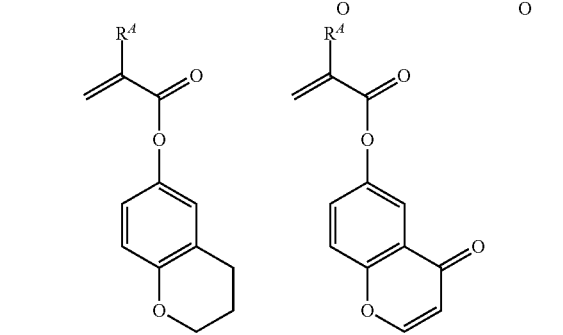
88
-continued
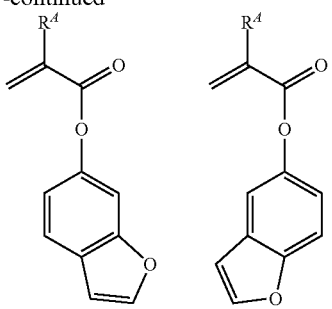
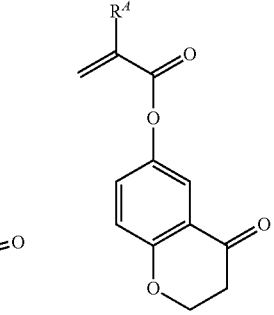
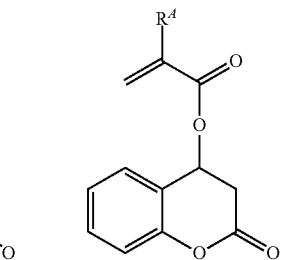
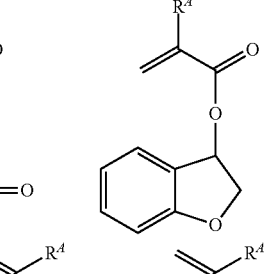
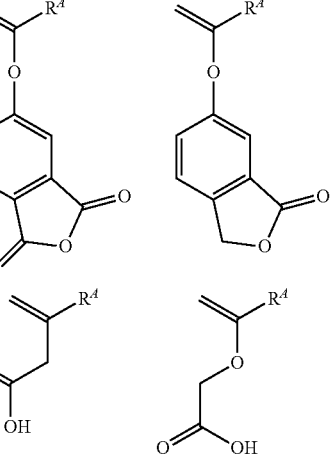

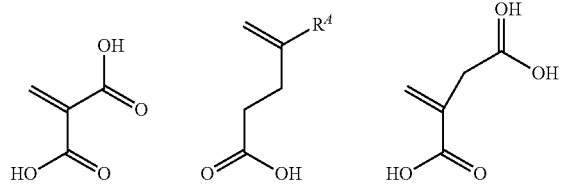
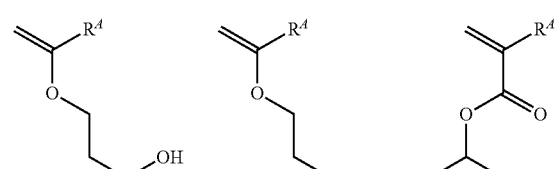
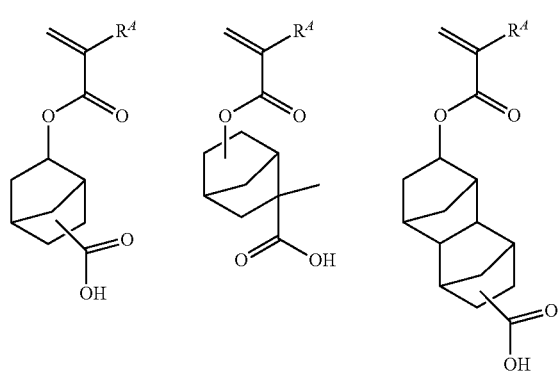
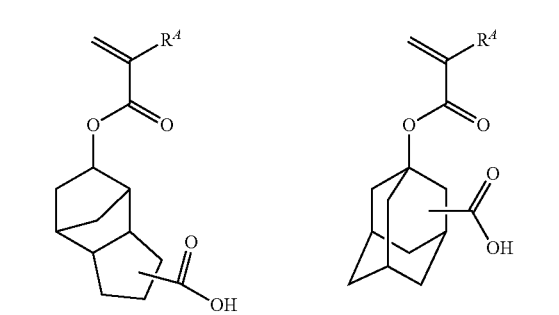
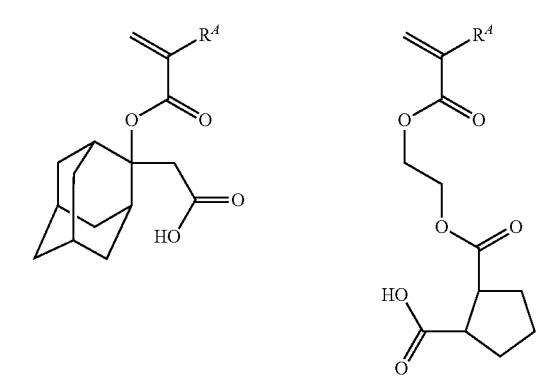
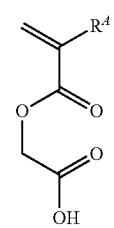
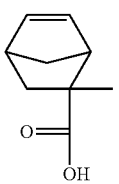
In another preferred embodiment, the base polymer may further comprise recurring units (d) derived from indene, benzofuran, benzothiophene, acenaphthylene, chromone, coumarin, and norbornadiene, or derivatives thereof. Suitable monomers are exemplified below.
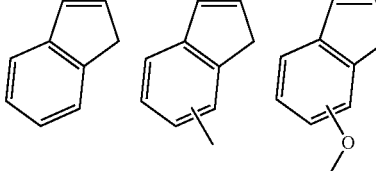
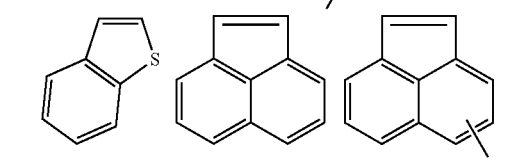

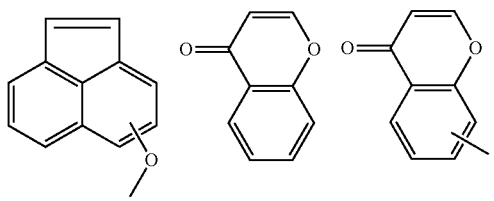
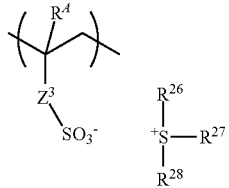

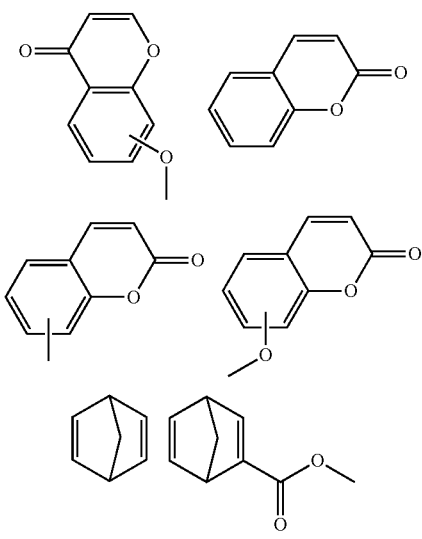

Besides the recurring units described above, further recurring units (e) may be incorporated in the base polymer, examples of which include styrene, vinylnaphthalene, vinylanthracene, vinylpyrene, methyleneindene, vinylpyridine, and vinylcarbazole.

In a further embodiment, recurring units (f) derived from an onium salt having a polymerizable unsaturated bond may be incorporated in the base polymer. The preferred recurring units (f) are recurring units having the following formulae (f1), (f2) and (f3). These units are simply referred to as recurring units (f1), (f2) and (f3), which may be used alone or in combination of two or more types.

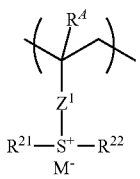
(f1)

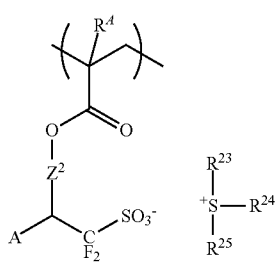
(f2)

(f3)

In formulae (f1) to (f3), $R^A$ is each independently hydrogen or methyl. $Z^1$ is a single bond, phenylene group, —O—$Z^{11}$—, —C(=O)—O—$Z^{11}$—, or —C(=O)—NH—$Z^{11}$—, wherein $Z^{11}$ is a $C_1$-$C_6$ alkanediyl, $C_2$-$C_6$ alkenediyl or phenylene group, which may contain a carbonyl moiety, ester bond, ether bond or hydroxyl moiety. $Z^2$ is a single bond, —$Z^{21}$—C(=O)—O—, —$Z^{21}$—O— or —$Z^{21}$—O—C(=O)—, wherein $Z^{21}$ is a $C_1$-$C_{12}$ alkanediyl group which may contain a carbonyl moiety, ester bond or ether bond. $Z^3$ is a single bond, methylene, ethylene, phenylene or fluorinated phenylene group, —O—$Z^{31}$—, —C(=O)—O—$Z^{31}$—, or —C(=O)—NH—$Z^{31}$—, wherein $Z^{31}$ is a $C_1$-$C_6$ alkanediyl, $C_2$-$C_6$ alkenediyl, phenylene, fluorinated phenylene, or trifluoromethyl-substituted phenylene group, which may contain a carbonyl moiety, ester bond, ether bond or hydroxyl moiety. Notably, the alkanediyl and alkenediyl groups may be straight, branched or cyclic.

In formulae (f1) to (f3), $R^{21}$ to $R^{28}$ are each independently a $C_1$-$C_{20}$ monovalent hydrocarbon group which may contain a heteroatom. The monovalent hydrocarbon group may be straight, branched or cyclic and examples thereof include $C_1$-$C_{12}$ alkyl, $C_6$-$C_{12}$ aryl, and $C_7$-$C_{20}$ aralkyl groups. In these groups, some or all hydrogen may be substituted by $C_1$-$C_{10}$ alkyl, halogen, trifluoromethyl, cyano, nitro, hydroxyl, mercapto, $C_1$-$C_{10}$ alkoxy, $C_2$-$C_{10}$ alkoxycarbonyl, or $C_2$-$C_{10}$ acyloxy moiety, or some carbon may be replaced by a carbonyl moiety, ether bond or ester bond. Any two of $R^{23}$, $R^{24}$ and $R^{25}$ or any two of $R^{26}$, $R^{27}$ and $R^{28}$ may bond together to form a ring with the sulfur atom to which they are attached. The thus formed ring is as exemplified above for the case where two $R^5$ bond together to form a ring with the sulfur atom in formula (1). "A" is hydrogen or trifluoromethyl.

In formula (f1), M⁻ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (K-1) and sulfonate ions having fluorine substituted at α- and β-positions as represented by the formula (K-2).

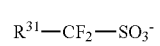
(K-1)

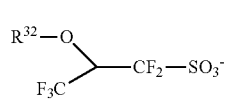
(K-2)

In formula (K-1), $R^{31}$ is hydrogen, or a $C_1$-$C_{20}$ alkyl group, $C_2$-$C_{20}$ alkenyl group, or $C_6$-$C_{20}$ aryl group, which may contain an ether bond, ester bond, carbonyl moiety, lactone ring, or fluorine atom. The alkyl and alkenyl groups may be straight, branched or cyclic.

In formula (K-2), $R^{32}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl, acyl and alkenyl groups may be straight, branched or cyclic.

Examples of the monomer from which recurring unit (f1) is derived are shown below, but not limited thereto. $R^A$ and $M^-$ are as defined above.

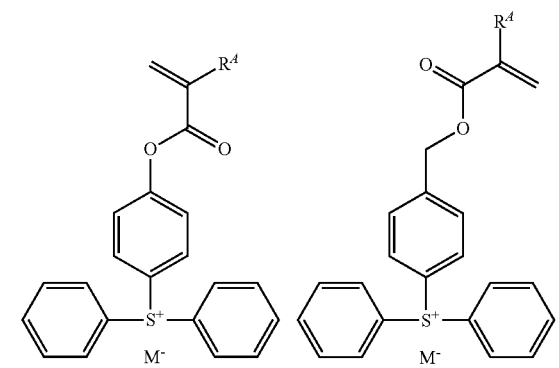

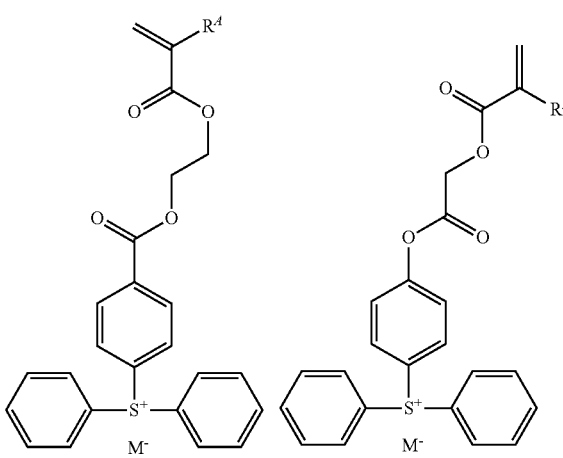

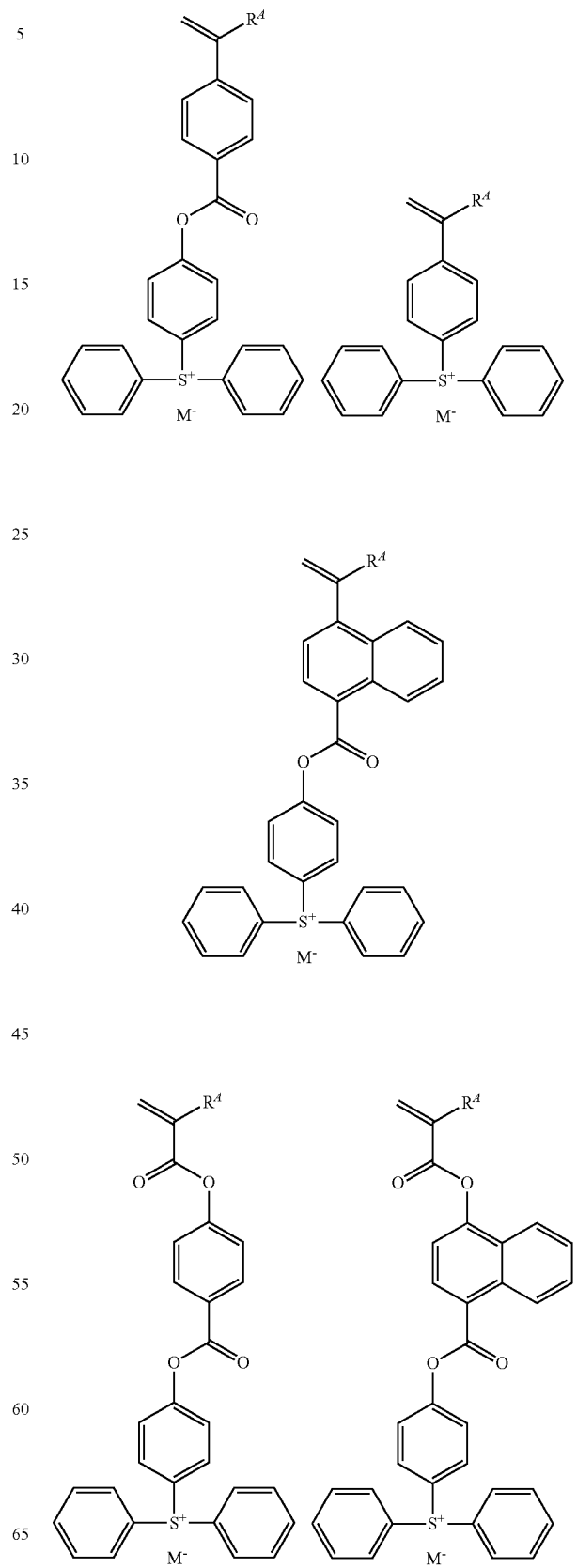

-continued

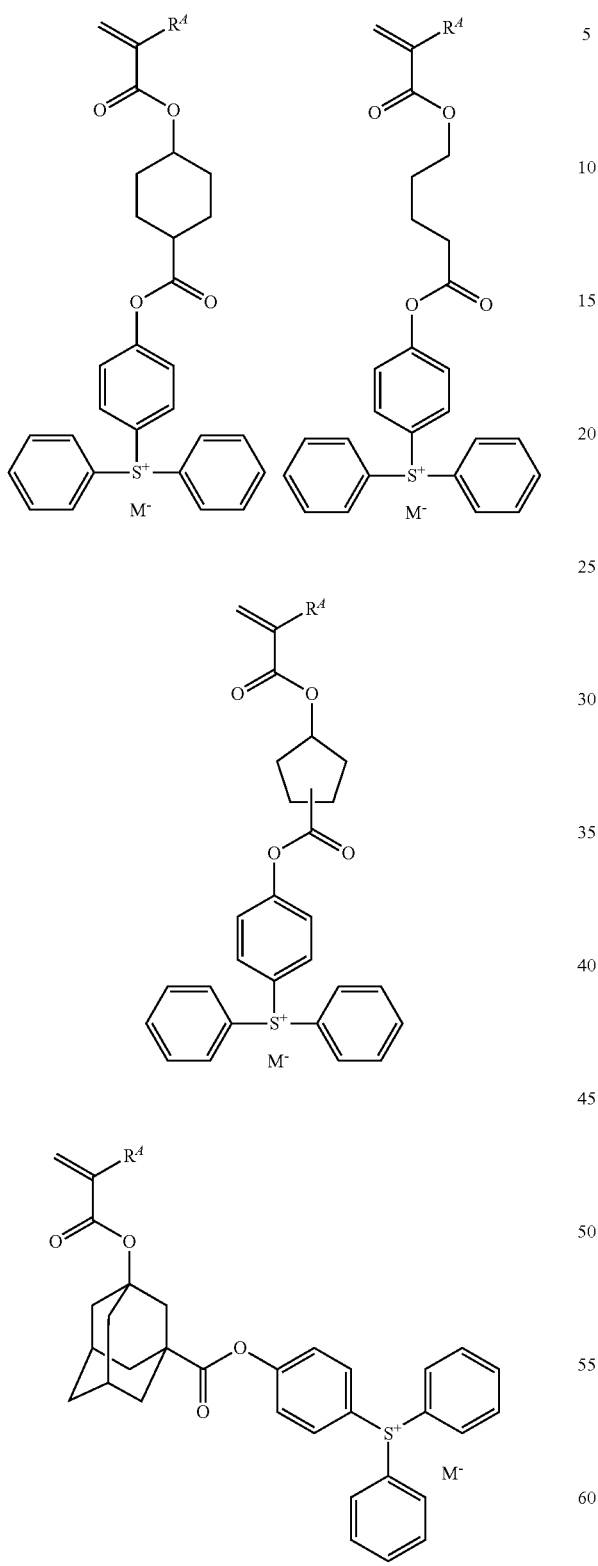
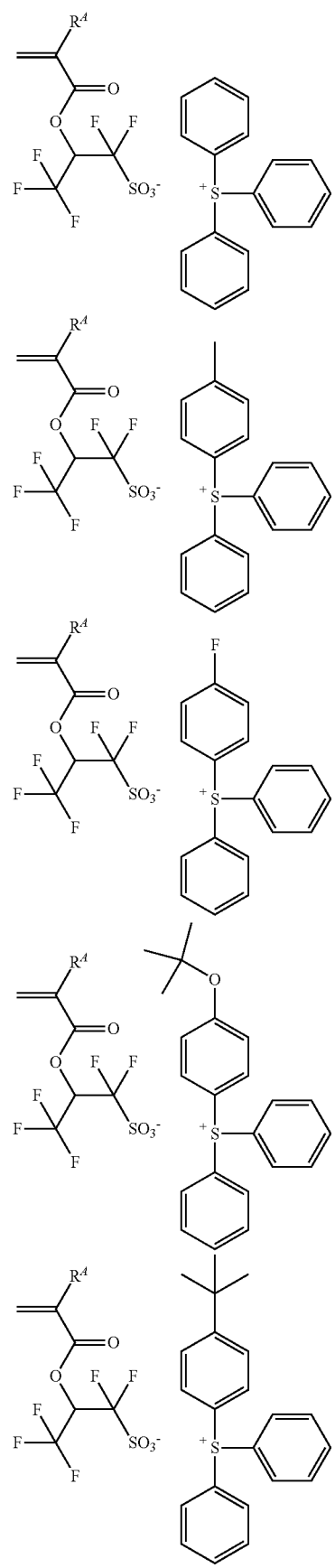
Examples of the monomer from which recurring unit (f2) is derived are shown below, but not limited thereto. $R^A$ is as defined above.

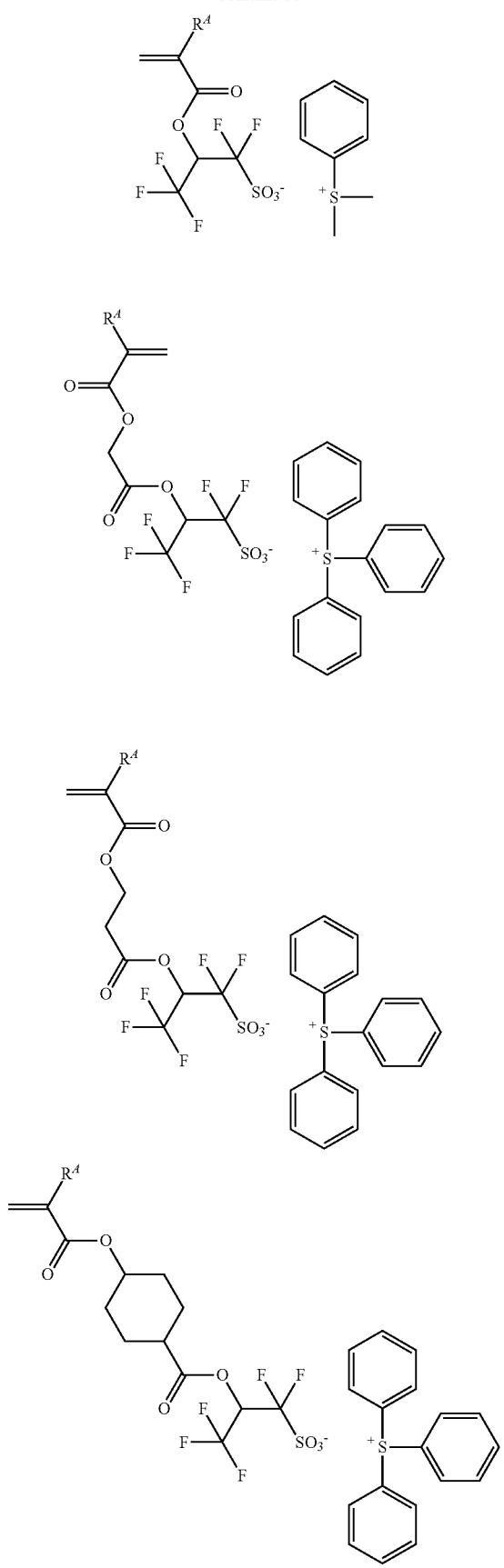

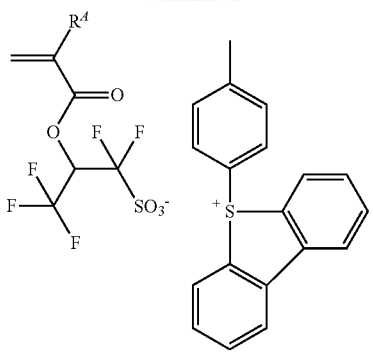
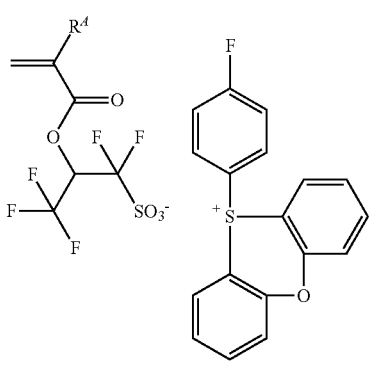
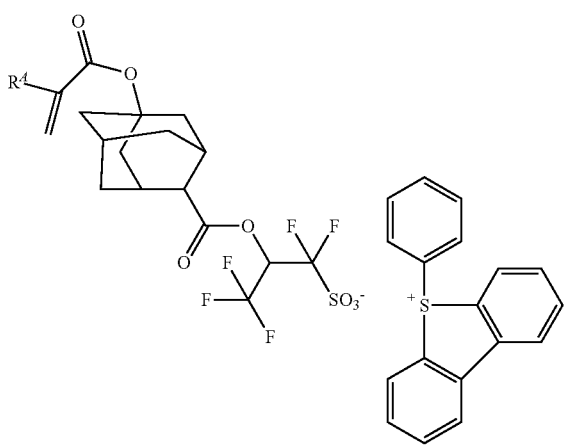
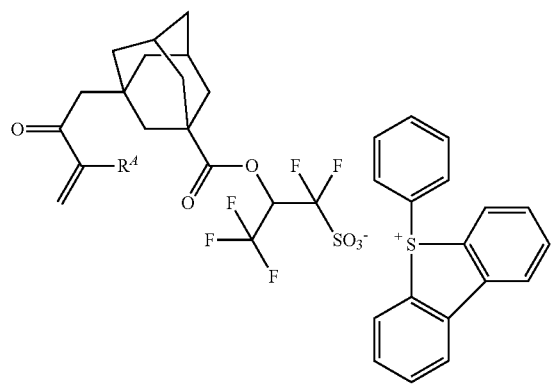
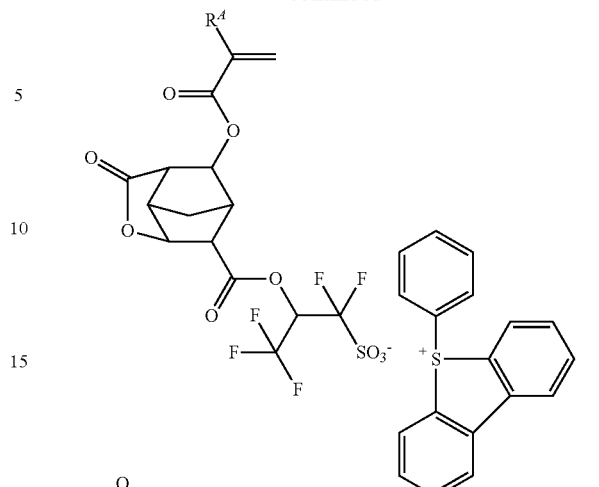
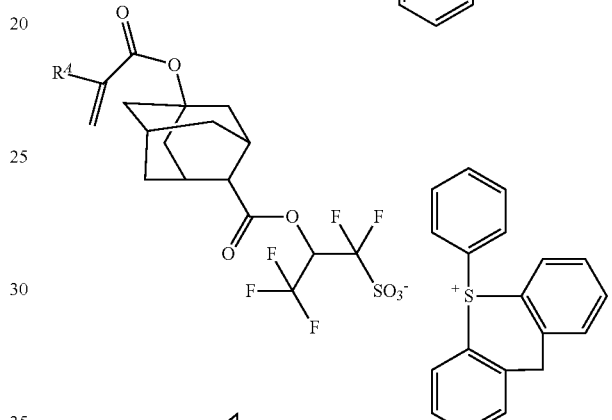
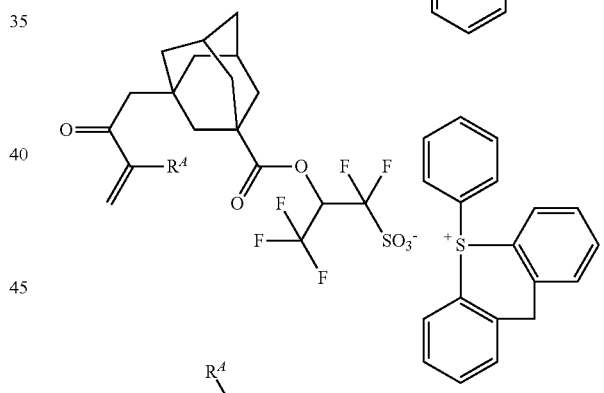
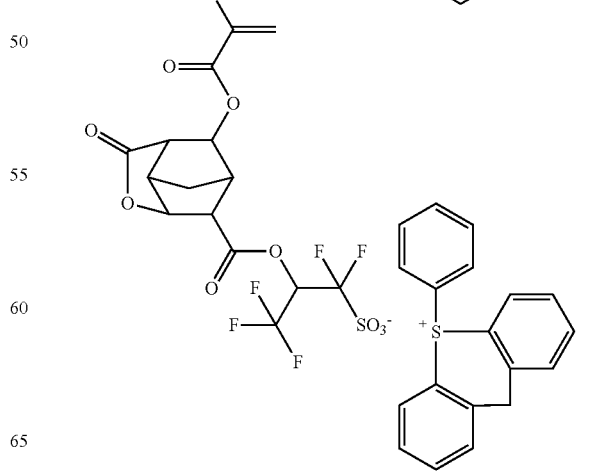

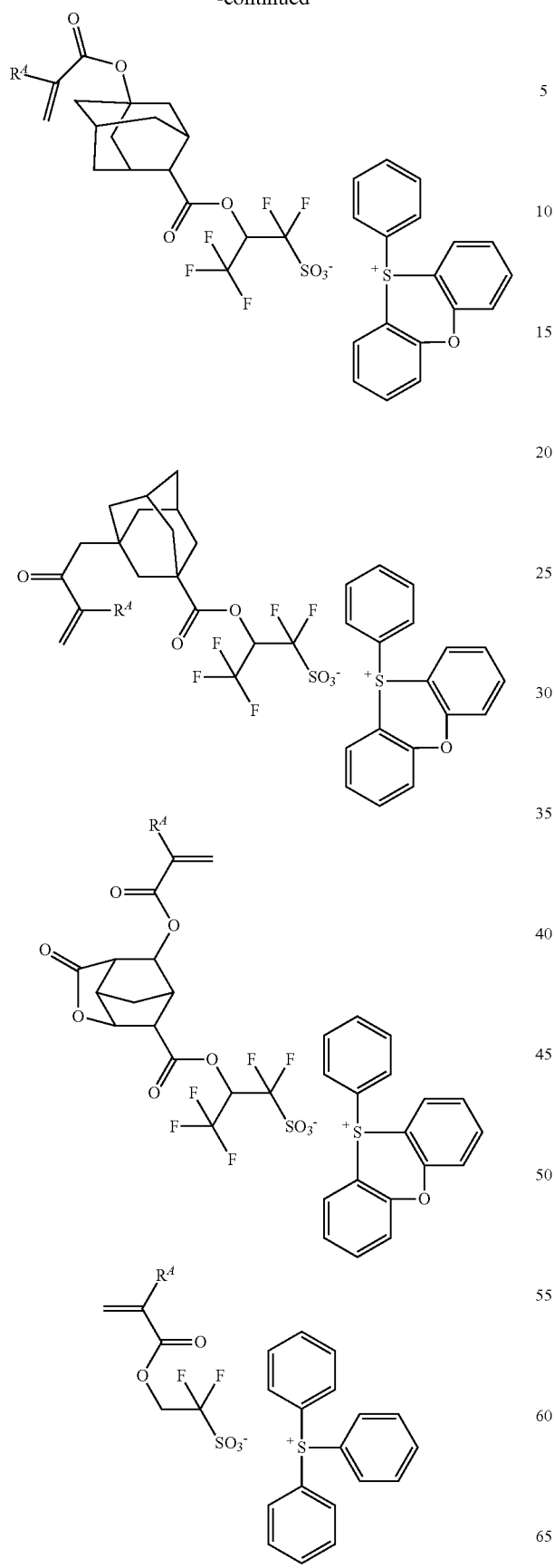
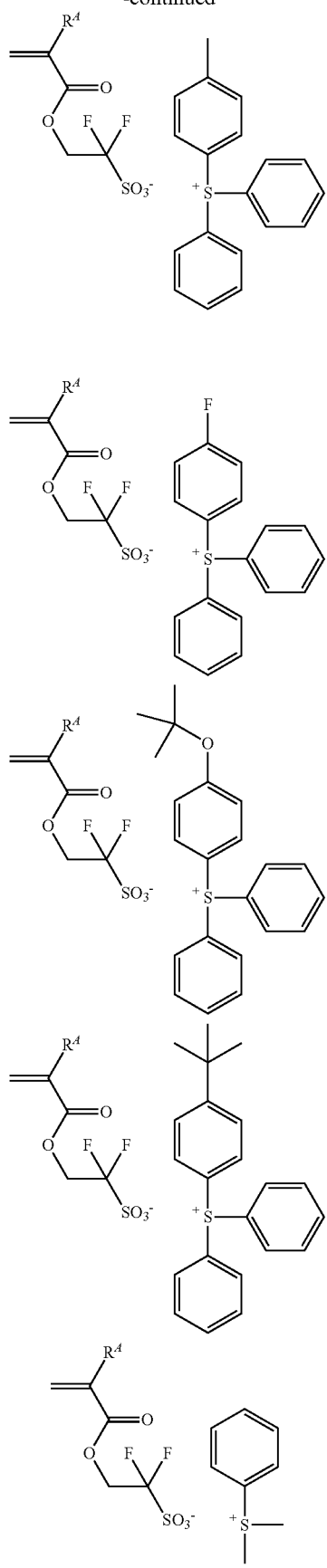

-continued
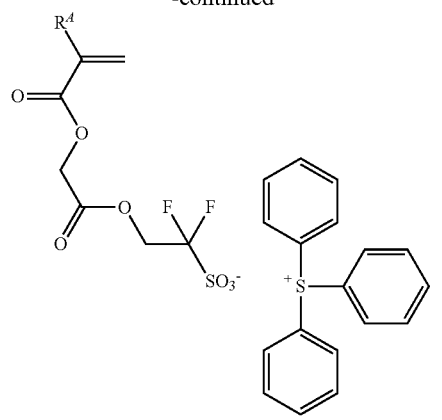
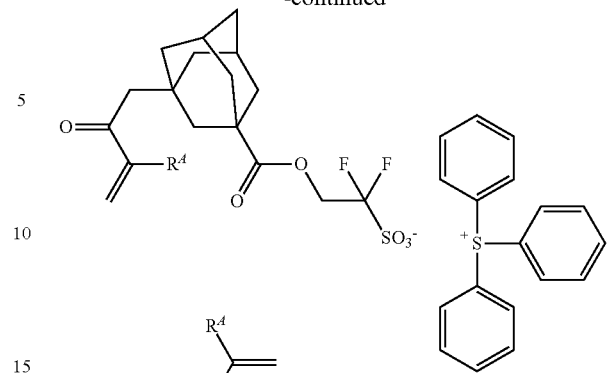
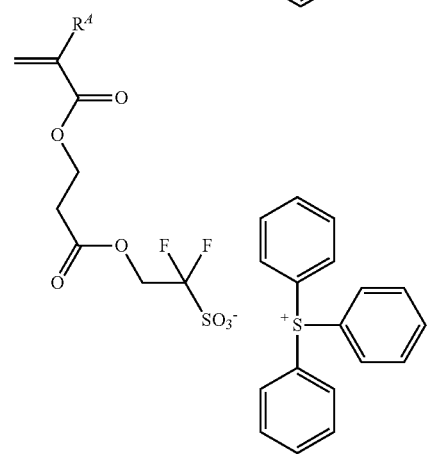
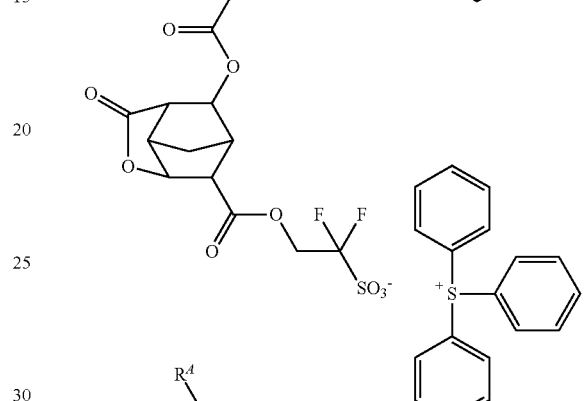
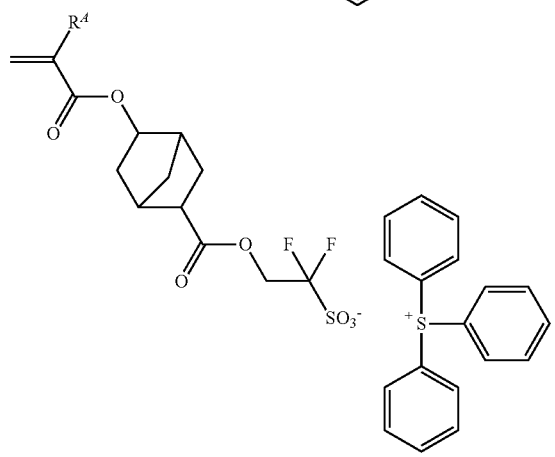
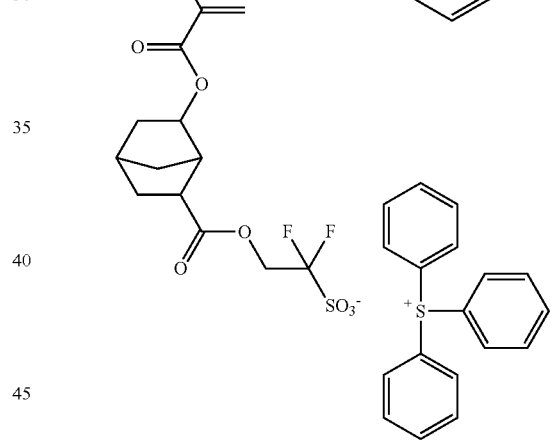
Examples of the monomer from which recurring unit (f3) is derived are shown below, but not limited thereto. $R^A$ is as defined above.
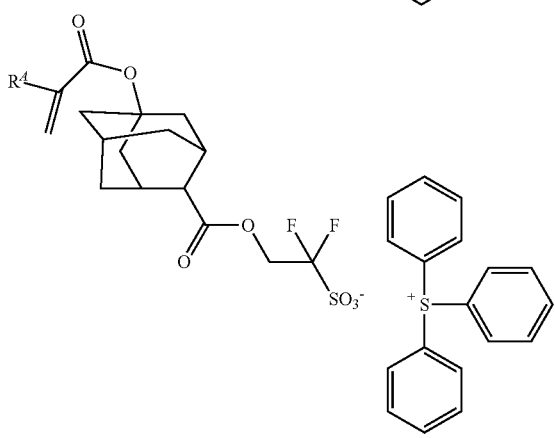
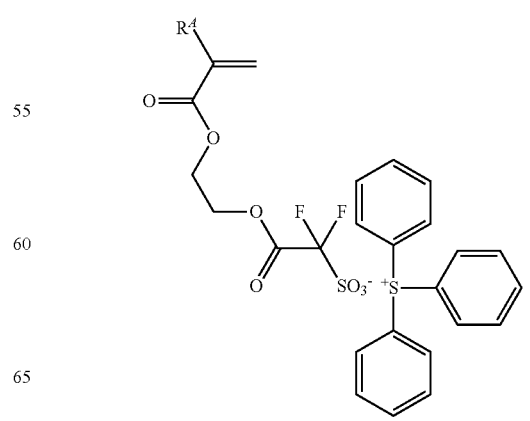

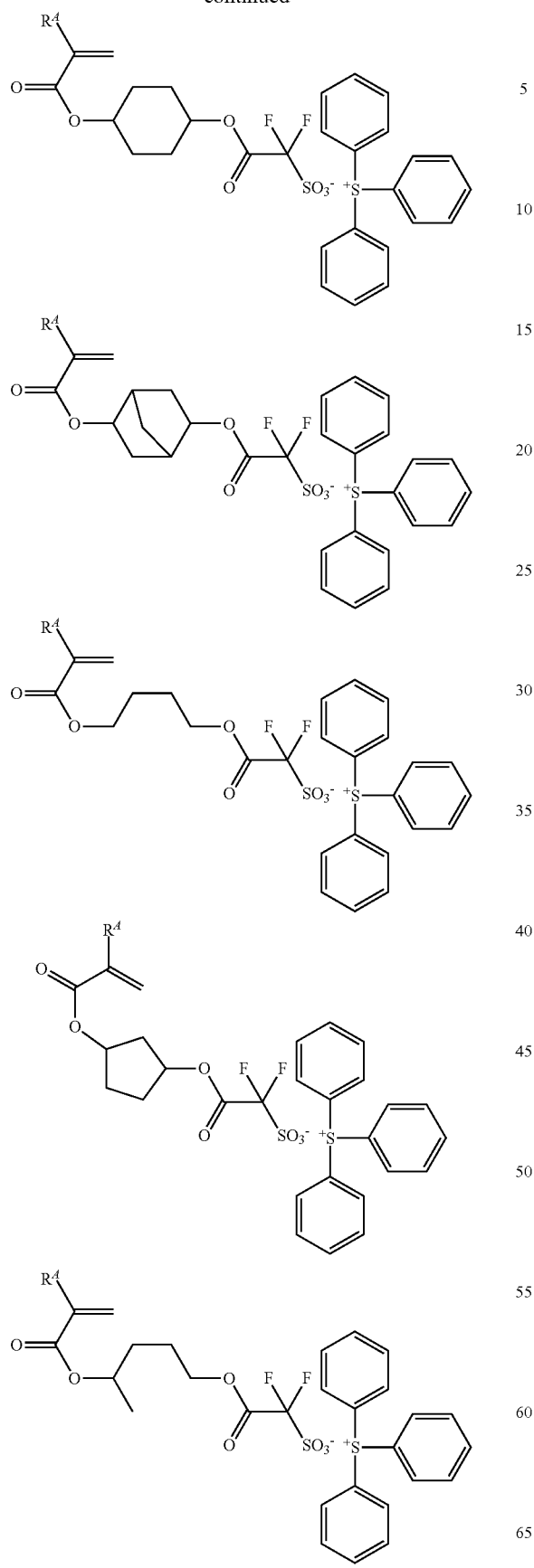
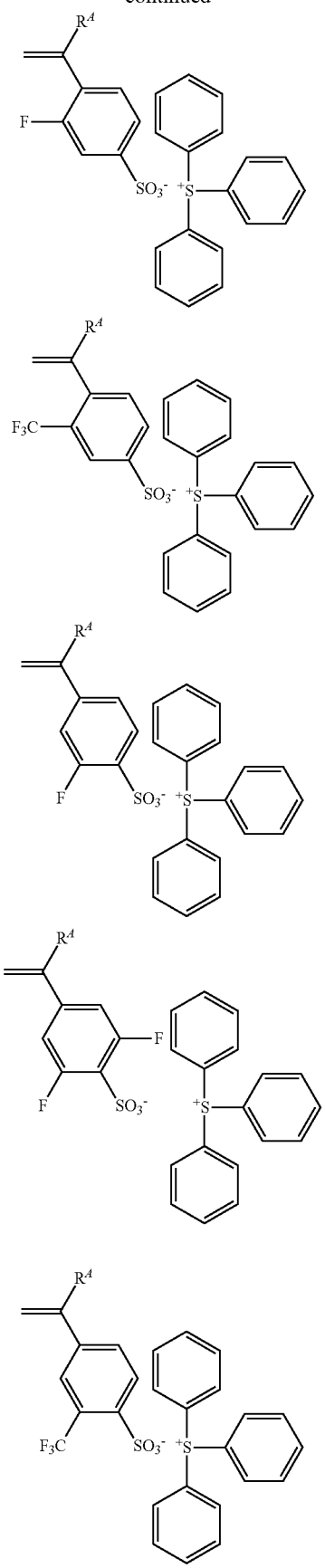

-continued
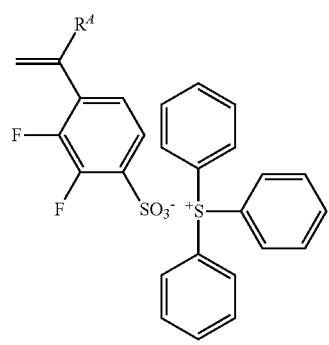
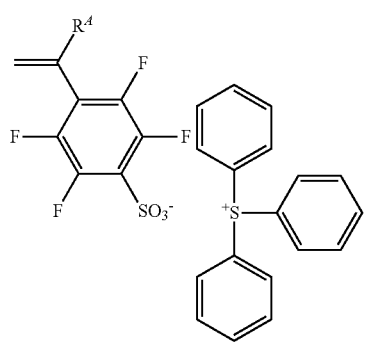
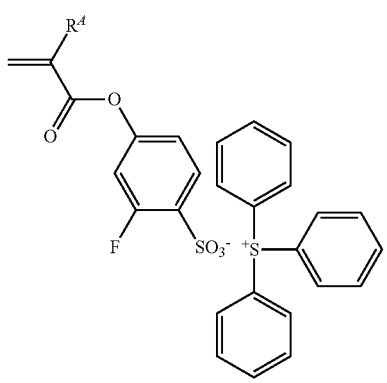
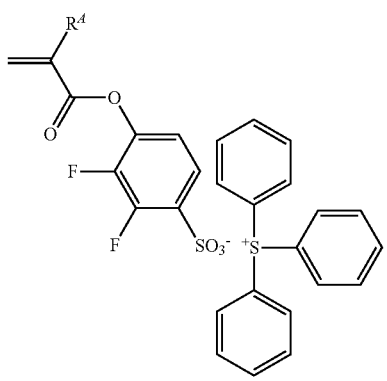
-continued
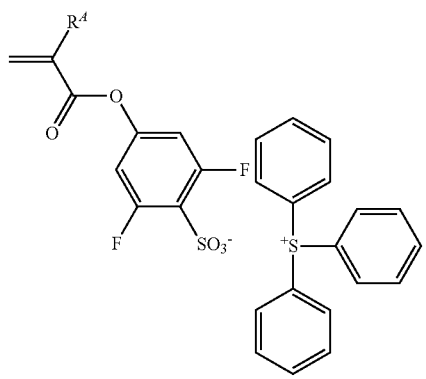
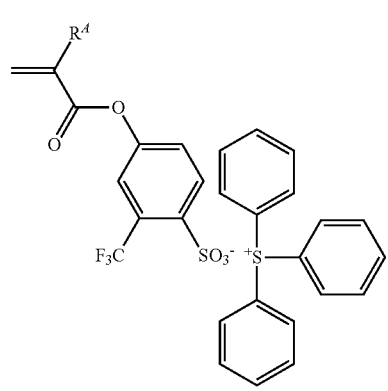
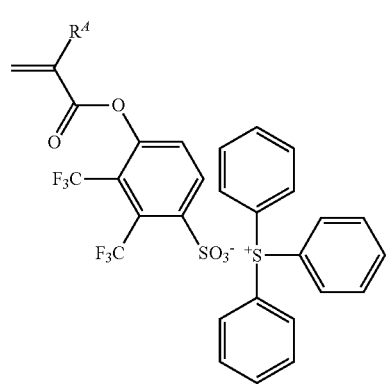
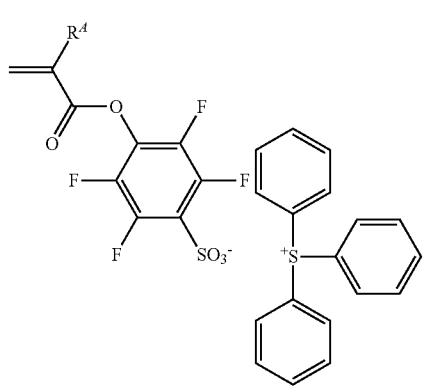

-continued

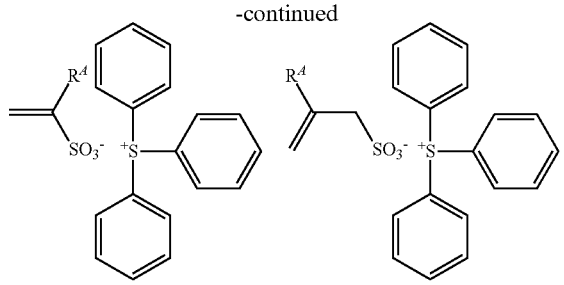

The attachment of an acid generator to the polymer main chain is effective in restraining acid diffusion, thereby preventing a reduction of resolution due to blur by acid diffusion. Also LWR is improved since the acid generator is uniformly distributed. When a base polymer comprising recurring units (f) is used, an acid generator capable of generating a strong acid may or may not be added.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq d \leq 0.8$, $0 \leq e \leq 0.8$, and $0 \leq f \leq 0.5$; more preferably $0 \leq a1 \leq 0.9$, $0 \leq a2 \leq 0.9$, $0.1 \leq a1+a2 \leq 0.9$, $0 \leq b \leq 0.8$, $0 \leq c \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \leq 1.0$, $0 \leq c \leq 0.9$, $0 \leq d \leq 0.8$, $0 \leq e \leq 0.8$, and $0 \leq f \leq 0.5$; more preferably $0.2 \leq b \leq 1.0$, $0 \leq c \leq 0.8$, $0 \leq d \leq 0.7$, $0 \leq e \leq 0.7$, and $0 \leq f \leq 0.4$; and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 80° C., and the reaction time is 2 to 100 hours, more preferably 5 to 20 hours.

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

The base polymer may be a blend of two or more polymers which differ in compositional ratio, Mw or Mw/Mn.

Other Components

In the resist composition containing the quencher having formula (1) and the base polymer defined above, other components such as an acid generator capable of generating a strong acid, organic solvent, surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when a chemically amplified resist composition capable of utilizing acid catalyzed reaction is formulated, the composition has a higher sensitivity and is further improved in the properties described above.

The resist composition may contain an acid generator capable of generating a strong acid sufficient to induce deprotection reaction in the positive resist material and crosslinking reaction or polarity switch reaction in the negative resist material. The acid generator is typically a compound (PAG) capable of generating an acid upon exposure to actinic ray or radiation. Although the PAG used herein may be any compound capable of generating an acid upon exposure to high-energy radiation, those compounds capable of generating fluorosulfonic acid, fluoroimidic acid (imide acid) or fluoromethide acid are preferred. Suitable PAGs include sulfonium salts, iodonium salts, sulfonyldiazomethane, N-sulfonyloxyimide, and oxime-O-sulfonate acid generators.

Suitable acid generators capable of generating fluorosulfonic acid, fluoroimidic acid or fluoromethide acid include those compounds having α-fluorosulfonate anions as described in JP-A 2004-531749, JP-A 2007-145797, JP-A 2008-007410, JP-A 2018-101130, JP-A 2018-049177, and WO 2011/093139, β-fluorosulfonate anions as described in JP-A 2014-133725, α-fluorosulfonate anions, fluoroimide anions and fluoromethide anions as described in JP-A 2014-126767, and fluorosulfonimide anions as described in JP-A 2016-210761.

Also a sulfonium or iodonium salt having an iodized or brominated aromatic ring-containing anion may be used as the PAG. Suitable are sulfonium and iodonium salts having the formulae (2) and (3). When such an acid generator is added, a higher sensitivity is achievable due to the substantial absorption of EUV by iodine atoms.

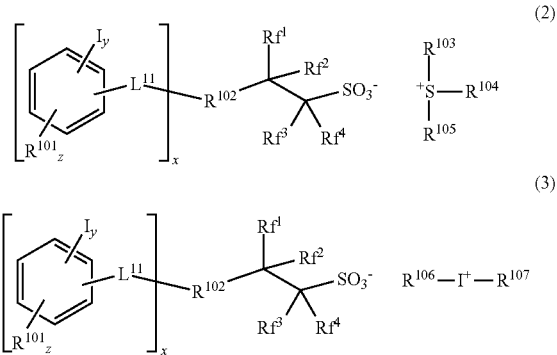

In formulae (2) and (3), $L^{11}$ is a single bond, ether bond, ester bond, or a $C_1$-$C_6$ alkanediyl group which may contain an ether bond or ester bond. The alkanediyl group may be straight, branched or cyclic.

In formulae (2) and (3), $R^{101}$ is a hydroxyl group, carboxyl group, fluorine, chlorine, bromine, amino group, or a $C_1$-$C_{20}$ alkyl, $C_1$-$C_{20}$ alkoxy, $C_2$-$C_{20}$ alkoxycarbonyl, $C_2$-$C_{20}$ acyloxy or $C_1$-$C_{20}$ alkylsulfonyloxy group, which may contain fluorine, chlorine, bromine, hydroxyl, amino or $C_1$-$C_{10}$ alkoxy moiety, or —$NR^{101A}$—$C(=O)$—$R^{101B}$ or —$NR^{101A}$—$C(=O)$—$O$—$R^{101B}$, wherein $R^{101A}$ is hydrogen, or a $C_1$-$C_6$ alkyl group which may contain halogen, hydroxy, $C_1$-$C_6$ alkoxy, $C_2$-$C_6$ acyl or $C_2$-$C_6$ acyloxy moiety, $R^{101B}$ is a $C_1$-$C_{16}$ alkyl, $C_2$-$C_{16}$ alkenyl or $C_6$-$C_{12}$ aryl group, which may contain halogen, hydroxy, $C_1$-$C_6$ alkoxy, $C_2$-$C_6$ acyl or $C_2$-$C_6$ acyloxy moiety. The foregoing alkyl, alkoxy, alkoxycarbonyl, acyloxy, acyl and alkenyl groups may be straight, branched or cyclic. When z is 2 or more, groups $R^{101}$ may be the same or different.

In formulae (2) and (3), $R^{102}$ is a single bond or a $C_1$-$C_{20}$ divalent linking group when x=1, or a $C_1$-$C_{20}$ tri- or tetravalent linking group when x=2 or 3, the linking group optionally containing an oxygen, sulfur or nitrogen atom.

In formulae (2) and (3), $Rf^1$ to $Rf^4$ are each independently hydrogen, fluorine or trifluoromethyl, at least one of $Rf^1$ to $Rf^4$ is fluorine or trifluoromethyl, or $Rf^1$ and $Rf^2$, taken together, may form a carbonyl group. Preferably, both $Rf^3$ and $Rf^4$ are fluorine.

In formulae (2) and (3), $R^{103}$, $R^{104}$, $R^{105}$, $R^{106}$ and $R^{107}$ are each independently a $C_1$-$C_{20}$ monovalent hydrocarbon group which may contain a heteroatom. The monovalent hydrocarbon group may be straight, branched or cyclic, and examples thereof include $C_1$-$C_{12}$ alkyl, $C_2$-$C_{12}$ alkenyl, $C_2$-$C_{12}$ alynyl, $C_6$-$C_{20}$ aryl, and $C_7$-$C_{12}$ aralkyl groups. In these groups, some or all of the hydrogen atoms may be substituted by hydroxyl, carboxyl, halogen, cyano, amide, nitro, mercapto, sultone, sulfone, or sulfonium salt-containing moieties, and some carbon may be replaced by an ether bond, ester bond, carbonyl moiety, carbonate moiety or sulfonic acid ester bond. Any two of $R^{103}$, $R^{104}$ and $R^{105}$ may bond together to form a ring with the sulfur atom to which they are attached. The thus formed ring is as exemplified above for the case where two $R^5$ bond together to form a ring with the sulfur atom in formula (1).

In formulae (2) and (3), x is an integer of 1 to 3, y is an integer of 1 to 5, and z is an integer of 0 to 3, and 1≤y+z≤5. Preferably, y is an integer of 1 to 3, more preferably 2 or 3, and z is an integer of 0 to 2.

Examples of the anion in the onium salts having formulae (2) and (3) are as exemplified in JP-A 2018-005224 and JP-A 2018-025789.

An acid generator obtained by combining an anion in formula (2) or (3) with a cation in formula (1) is also useful. In this case, since the number of iodine atoms in the acid generator increases, the absorption of EUV becomes more, with a higher sensitivity being expectable.

When used, the acid generator is preferably added in an amount of 0.01 to 300 parts, and more preferably 0.1 to 100 parts by weight per 100 parts by weight of the base polymer.

Examples of the organic solvent are described in JP-A 2008-111103, paragraphs [0144]-[0145] (U.S. Pat. No. 7,537,880). Suitable solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

In the resist composition of the invention, a quencher other than the sulfonium salt having formula (1) may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with 1 to sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer. The other quencher may be used alone or in admixture.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of a resist film in exposed area.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker. The crosslinker may be used alone or in admixture.

Examples of the epoxy compound include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

To the resist composition, a polymeric additive or water repellency improver may also be added for improving the water repellency on surface of a resist film as spin coated. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. The water repellency improver may be used alone or in admixture. An appropriate amount of the water repellency improver is 0 to 20 parts, more preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Pattern Forming Process

The resist composition is used in the fabrication of various integrated circuits. Pattern formation using the resist composition may be performed by well-known lithography processes. The process generally involves coating, prebaking, exposure, and development. If necessary, any additional steps may be added.

For example, the resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate preferably at a temperature of 60 to 150° C. for 10 seconds to 30 minutes, more preferably at 80 to 120° C. for 30 seconds to 20 minutes. The resulting resist film is generally 0.01 to 2 µm thick.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto through a mask having a desired pattern in a dose of preferably about 1 to 200 $mJ/cm^2$, more preferably about 10 to 100 $mJ/cm^2$. When EB is used as the high-energy radiation, the resist film is exposed thereto through a mask having a desired pattern or directly in a dose of preferably about 0.1 to 100 $\mu C/cm^2$, more preferably about 0.5 to 50 $\mu C/cm^2$. It is appreciated that the inventive resist composition is suited in micropatterning using KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hot plate at 60 to 150° C. for 10 seconds to 30 minutes, preferably at 80 to 120° C. for 30 seconds to 20 minutes.

After the exposure or PEB, in the case of positive resist, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetopheinone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Quenchers 1 to 21 in the form of sulfonium salts used in resist compositions have the structure shown below. Quencher 1 was synthesized by etherifying reaction of a p-fluorophenyldiphenylsulfonium salt with 1-hydroxyethoxy-2,4,6-triiodobenzene. Quenchers 2, 3, and 4 were synthesized by similar etherifying reaction. Quenchers 5 to 15 were synthesized by esterifying reaction. Quenchers 16 to 21 were synthesized by acetal reaction of a hydroxyphenyldiphenylsulfonium salt with a vinyl ether compound having iodized aromatic and alkenyl groups, or by etherifying reaction of a hydroxyphenyldiphenylsulfonium salt with a methyl chloride having an iodized phenoxy group.

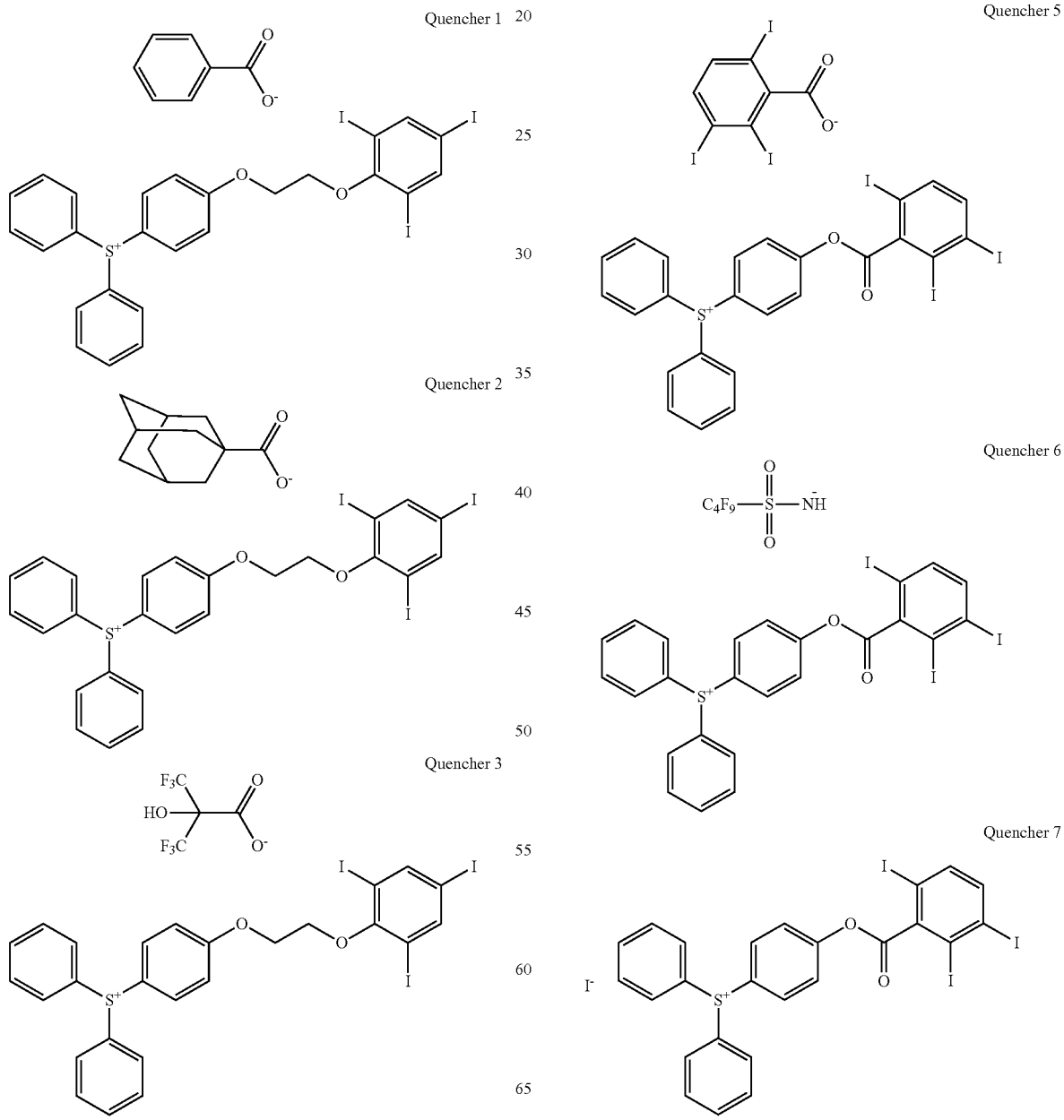

Quencher 8
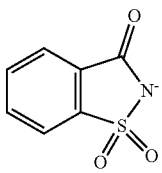
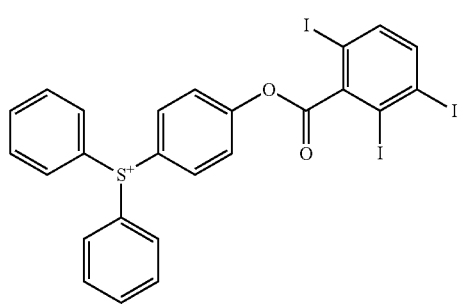
Quencher 9
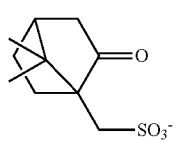
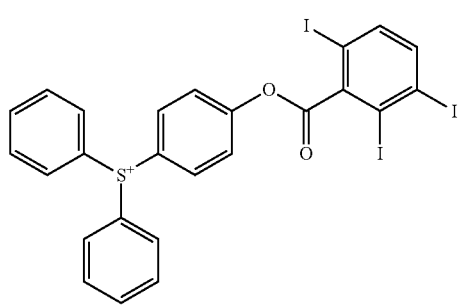
Quencher 10
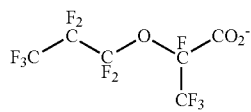
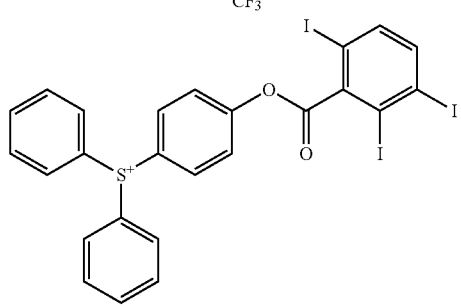
Quencher 11
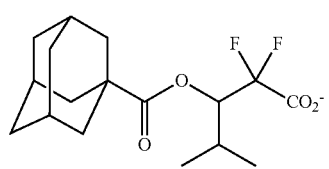
Quencher 12
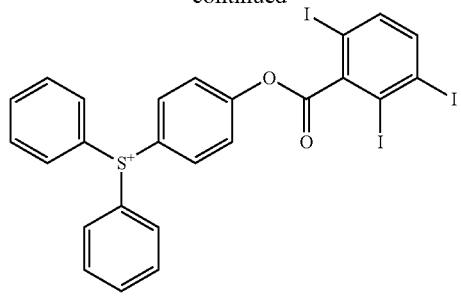
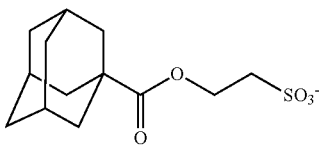
Quencher 13
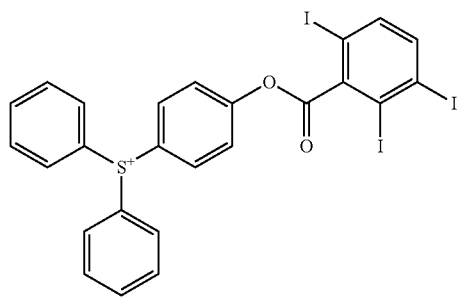
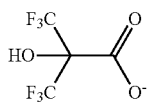
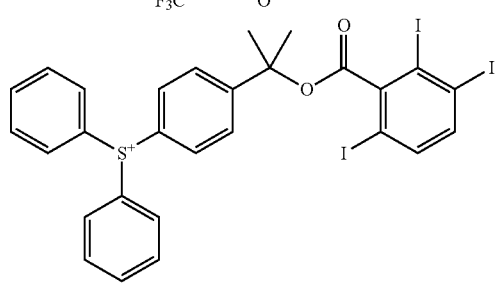
Quencher 14
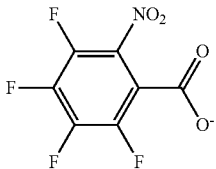
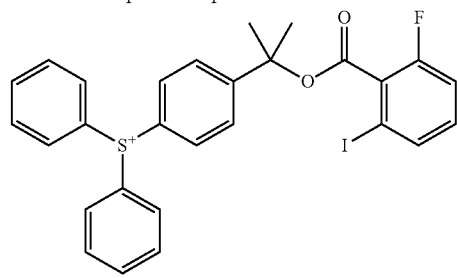

-continued

Quencher 15

Quencher 16

Quencher 17

Quencher 18

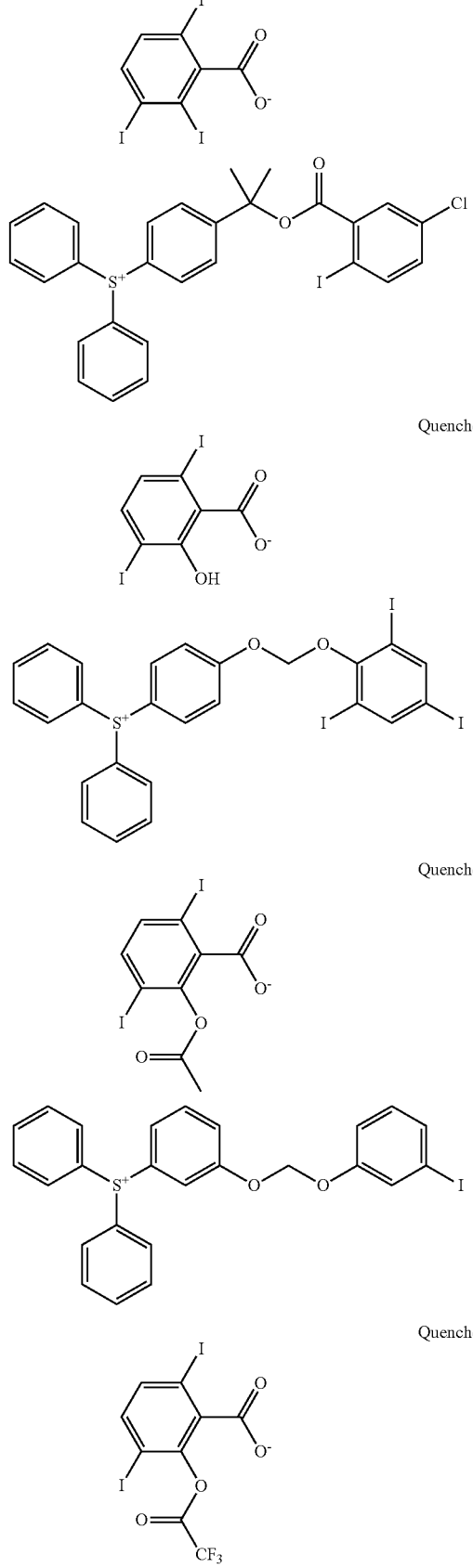

-continued

Quencher 19

Quencher 20

Quencher 21

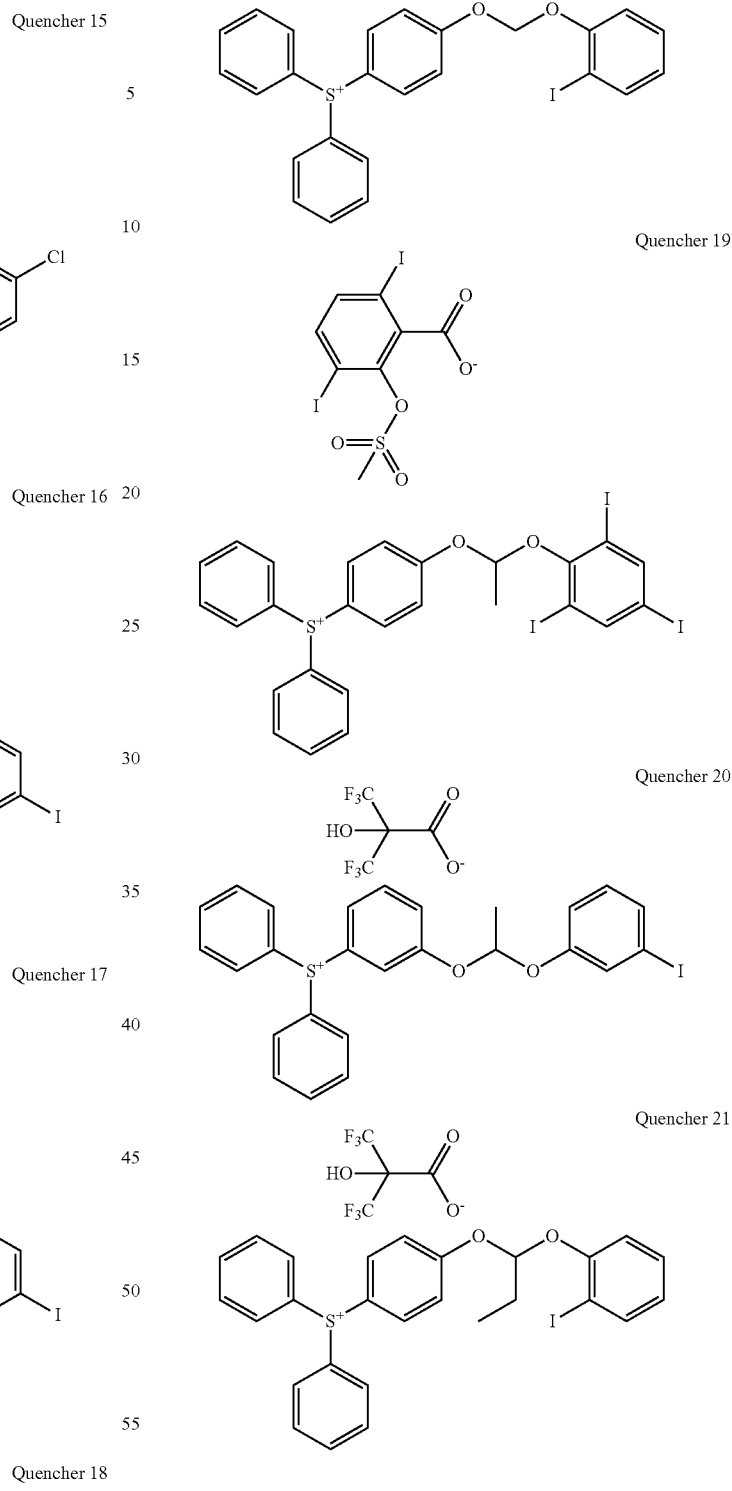

Synthesis Example

Synthesis of Base Polymers (Polymers 1 to 4)

Base polymers were prepared by combining suitable monomers, effecting copolymerization reaction thereof in tetrahydrofilran (THF) solvent, pouring the reaction solution into methanol for crystallization, repeatedly washing with hexane, isolation, and drying. The resulting polymers, designated Polymers 1 to 4, were analyzed for composition by ¹H-NMR spectroscopy, and for Mw and Mw/Mn by GPC versus polystyrene standards using THF solvent.

Polymer 1

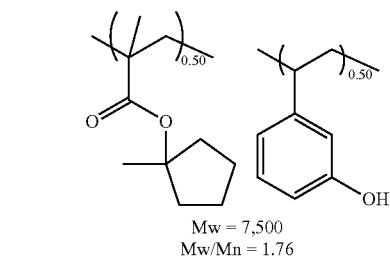

Mw = 7,500
Mw/Mn = 1.76

Polymer 2

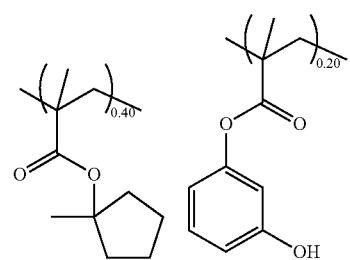

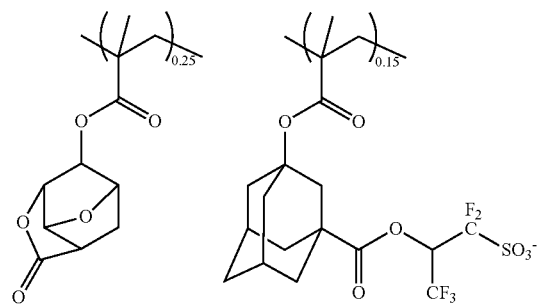

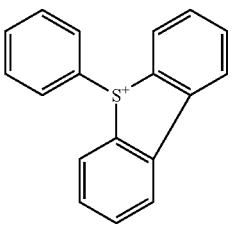

Mw = 8,300
Mw/Mn = 1.69

Polymer 3

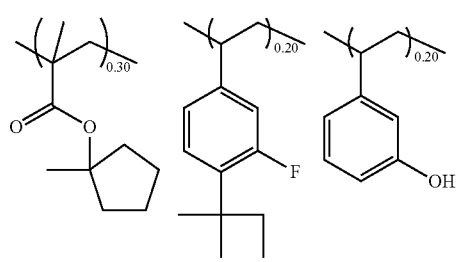

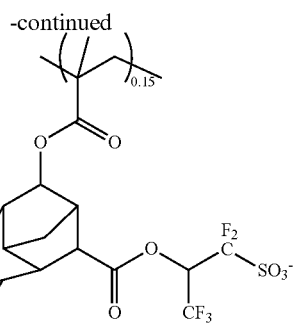

Mw = 9,800
Mw/Mn = 1.66

Polymer 4

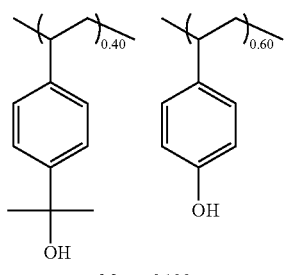

Mw = 6,100
Mw/Mn = 1.54

Examples 1 to 24 and Comparative Examples 1 to 4

(1) Preparation of Resist Composition

Resist compositions were prepared by dissolving components in a solvent in accordance with the recipe shown in Tables 1 to 3, and filtering through a filter having a pore size of 0.2 μm. The solvent contained 100 ppm of surfactant PF636 (Omnova Solutions Inc.). The components in Tables 1 to 3 are as identified below.

Organic Solvents:
  PGMEA (propylene glycol monomethyl ether acetate)
  GBL (γ-butyrolactone)
  CyH (cyclohexanone)
  PGME (propylene glycol monomethyl ether)
  DAA (diacetone alcohol)

Acid generators: PAG 1 to PAG 3 of the following structural formulae

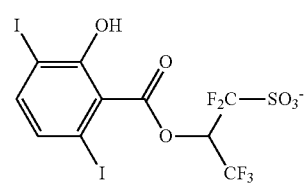

PAG 1

-continued

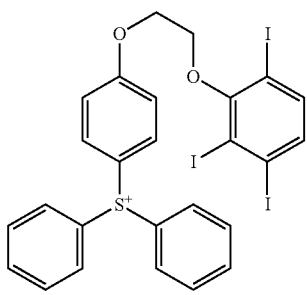

PAG 2

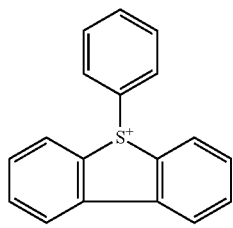

PAG 3

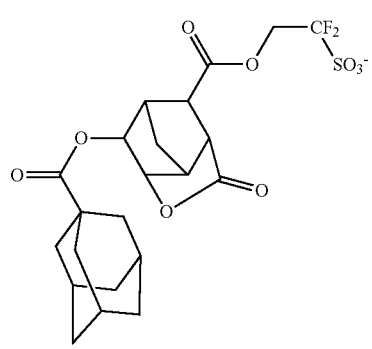

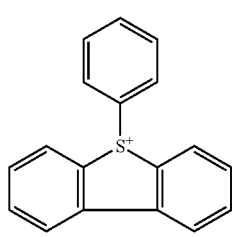

Comparative Quenchers 1 to 3 of the following structural formulae

Comparative Quencher 1

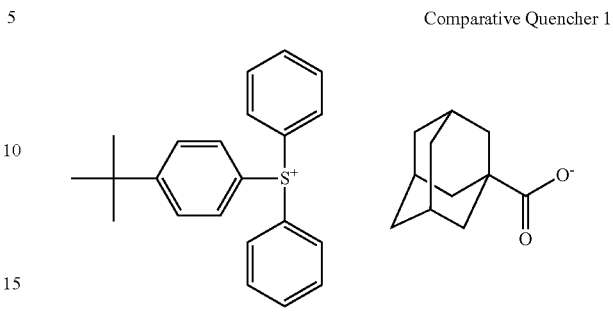

Comparative Quencher 2

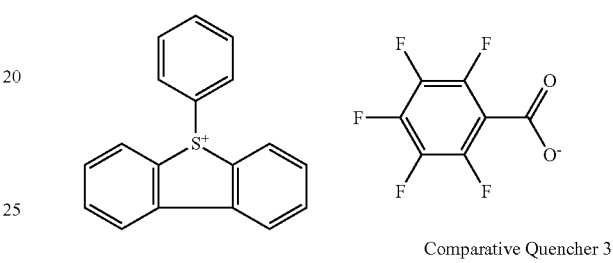

Comparative Quencher 3

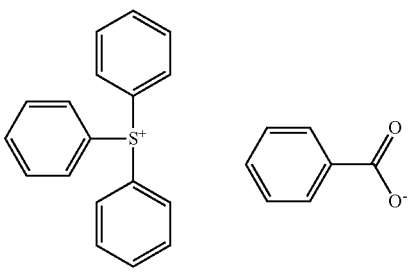

(2) EUV Lithography Test

Each of the resist compositions in Tables 1 to 3 was spin coated on a silicon substrate having a 20-nm coating of silicon-containing spin-on hard mask SHB-A940 (Shin-Etsu Chemical Co., Ltd., Si content 43 wt %) and prebaked on a hotplate at 105° C. for 60 seconds to form a resist film of 50 nm thick. Using an EUV scanner NXE3300 (ASML, NA 0.33, σ 0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Tables 1 to 3 for 60 seconds and developed in a 2.38 wt % TMAH aqueous solution for 30 seconds to form a pattern. In Examples 1 to 14, 16 to 24 and Comparative Examples 1 to 3, a positive resist pattern, i.e., hole pattern having a size of 23 nm was formed. In Example 15 and Comparative Example 4, a negative resist pattern, i.e., dot pattern having a size of 26 nm was formed.

The resist pattern was observed under CD-SEM (CG-5000, Hitachi High-Technologies Corp.). The exposure dose that provides a hole or dot pattern having a size of 23 nm or 26 nm is reported as sensitivity. The size of 50 holes or dots was measured, from which a size variation (3σ) was computed and reported as CDU.

The resist composition is shown in Tables 1 to 3 together with the sensitivity and CDU of EUV lithography.

TABLE 1

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 1 | Polymer 1 (100) | PAG 1 (26.7) | Quencher 1 (8.97) | PGMEA (400) CyH (2,000) PGME (100) | 95 | 24 | 3.8 |
|  | 2 | Polymer 1 (100) | PAG 2 (21.2) | Quencher 1 (8.97) | PGMEA (400) CyH (2,000) PGME (100) | 95 | 23 | 3.0 |
|  | 3 | Polymer 1 (100) | PAG 3 (15.3) | Quencher 1 (4.48) Quencher 2 (4.78) | PGMEA (2,000) DAA (500) | 95 | 29 | 3.2 |
|  | 4 | Polymer 2 (100) | — | Quencher 2 (9.56) | PGMEA (2,000) DAA (500) | 90 | 24 | 2.7 |
|  | 5 | Polymer 2 (100) | — | Quencher 3 (9.88) | PGMEA (2,000) DAA (500) | 90 | 22 | 2.1 |
|  | 6 | Polymer 2 (100) | — | Quencher 4 (10.42) | PGMEA (2,000) DAA (500) | 90 | 22 | 2.5 |
|  | 7 | Polymer 2 (100) | — | Quencher 5 (12.59) | PGMEA (2,000) DAA (500) | 90 | 20 | 2.3 |
|  | 8 | Polymer 2 (100) | — | Quencher 6 (10.58) | PGMEA (2,000) DAA (500) | 90 | 26 | 2.7 |
|  | 9 | Polymer 2 (100) | — | Quencher 7 (8.87) | PGMEA (2,000) DAA (500) | 90 | 21 | 3.1 |
|  | 10 | Polymer 2 (100) | — | Quencher 8 (9.43) | PGMEA (2,000) DAA (500) | 90 | 26 | 2.7 |
|  | 11 | Polymer 2 (100) | — | Quencher 9 (9.92) | PGMEA (2,000) DAA (500) | 90 | 24 | 2.9 |
|  | 12 | Polymer 2 (100) | — | Quencher 10 (10.90) | PGMEA (2,000) DAA (500) | 90 | 22 | 2.7 |
|  | 13 | Polymer 2 (100) | — | Quencher 11 (10.90) | PGMEA (2,000) GBL (500) | 90 | 21 | 2.9 |
|  | 14 | Polymer 3 (100) | — | Quencher 12 (10.32) | PGMEA (2,000) GBL (500) | 90 | 22 | 3.0 |
|  | 15 | Polymer 4 (100) | PAG 3 (15.3) | Quencher 3 (9.88) | PGMEA (2,000) DAA (500) | 130 | 31 | 3.2 |

TABLE 2

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 16 | Polymer 2 (100) | — | Quencher 13 (9.88) | PGMEA (2,000) DAA (500) | 90 | 21 | 2.8 |
|  | 17 | Polymer 2 (100) | — | Quencher 14 (9.88) | PGMEA (2,000) DAA (500) | 90 | 20 | 2.6 |
|  | 18 | Polymer 2 (100) | — | Quencher 15 (9.88) | PGMEA (2,000) DAA (500) | 90 | 19 | 2.9 |
|  | 19 | Polymer 2 (100) | — | Quencher 16 (9.88) | PGMEA (2,000) DAA (500) | 90 | 20 | 2.6 |
|  | 20 | Polymer 2 (100) | — | Quencher 17 (9.88) | PGMEA (2,000) DAA (500) | 90 | 22 | 2.7 |
|  | 21 | Polymer 2 (100) | — | Quencher 18 (9.88) | PGMEA (2,000) DAA (500) | 90 | 21 | 2.6 |
|  | 22 | Polymer 2 (100) | — | Quencher 19 (9.88) | PGMEA (2,000) DAA (500) | 90 | 20 | 2.7 |
|  | 23 | Polymer 2 (100) | — | Quencher 20 (9.56) | PGMEA (2,000) DAA (500) | 90 | 24 | 2.7 |
|  | 24 | Polymer 2 (100) | — | Quencher 21 (9.88) | PGMEA (2,000) DAA (500) | 90 | 22 | 2.1 |

TABLE 3

|  |  | Polymer (pbw) | Acid generator (pbw) | Base (pbw) | Organic solvent (pbw) | PEB temp. (° C.) | Sensitivity (mJ/cm$^2$) | CDU (nm) |
|---|---|---|---|---|---|---|---|---|
| Comparative Example | 1 | Polymer 1 (100) | PAG 1 (26.7) | Comparative Quencher 1 (4.98) | PGMEA (400) CyH (2,000) PGME (100) | 95 | 39 | 4.5 |
|  | 2 | Polymer 2 (100) | — | Comparative Quencher 2 (4-72) | PGMEA (400) CyH (2,000) PGME (100) | 90 | 37 | 3.9 |
|  | 3 | Polymer 2 (100) | — | Comparative Quencher 3 (3.84) | PGMEA (400) CyH (2,000) PGME (100) | 90 | 36 | 4.0 |

TABLE 3-continued

| | Polymer (pbw) | Acid generator (pbw) | Base (pbw) | Organic solvent (pbw) | PEB temp. (° C.) | Sensitivity (mJ/cm$^2$) | CDU (nm) |
|---|---|---|---|---|---|---|---|
| 4 | Polymer 4 (100) | PAG 3 (15.3) | Comparative Quencher 3 (3.84) | PGMEA (2,000) DAA (500) | 130 | 45 | 5.2 |

It is demonstrated in Tables 1 to 3 that resist compositions comprising a sulfonium salt having an iodized benzene ring as a quencher offer a high sensitivity and improved CDU.

Japanese Patent Application No. 2018-173598 is incorporated herein by reference.

Although some preferred embodiments have been described, many modifications and variations may be made thereto in light of the above teachings. It is therefore to be understood that the invention may be practiced otherwise than as specifically described to without departing from the scope of the appended claims.

The invention claimed is:

1. A resist composition comprising a quencher containing a sulfonium salt having the formula (1):

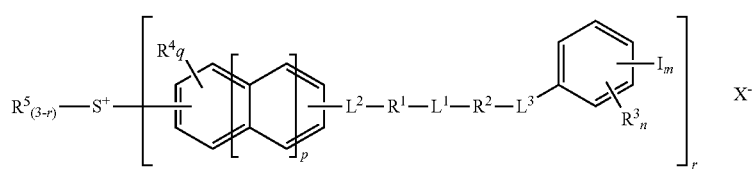

wherein $R^1$ and $R^2$ are each independently a single bond or a $C_1$-$C_{20}$ divalent aliphatic hydrocarbon group which may contain an ether bond, ester bond or hydroxyl, $L^1$ is an ester bond, ether bond or amide bond, $L^2$ and $L^3$ are each independently a single bond, ester bond, ether bond or amide bond, $R^3$ is hydroxyl, carboxyl, nitro, cyano, fluorine, chlorine, bromine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, hydroxyl or amino, or —NR$^{3A}$—C(=O)—R$^{3B}$ or —NR$^{3A}$—C(=O)—O—R$^{3B}$, wherein $R^{3A}$ is hydrogen or a $C_1$-$C_6$ alkyl group which may contain halogen, hydroxyl, $C_1$-$C_{10}$ alkoxy, $C_2$-$C_{10}$ acyl or $C_2$-$C_{10}$ acyloxy, $R^{3B}$ is a $C_1$-$C_{16}$ alkyl, $C_2$-$C_{16}$ alkenyl or $C_6$-$C_{12}$ aryl group, which may contain halogen, hydroxyl, $C_1$-$C_{10}$ alkoxy, $C_2$-$C_{10}$ acyl or $C_2$-$C_{10}$ acyloxy, $R^4$ is hydroxyl, carboxyl, nitro, cyano, fluorine, chlorine, bromine, iodine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, iodine, hydroxyl, amino or ether bond, $R^5$ is a $C_1$-$C_{20}$ monovalent hydrocarbon group which may contain a heteroatom, in case of r=1, two $R^5$ may be the same or different and may bond together to form a ring with the sulfur atom to which they are attached, X$^-$ is a carboxylic acid anion, amic acid anion, fluorine-free sulfonic acid anion or halide ion, m is an integer of 1 to 5, n is an integer of 0 to 3, the sum of m+n is 1 to 5, p is 0 or 1, q is an integer of 0 to 4, and r is an integer of 1 to 3.

2. The resist composition of claim 1 wherein m is an integer of 2 to 5.

3. The resist composition of claim 1, further comprising an organic solvent.

4. The resist composition of claim 1, further comprising an acid generator capable of generating a fluorosulfonic acid, fluoroimidic acid or fluoromethide acid.

5. The resist composition of claim 1, further comprising a base polymer.

6. The resist composition of claim 5 wherein the base polymer comprises recurring units having the formula (a1) or recurring units having the formula (a2):

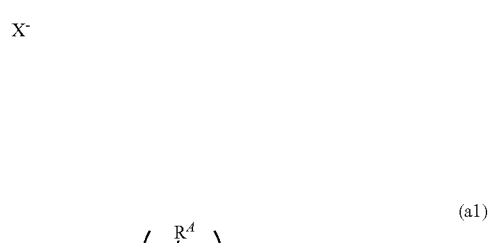

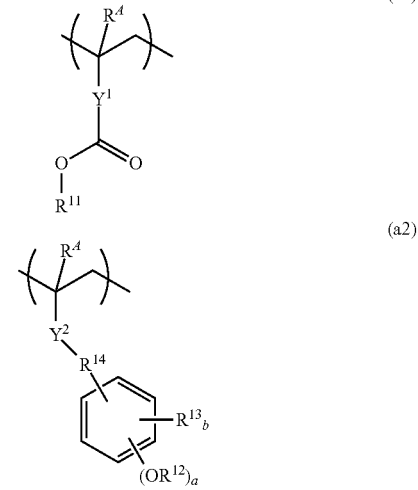

wherein $R^A$ is each independently hydrogen or methyl, $Y^1$ is a single bond, phenylene group, naphthylene group, or $C_1$-$C_{12}$ linking group containing an ester bond or lactone ring, $Y^2$ is a single bond or ester bond, $R^{11}$ and $R^{12}$ each are an acid labile group, $R^{13}$ is fluorine, trifluoromethyl, cyano, $C_1$-$C_6$ alkyl, $C_1$-$C_6$ alkoxy, $C_2$-$C_7$ acyl, $C_2$-$C_7$ acyloxy, or $C_2$-$C_7$ alkoxycarbonyl group, $R^4$ is a single bond or a $C_1$-$C_6$ straight or branched alkanediyl group in which some carbon may be replaced by an ether bond or ester bond, a is 1 or 2, b is an integer of 0 to 4, the sum of a+b is 1 to 5.

7. The resist composition of claim 6 which is a chemically amplified positive resist composition.

8. The resist composition of claim 5 wherein the base polymer is free of an acid labile group.

9. The resist composition of claim 8 which is a chemically amplified negative resist composition.

10. The resist composition of claim 5 wherein the base polymer further comprises recurring units of at least one type selected from the formulae (f1) to (f3):

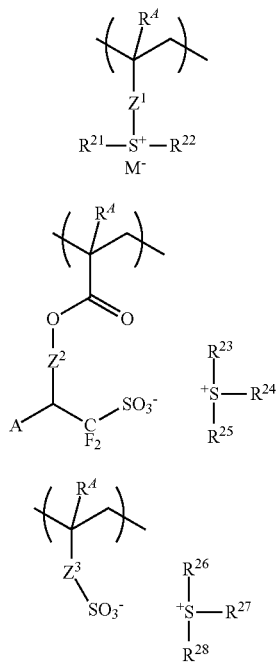

wherein $R^A$ is each independently hydrogen or methyl, $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain carbonyl, ester bond, ether bond or hydroxyl, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain carbonyl, ester bond or ether bond, $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain carbonyl, ester bond, ether bond or hydroxyl, $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, A is hydrogen or trifluoromethyl, and $M^-$ is a non-nucleophilic counter ion.

11. The resist composition of claim 1, further comprising a surfactant.

12. A process for forming a pattern comprising the steps of applying the resist composition of claim 1 onto a substrate, baking to form a resist film, exposing the resist film to high-energy radiation, and developing the exposed resist film in a developer.

13. The process of claim 12 wherein the high-energy radiation is ArF excimer laser radiation of wavelength 193 nm or KrF excimer laser radiation of wavelength 248 nm.

14. The process of claim 12 wherein the high-energy radiation is EB or EUV of wavelength 3 to 15 nm.

15. The resist composition of claim 1 wherein the carboxylic acid anion is selected from the group consisting of the following formulae:

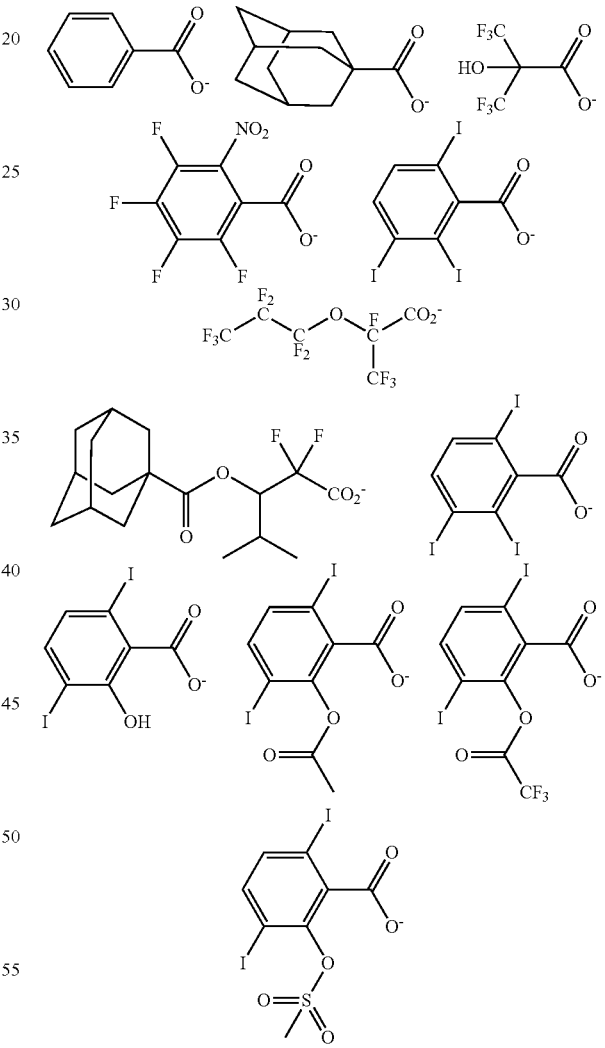

* * * * *